US012721847B2

(12) United States Patent
MacDonald et al.

(10) Patent No.: US 12,721,847 B2
(45) **Date of Patent: *Sep. 1, 2026**

(54) METHODS OF TREATING ERYTHROPOIETIC PROTOPORPHYRIA, X-LINKED PROTOPORPHYRIA, OR CONGENITAL ERYTHROPOIETIC PORPHYRIA WITH GLYCINE TRANSPORT INHIBITORS

(71) Applicant: Disc Medicine, Inc., Watertown, MA (US)

(72) Inventors: Brian Richard MacDonald, Watertown, MA (US); Maria Gabriela Beconi, Watertown, MA (US); Vu Hong, Watertown, MA (US)

(73) Assignee: Disc Medicine, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/226,633

(22) Filed: Jul. 26, 2023

(65) Prior Publication Data

US 2026/0232656 A1 Aug. 13, 2026

Related U.S. Application Data

(63) Continuation of application No. 17/145,086, filed on Jan. 8, 2021, now Pat. No. 11,813,257.

(60) Provisional application No. 63/085,942, filed on Sep. 30, 2020, provisional application No. 62/958,892, filed on Jan. 9, 2020.

(51) Int. Cl.

| | |
|---|---|
| ***A61K 31/496*** | (2006.01) |
| ***A61K 31/69*** | (2006.01) |
| ***A61K 31/785*** | (2006.01) |
| ***A61K 33/26*** | (2006.01) |
| ***A61K 33/44*** | (2006.01) |
| ***A61K 35/14*** | (2015.01) |
| ***A61K 35/28*** | (2015.01) |
| ***A61K 35/407*** | (2015.01) |
| ***A61K 38/10*** | (2006.01) |
| ***A61K 45/06*** | (2006.01) |
| ***A61P 1/16*** | (2006.01) |

(52) U.S. Cl.

CPC ............ *A61K 31/496* (2013.01); *A61K 31/69* (2013.01); *A61K 31/785* (2013.01); *A61K 33/26* (2013.01); *A61K 33/44* (2013.01); *A61K 35/14* (2013.01); *A61K 35/28* (2013.01); *A61K 35/407* (2013.01); *A61K 38/10* (2013.01); *A61K 45/06* (2013.01); *A61P 1/16* (2018.01)

(58) Field of Classification Search

CPC ..... A61K 31/496; A61K 31/69; A61K 31/785

See application file for complete search history.

(56) References Cited

U.S. PATENT DOCUMENTS

| | | | |
|---|---|---|---|
| 7,196,234 | B2 | 3/2007 | Doswald et al. |
| 7,319,099 | B2 | 1/2008 | Jolidon et al. |
| 7,504,544 | B2 | 3/2009 | Puentener et al. |
| 7,605,163 | B2 | 10/2009 | Jolidon et al. |
| 7,812,161 | B2 | 10/2010 | Pfleger et al. |
| 8,039,473 | B2 | 10/2011 | Bubendorf et al. |
| 8,124,639 | B2 | 2/2012 | McHardy et al. |
| 8,188,139 | B2 | 5/2012 | Jolidon et al. |
| 9,012,489 | B2 | 4/2015 | Giovannini et al. |
| 9,233,953 | B2 | 1/2016 | Hoenke et al. |
| 9,877,963 | B2 | 1/2018 | Alberati et al. |
| 11,813,257 | B2 | 11/2023 | MacDonald et al. |
| 2005/0281781 | A1 | 12/2005 | Ostroff |
| 2016/0271126 | A1 | 9/2016 | Buurman et al. |
| 2017/0042888 | A1 | 2/2017 | Alberati et al. |
| 2022/0249473 | A1 | 8/2022 | Ma |
| 2024/0269132 | A1 | 8/2024 | Quisel et al. |
| 2024/0325382 | A1 | 10/2024 | MacDonald et al. |
| 2024/0366574 | A1 | 11/2024 | MacDonald et al. |
| 2024/0390362 | A1 | 11/2024 | MacDonald et al. |
| 2025/0228827 | A1 | 7/2025 | MacDonald et al. |
| 2025/0248995 | A1 | 8/2025 | Quisel et al. |
| 2025/0262204 | A1 | 8/2025 | MacDonald et al. |
| 2025/0302823 | A1 | 10/2025 | Beconi et al. |
| 2026/0027107 | A1 | 1/2026 | Quisel et al. |

FOREIGN PATENT DOCUMENTS

| | | |
|---|---|---|
| WO | WO2005/094514 | 10/2005 |
| WO | WO2006/082001 | 8/2006 |
| WO | WO2008/080821 | 7/2008 |
| WO | WO2009/068463 | 6/2009 |
| WO | WO2012/019970 | 2/2012 |

(Continued)

OTHER PUBLICATIONS

Winter, M. et al. "Effects of GlyT1 inhibition on erythropoiesis and iron homeostasis in rats" Experimental Hematology 2016;44:964-974 (Year: 2016).*

PorphyriaFoundation (https://porphyriafoundation.org/for-patients/types-of-porphyria/epp-xlp/) pp. 1-9, accessed 2023 (Year: 2023).*

U.S. Appl. No. 18/647,495, filed Apr. 26, 2024, Disc Medicine, Inc.

Balwani M., et al., "Clinical, Biochemical, and Genetic Characterization of North American Patients With Erythropoietic Protoporphyria and X-linked Protoporphyria", JAMA DermatolOGY, 2017; 153(8):789-796.(Aug. 9, 2017).

Cioffi, "Glycine transporter-1 inhibitors: a patent review (2011-2016)"; Expert Opinion on Therapeutic Patents, 2018, pp. 1-14. https://doi.org/10.1080/13543776.2018.1429408.

Citrome, "A Review of the Pharmacology, Efficacy and Tolerability of Recently Approved and Upcoming Oral Antipsychotics: An Evidence-Based Medicine Approach", CNS Drugs (2013) 27, pp. 879-911.

(Continued)

*Primary Examiner* — Andrew S Rosenthal
(74) *Attorney, Agent, or Firm* — White & Case LLP

(57) ABSTRACT

The present embodiments are directed to methods of using glycine transporter inhibitors, such as GlyT1 inhibitors, or pharmaceutically acceptable salts, solvates or prodrugs thereof, or pharmaceutical compositions thereof, for preventing or treating erythropoietic protoporphyria (EPP), X-linked protoporphyria (XLPP), and/or congenital erythropoietic porphyria (CEP), and related syndromes thereof.

3 Claims, 11 Drawing Sheets

Specification includes a Sequence Listing.

(56) References Cited

FOREIGN PATENT DOCUMENTS

| | | |
|---|---|---|
| WO | WO2015/165842 | 11/2015 |
| WO | WO2018/192973 | 10/2018 |
| WO | WO2020/223419 | 11/2020 |
| WO | WO2021/142329 | 7/2021 |
| WO | WO2022/192730 | 9/2022 |
| WO | WO2022/192731 | 9/2022 |
| WO | WO2022/241274 | 11/2022 |
| WO | WO2022/251458 | 12/2022 |
| WO | WO2023/235326 | 12/2023 |
| WO | WO2025/059425 | 3/2025 |

OTHER PUBLICATIONS

Dawe, "An overview of the cutaneous porphyrias", F1000Research (2017), 6(F1000 Faculty Rev):1906, pp. 1-11.

Freed, et al., "When ribosomes go bad: diseases of ribosome biogenesis", Mol Biosyst. Mar. 2010 ; 6(3); pp. 481-493.

Halloy, et al., "Repurposing of glycine transport inhibitors for the treatment of erythropoietic protoporphyria", Cell Chemical Biology (2021) vol. 28, pp. 1-14; 1221-1234, e1-e6; (Epub Mar. 22, 2021). https://doi.org/10.1016/j.chembiol.2021.02.021.

History of Changes for Study NCT05308472, "Study of Bitopertin to Evaluate the Safety, Tolerability, Efficacy, and PPIX Concentrations in Particpants With EPP," Mar. 24, 2022, Retrieved from www.clinicaltrials.gov on May 7, 2023, Title: Brief Summary, Study Description, Arms and Interventions, Outcome measure and Eligibility.

Heerfordt, et al., "Protoporphyrin IX in the skin measured noninvasively predicts photosensitivity in patients with erythropoietic protoporphyria", British Journal of Dermatology (2016) 175, pp. 1284-1289.

Linenberger, et al., "Updates on the diagnosis and management of the most common hereditary porphyrias: AIP and EPP", Hematology 2020, pp. 400-410. DOI 10.1182/hematology.2020000124.

Matte, et al., "Bitopertin, a selective oral GLYT1 inhibitor, improves anemia in a mouse model of β-thalassemia", JCI Insight (2019); 4(22); pp. 1-16: e130111.; https://doi.org/10.1172/jci.insight.130111.

Pinard, et al., "Discovery of benzoylisoindolines as a novel class of potent, selective and orally active GlyT1 inhibitors", Bioorganic & Medicinal Chemistry Letters 20 (2010), pp. 6960-6965.

Pinard, et al., "Glycine Transporter Type I (GlyT1) Inhibitor, Bitopertin: A Journey from Lab to Patient", SCS Laureates and Awards & Fall Meeting 2018, Chimia 72 (2018), pp. 477-484.

Winter, et al., "Effects of GlyT1 inhibition on erythropoiesis and iron homeostasis in rats", Experimental Hematology (2016) vol. 44, pp. 964-974, 974.e1-974.e4.

Wulf HC, et al., "Inactivation of protoporphyrin IX in erythrocytes in patients with erythropoietic protoporphyria: A new treatment modality", Photodiagnosis Photodyn Ther. 2020;29:101582.(Dec. 3, 2019).

Yang, et al., "Delayed globin synthesis leads to excess heme and the macrocytic anemia of Diamond Blackfan anemia and del(5q) myelodysplastic syndrome", Science Translational Medicine, May 11, 2016; vol. 8 Issue 338 338ra67; pp. 1-9.

PCT International Search Report for PCT/US2021/012786, dated Apr. 12, 2021 (7 pages).

PCT International Search Report for PCT/US2023/023886, dated Jul. 25, 2023 (17 pages).

PCT International Search Report for PCT/US2022/029283, dated Aug. 2, 2022 (6 pages).

PCT International Search Report for PCT/US2022/031081, dated Aug. 2, 2022 (6 pages).

Puy, et al., "Heme-Related Blood Disorders", Blood, 2013, vol. 122, No. 21, http://doi.org/10.1182/blood.V122.21.SCI-18.SCI-18.

* cited by examiner

Genotype

FECH protein level

SEQUENCE LISTING

```
Sequence total quantity: 5
SEQ ID NO: 1            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 1
atgggaggcc ctgaaactct                                              20

SEQ ID NO: 2            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 2
tgaaactctt ggagatgttc                                              20

SEQ ID NO: 3            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
```

-continued

```
                        organism = synthetic construct
SEQUENCE: 3
tctgagactc ttcttggacc                                              20

SEQ ID NO: 4            moltype = DNA  length = 58
FEATURE                 Location/Qualifiers
misc_feature            1..58
                        note = Description of Artificial Sequence: Synthetic
                         oligonucleotide
source                  1..58
                        mol_type = other DNA
                        organism = synthetic construct
SEQUENCE: 4
ccgggctttg cagatcatat tctaactcga gttagaatat gatctgcaaa gctttttg    58

SEQ ID NO: 5            moltype = DNA  length = 58
FEATURE                 Location/Qualifiers
misc_feature            1..58
                        note = Description of Artificial Sequence: Synthetic
                         oligonucleotide
source                  1..58
                        mol_type = other DNA
                        organism = synthetic construct
SEQUENCE: 5
aattcaaaaa gctttgcaga tcatattcta actcgagtta gaatatgatc tgcaaagc    58
```

METHODS OF TREATING ERYTHROPOIETIC PROTOPORPHYRIA, X-LINKED PROTOPORPHYRIA, OR CONGENITAL ERYTHROPOIETIC PORPHYRIA WITH GLYCINE TRANSPORT INHIBITORS

RELATED APPLICATIONS

This application is a continuation of U.S. application Ser. No. 17/145,086, filed Jan. 8, 2021 (now U.S. Pat. No. 11,813,257), which claims the benefit of and priority to U.S. Provisional Patent Application No. 62/958,892, filed Jan. 9, 2020, and U.S. Provisional Patent Application No. 63/085,942, filed Sep. 30, 2020, U.S. Patent Application No. 63/085,942, filed Sep. 30, 2020 (now expired). The specifications of each of the foregoing applications are incorporated herein by reference in their entirety

SEQUENCE LISTING

The instant application contains a Sequence Listing which has been filed electronically in XML format and is hereby incorporated by reference in its entirety. Said XML copy, created on Oct. 7, 2025, is named 1887094-0002-002-102_SL.xml and is 7,775 bytes in size.

FIELD

Embodiments disclosed herein are directed to methods and uses to prevent or treat erythropoietic protoporphyria (EPP), X-linked protoporphyria (XLPP), or congenital erythropoietic porphyria (CEP) with glycine transporter inhibitors, such as, but not limited to, GlyT1 inhibitors, or pharmaceutically acceptable salts, solvates, prodrugs thereof, or pharmaceutical compositions thereof.

BACKGROUND

Erythropoietic protoporphyria (EPP) is prevalent globally and affects about 5,000-10,000 individuals worldwide (Michaels et al. 2010). EPP is considered the most common form of porphyria in children. Erythropoietic protoporphyria is a form of porphyria, which varies in severity and can be very painful. It arises from a deficiency in the enzyme ferrochelatase, leading to abnormally high levels of protoporphyrin IX in red blood cells (erythrocytes), plasma, skin, and liver. Erythropoietic protoporphyria (EPP) is due to an inherited or acquired deficiency in the activity of the enzyme ferrochelatase. X-linked protoporphyria (XLPP) is due to an inherited increase in the activity of delta-aminolevulinic acid synthase-2 (ALAS2). Enzymes that cause both EPP and XLPP are in the heme biosynthetic pathway. EPP and XLPP are nearly identical clinically. Congenital erythropoietic porphyria (CEP), also known as Gunther disease, caused by mutations in the gene for uroporphyrinogen synthase resulting in reduced activity of this enzyme and accumulation of the upstream metabolite coproporphyrin I. Current treatments for erythropoietic protoporphyria (EPP), X-linked protoporphyria (XLPP), or congenital erythropoietic porphyria (CEP) are limited. Thus, there is a need for new methods and compositions for treating and/or preventing erythropoietic protoporphyria, X-linked protoporphyria, and congenital erythropoietic porphyria. The methods and use of glycine transporter inhibitors, such as, but not limited to, GlyT1 inhibitors, described herein fulfill these needs as well as others.

SUMMARY OF THE APPLICATION

The present application provides a method of treating erythropoietic protoporphyria (EPP), X-linked protoporphyria (XLPP), or congenital erythropoietic porphyria (CEP) in a subject, the method comprising administering to the subject a pharmaceutical composition comprising one or more glycine transporter 1 (GlyT1) inhibitor, or a pharmaceutically acceptable salt thereof, or a prodrug of the one or more GlyT1 inhibitor or its salt.

The present application further provides a method of preventing, treating, or reducing the progression rate and/or severity of one or more complications of EPP, XLPP, or CEP in a subject, the method comprising administering to the subject a pharmaceutical composition comprising one or more GlyT1 inhibitor, or a pharmaceutically acceptable salt thereof, or a prodrug of the one or more GlyT1 inhibitor or its pharmaceutically acceptable salt. In certain embodiments, the one or more complications of EPP, XLPP, or CEP is selected from the group consisting of: acute photosensitivity, cutaneous photosensitivity, edema, erythema, anemia, hypochromic anemia, hemolytic anemia, hemolysis, mild hemolysis, severe hemolysis, chronic hemolysis, hypersplenism, palmar keratoderma, bullae, lesions, scarring, deformities, loss of fingernails, loss of digits, cholestasis, cytolysis, gallstones, cholestatic liver failure, cholelithiasis, mild liver disease, deteriorating liver disease, terminal phase liver disease, erythrodontia, hypercellular bone marrow, myelodysplasia, thrombocytopenia, hydrops fetalis and/or death in utero. In certain such embodiments, the acute photosensitivity is due to sun exposure.

The present application further provides a method for use in preventing or treating EPP, XLPP, or CEP in a subject, wherein the use comprises administering to the subject a GlyT1 inhibitor, or a pharmaceutically acceptable salt thereof, or a prodrug of the one or more GlyT1 inhibitor or its pharmaceutically acceptable salt.

The present application further provides a method for use in the manufacture of a medicament for the treatment of EPP, XLPP, or CEP in a subject, the use comprising administering to the subject at least one GlyT1 inhibitor, or a pharmaceutically acceptable salt thereof, or a prodrug of the one or more GlyT1 inhibitor or its pharmaceutically acceptable salt.

The present application further provides a method for use in the manufacture of a medicament for inhibiting protoporphyrin IX (PPIX) synthesis in vivo, the use comprising administering to a subject a GlyT1 inhibitor, or a pharmaceutically acceptable salt thereof, or a prodrug of the one or more GlyT1 inhibitor or its pharmaceutically acceptable salt.

In certain embodiments, the subject has EPP. In other embodiments, the subject has XLPP. In yet other embodiments, the subject has CEP.

In certain embodiments, the method increases pain free light exposure in the subject. In other embodiments, the method decreases light sensitivity in the subject.

The present application further provides a method of inhibiting PPIX synthesis in vivo, comprising administering to a subject a GlyT1 inhibitor, or a pharmaceutically acceptable salt thereof, or a prodrug of the GlyT1 inhibitor or its pharmaceutically acceptable salt.

The present application further provides a method of inhibiting zinc protoporphyrin IX (ZPPIX) synthesis in vivo, comprising administering to a subject a GlyT1 inhibitor, or a pharmaceutically acceptable salt thereof, or a prodrug of the GlyT1 inhibitor or its pharmaceutically acceptable salt.

The present application further provides a method of inhibiting uroporphyrin I and/or coproporphyrin I synthesis in vivo, comprising administering to a subject a GlyT1 inhibitor, or a pharmaceutically acceptable salt thereof, or a prodrug of the GlyT1 inhibitor or its pharmaceutically acceptable salt.

The present application further provides a method of inhibiting 5-aminolevulinic acid (5-ALA) synthesis in vivo, comprising administering to a subject a GlyT1 inhibitor, or a pharmaceutically acceptable salt thereof, or a prodrug of the GlyT1 inhibitor or its pharmaceutically acceptable salt.

In certain embodiments, the accumulation of one or more heme intermediates is inhibited, and wherein the one or more heme intermediates are selected from the group consisting of PPIX, ZPPIX, uroporphyrin I, coproporphyrin I, and/or 5-ALA. In certain such embodiments, the accumulation of the one or more heme intermediates is inhibited in a dose dependent manner.

In certain embodiments, the GlyT1 inhibitor demonstrates an EC50 of less than 500 nM. In certain embodiments, the GlyT1 inhibitor demonstrates an EC50 of less than 100 nM.

In certain embodiments, at least 50% cell viability is maintained. In certain embodiments, at least 90% cell viability is maintained.

In certain embodiments, the subject has PPIX levels that are at least 10%, 20%, 30%, 40%, or 50% more than PPIX levels in a healthy subject prior to administration of the GlyT1 inhibitor.

In certain embodiments, the subject has ZPPIX levels that are at least 10%, 20%, 30%, 40%, or 50% more than ZPPIX levels in a healthy subject prior to administration of the GlyT1 inhibitor.

In certain embodiments, the subject has increased proportion of ZPPIX to free-protoporphyrin IX (ZPPIX/PPIX ratio) as compared to those with EPP.

In certain embodiments, the subject has uroporphyrin I and/or coproporphyrin I levels that are at least 10%, 20%, 30%, 40%, or 50% more than uroporphyrin I and/or coproporphyrin I levels in a healthy subject prior to administration of the GlyT1 inhibitor.

In certain embodiments, the subject has 5-ALA levels that are at least 10%, 20%, 30%, 40%, or 50% more than 5-ALA levels in a healthy subject prior to administration of the GlyT1 inhibitor.

In certain embodiments, the subject's PPIX levels decrease while the patient's heme levels are substantially maintained. In certain embodiments, the patient's PPIX levels decrease by at least 50% (e.g., 50%, 55%, 60%, 65%, 70%, 75%, 80%, 85%, 90%, 95%, or at least 100%) and the patient's heme levels decrease no more than 10% (e.g., 10%, 15%, 20%, 25%, and 30%). In certain embodiments, the patient's PPIX levels decrease by at least 85% and the patient's heme levels decrease no more than 15%. In certain embodiments, heme levels decrease no more than 10% (e.g., 10%, 15%, 20%, 25%, and 30%). In certain embodiments, the dosage of the pharmaceutical composition does not cause a substantial reduction in heme levels.

In certain embodiments, the subject has increased free-protoporphyrin IX levels in erythrocytes. In certain embodiments, the method decreases free-protoporphyrin IX levels in the subject. In certain such embodiments, the method decreases free-protoporphyrin IX levels in the subject by at least 10% (e.g., 10%, 15%, 20%, 25%, 30%, 35%, 40%, 45%, 50%, 55%, 60%, 65%, 70%, 75%, 80%, 85%, 90%, 95%, or at least 100%). In certain embodiments, the subject has increased protoporphyrin IX levels in the stool. In certain embodiments, the method decreases protoporphyrin IX levels in the stool of the subject. In certain such embodiments, the method decreases protoporphyrin IX levels in the stool of the subject by at least 10% (e.g., 10%, 15%, 20%, 25%, 30%, 35%, 40%, 45%, 50%, 55%, 60%, 65%, 70%, 75%, 80%, 85%, 90%, 95%, or at least 100%).

In certain embodiments, the subject's plasma porphyrin fluoresces at a peak of 634 nm when illuminated with blue light (e.g., 400-420 nm light). In certain embodiments, the subject's plasma porphyrin fluoresces at a peak between 626 nm and 634 nm when illuminated with blue light (e.g., 400-420 nm light). In certain embodiments, the subject's skin porphyrin fluoresces at a peak of 632 nm when illuminated with blue light (e.g., 400-420 nm light). In certain embodiments, the subject's skin porphyrin fluoresces at a peak between 626 nm and 634 nm when illuminated with blue light (e.g., 400-420 nm light).

In certain embodiments, the subject has increased protoporphyrin IX levels in the skin. In certain embodiments, the method decreases protoporphyrin IX levels in the skin of the subject. In certain such embodiments, the method decreases protoporphyrin IX levels in the skin of the subject by at least 10% (e.g., 10%, 15%, 20%, 25%, 30%, 35%, 40%, 45%, 50%, 55%, 60%, 65%, 70%, 75%, 80%, 85%, 90%, 95%, or at least 100%). In certain embodiments, the subject has greater than 0.2 FluoDerm Units (FDU) of protoporphyrin IX levels in the skin. In certain embodiments, the subject has greater than 1.0 FDU of protoporphyrin IX levels in the skin. In certain embodiments, the subject has between 1.0 FDU and 2.5 FDU of protoporphyrin IX levels in the skin. In certain embodiments, the subject has greater than 2.5 FDU of protoporphyrin IX levels in the skin. In certain embodiments, the method decreases protoporphyrin IX levels in the skin of the subject to less than 0.5 FDU. In certain embodiments, the method decreases protoporphyrin IX levels in the skin of the subject to less than 1.0 FDU. In certain embodiments, the method decreases protoporphyrin IX levels in the skin of the subject to less than 1.5 FDU. In certain embodiments, the method decreases protoporphyrin IX levels in the skin of the subject to less than 2.0 FDU. In certain embodiments, the method decreases protoporphyrin IX levels in the skin of the subject to less than 2.5 FDU.

In certain embodiments, the subject has increased protoporphyrin IX levels in the erythrocytes. In certain embodiments, the method decreases protoporphyrin IX levels in the erythrocytes of the subject. In certain such embodiments, the method decreases protoporphyrin IX levels in the erythrocytes of the subject by at least 10% (e.g., 10%, 15%, 20%, 25%, 30%, 35%, 40%, 45%, 50%, 55%, 60%, 65%, 70%, 75%, 80%, 85%, 90%, 95%, or at least 100%). In certain embodiments, the subject has greater than 31 $\mu mol\ L^{-1}$ protoporphyrin IX levels in the erythrocytes. In certain embodiments, the subject has between 31 $\mu mol\ L^{-1}$ and 53 $\mu mol\ L^{-1}$ protoporphyrin IX levels in the erythrocytes. In certain embodiments, the subject has greater than 53 $\mu mol\ L^{-1}$ protoporphyrin IX levels in the erythrocytes. In certain embodiments, the method decreases protoporphyrin IX levels in the erythrocytes of the subject to levels less than 53 $\mu mol\ L^{-1}$. In certain embodiments, the method decreases protoporphyrin IX levels in the erythrocytes of the subject to levels less than 31 $\mu mol\ L^{-1}$. In certain embodiments, the method decreases protoporphyrin IX levels in the erythrocytes of the subject to levels less than 15 $\mu mol\ L^{-1}$.

In certain embodiments, the subject's ferrochelatase activity level is reduced to between 10 to 35% of the ferrocheletase activity level observed in normal subjects. In certain embodiments, the subject's ferrochelatase activity level is reduced to less than 50% of the ferrocheletase activity level observed in normal subjects.

In certain embodiments, the subject has a gain-of-function mutation in ALAS2. In certain embodiments, the subject's ALAS2 enzyme activity is increased.

In certain embodiments, the subject has increased zinc-protoporphyrin IX levels in erythrocytes. In certain embodiments, the method decreases zinc-protoporphyrin IX levels in the subject's erythrocytes. In certain such embodiments, the method decreases zinc-protoporphyrin IX levels in the subject's erythrocytes by at least 10% (e.g., 10%, 15%, 20%, 25%, 30%, 35%, 40%, 45%, 50%, 55%, 60%, 65%, 70%, 75%, 80%, 85%, 90%, 95%, or at least 100%).

In certain embodiments, the subject has decreased activity of uroporphyrinogen III synthase. In certain embodiments, the subject has increased levels of uroporphyrin I and/or coproporphyrin I. In certain embodiments, the increased levels of uroporphyrin I and/or coproporphyrin I are measured in the subject's urine or red blood cells. In certain embodiments, the increased levels of coproporphyrin I are measured in the subject's stool. In certain embodiments, the method decreases the subject's levels of uroporphyrin I and/or coproporphyrin I. In certain embodiments, the method decreases the subject's levels of uroporphyrin I. In certain such embodiments, the method decreases the subject's levels of uroporphyrin I by at least 10% (e.g., 10%, 15%, 20%, 25%, 30%, 35%, 40%, 45%, 50%, 55%, 60%, 65%, 70%, 75%, 80%, 85%, 90%, 95%, or at least 100%). In certain embodiments, the method decreases the subject's levels of coproporphyrin I. In certain such embodiments, the method decreases the subject's levels of coproporphyrin I by at least 10% (e.g., 10%, 15%, 20%, 25%, 30%, 35%, 40%, 45%, 50%, 55%, 60%, 65%, 70%, 75%, 80%, 85%, 90%, 95%, or at least 100%).

In certain embodiments, the subject has a mutation in UROS.

In certain embodiments, the subject has a gene defect in GATA-1 erythroid-specific transcription factor.

In certain embodiments, the subject has red fluorescent urine. In certain embodiments, the subject has a peak between 615 nm and 620 nm using plasma porphyrin fluorescence analysis.

In certain embodiments, the subject has liver disease associated with EPP, XLPP, or CEP. In certain embodiments, the liver disease associated with EPP, XLPP, or CEP is cholelithiasis. In certain embodiments, the liver disease associated with EPP, XLPP, or CEP is mild liver disease. In certain embodiments, the liver disease associated with EPP, XLPP, or CEP is deteriorating liver disease. In certain embodiments, the liver disease associated with EPP, XLPP, or CEP is terminal phase liver disease.

In certain embodiments, the method further comprises administering to the subject an additional active agent and/or supportive therapy. In certain such embodiments, the additional active agent and/or supportive therapy is selected from the group consisting of avoiding sunlight, topical sunscreens, skin protection, UVB phototherapy, Afamelanotide (Scenesse®), bortezomib, proteasome inhibitors, chemical chaperones, cholestyramine, activated charcoal, iron supplementation, liver transplantation, bone marrow transplantation, splenectomy, and blood transfusion.

In certain embodiments, the GlyT1 inhibitor is a compound having a formula of

Formula I

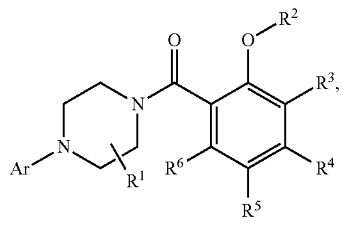

wherein Ar is unsubstituted or substituted aryl or 6-membered heteroaryl containing one, two or three nitrogen atoms, wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)$n-$(C_1-C_6)$-alkoxy, $(C_1-C_6)$-alkoxy substituted by halogen, $NR^7R^8$, $C(O)R^9$, SO2$R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl; $R^1$ is hydrogen or $(C_1-C_6)$-alkyl; $R^2$ is hydrogen, $(C_1-C_6)$-alkyl, $(C_2-C_6)$-alkenyl, $(C_1-C_6)$-alkyl substituted by halogen, $(C_1-C_6)$-alkyl substituted by hydroxy, (CH2)n-$(C_3-C_7)$-cycloalkyl optionally substituted by $(C_1-C_6)$-alkoxy or by halogen, $CH(CH_3)$—$(C_3-C_7)$-cycloalkyl, $(CH_2)_{n+1}$—C(O)—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy; $R^3$, $R^4$ and $R^6$ are each independently hydrogen, hydroxy, halogen, $(C_1-C_6)$-alkyl, $(C_1-C_6)$-alkoxy or O—$(C_3-C_6)$-cycloalkyl; $R^5$ is $NO_2$, CN, $C(O)R^9$ or $SO_2R^{10}$; $R^7$ and $R^8$ are each independently hydrogen or (C1-C6)-alkyl; $R^9$ is hydrogen, $(C_1-C_6)$-alkyl, $(C_1-C_6)$-alkoxy or $NR^7R^8$; $R^{10}$ is $(C_1-C_6)$-alkyl optionally substituted by halogen, $(CH_2)_n$—$(C_3-C_6)$-cycloalkyl, $(CH_2)_n$—$(C_3-C_6)$-alkoxy, $(CH_2)_n$-heterocycloalkyl or $NR^7R^8$; n is 0, 1, or 2; or a pharmaceutically acceptable salt thereof, or a prodrug of the compound or its pharmaceutically acceptable salt.

In certain embodiments, GlyT1 inhibitor is a compound having a formula of

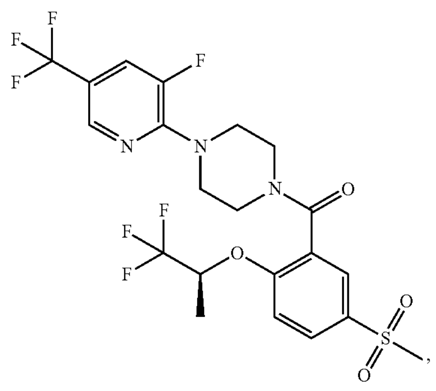 [SMILES: C[C@H](Oc1ccc(S(C)(=O)=O)cc1C(=O)N1CCN(c2ncc(C(F)(F)F)cc2F)CC1)C(F)(F)F]

bitopertin, or a pharmaceutically acceptable salt thereof, or a prodrug of the compound or its pharmaceutically acceptable salt.

In certain embodiments, the GlyT1 inhibitor is a compound having a formula of

Formula II

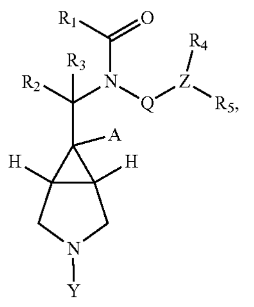

wherein $R_1$ represents a heteroaryl selected from the group consisting of: imidazolyl, thiazolyl, pyridyl, oxazolyl, pyrazolyl, triazolyl, oxadiazolyl, quinolinyl, isoxazolyl, pyrroloimidazoyl, and thiadiazole, wherein said heteroaryl is optionally substituted by one or more substituents selected from —OH, —$NR_7R_8$, halogen, $(C_1\text{-}C_8)$alkyl, $(C_3\text{-}C_{10})$cycloalkyl, $(C_1\text{-}C_8)$alkoxy, $(C_1\text{-}C_{12})$alkoxyalkyl, $(C_1\text{-}C_8)$hydroxyalkyl, $(C_6\text{-}C_{14})$aryl and benzyl; $R_2$, $R_3$ and A independently represent H or $(C_1\text{-}C_8)$alkoxy, wherein said alkyl is optionally substituted by one or more —OH, $(C_1\text{-}C_8)$alkoxy, —$NR_7R_8$ or halogen; Q represents —$(CH_2)_n$—, where n=1, 2, 3 or 4 or —$(CH_2)_m$—O—, where m=2, 3 or 4; Z represents $(C_6\text{-}C_{14})$aryl, $(C_1\text{-}C_8)$alkyl or $(C_3\text{-}C_8)$cycloalkyl; $R_4$ and $R_5$ each independently represent H, halogen, $(C_1\text{-}C_8)$alkyl, $(C_6\text{-}C_{14})$aryl, $(C_6\text{-}C_{14})$aryloxy, $(C_1\text{-}C_8)$alkoxy, (3-10 membered)heterocycloalkyl or $(C_3\text{-}C_8)$cycloalkoxy; wherein $R_4$ and $R_5$ are optionally substituted by one or more —OH, $(C_1\text{-}C_8)$alkoxy, —$NR_7R_8$ or halogen; Y represents —$R_6$, —$(CH_2)$o-$R_6$, —$C(R_6)_3$ or —$CH(R_6)_2$, wherein 0=1, 2 or 3; $R_6$ represents H, $(C_6\text{-}C_{14})$aryl, $(C_{1\text{-}10})$alkyl, $(C_3\text{-}C_{10})$cycloalkyl, $(C_5\text{-}C_{18})$bicycloalkyl, $(C_5\text{-}C_{18})$tricycloalkyl, (3-10 membered)heterocycloalkyl, (5-10 membered)heteroaryl, —C(═O)$NR_7R_8$, or —C(═O)$OR_7$, wherein said $R_6$ groups can optionally be substituted with one or more X groups; wherein X═—OH, $(C_1\text{-}C_8)$alkoxy, —$NR_{11}R_{12}$, —$SO_2R_{10}$, —C(═O)$R_{10}$, halogen, cyano, $(C_1\text{-}C_8)$alkyl, $(C_1\text{-}C_{10})$alkoxyalkyl, (5-10 membered)heteroaryl, $(C_6\text{-}C_{14})$aryl, $(C_6\text{-}C_{14})$aryloxy, benzyl, or $(C_1\text{-}C_8)$hydroxyalkyl; wherein $R_7$ and $R_8$ independently represent H, $(C_1\text{-}C_8)$alkyl, $(C_3\text{-}C8)$cycloalkyl, (5-10 membered)heterocycloalkyl, $(C_1\text{-}C_8)$hydroxyalky, (5-10 membered)heteroaryl or $(C_1\text{-}C_{10})$alkoxyalkyl; wherein $R_7$ and $R_8$ may optionally be substituted by one or more X groups; or $R_7$ and $R_8$ together with the nitrogen in which they may be attached may form a (3-10 membered)heterocycloalkyl group optionally substituted by one or more X groups; wherein $R_{10}$ represents $(C_1\text{-}C_8)$alkyl, $(C_3\text{-}C_8)$cycloalkyl, (3-10 membered)heterocycloalkyl, $(C_1\text{-}C_8)$hydroxyalky, (5-10 membered)heteroaryl or $(C_1\text{-}C_{10})$alkoxyalkyl; wherein $R_{11}$ and $R_{12}$ independently represent H, $(C_1\text{-}C_8)$alkyl, $(C_3\text{-}C_8)$cycloalkyl, (5-10 membered)heterocycloalkyl, $(C_1\text{-}C_8)$hydroxyalky, (5-10 membered)heteroaryl or $(C_1\text{-}C_{10})$alkoxyalkyl; or a pharmaceutically acceptable salt thereof, or a prodrug of the compound or its pharmaceutically acceptable salt. In certain such embodiments, the GlyT1 inhibitor is a compound having a formula of

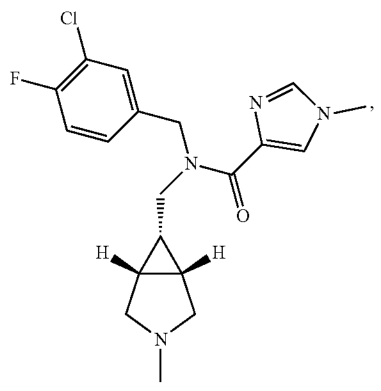 [SMILES: CN1C[C@@H]2[C@H](C1)[C@@H]2CN(Cc1ccc(F)c(Cl)c1)C(=O)c1cn(C)cn1]

or a pharmaceutically acceptable salt thereof, or a prodrug of the compound or its pharmaceutically acceptable salt. In other such embodiments, the GlyT1 inhibitor is a compound having a formula

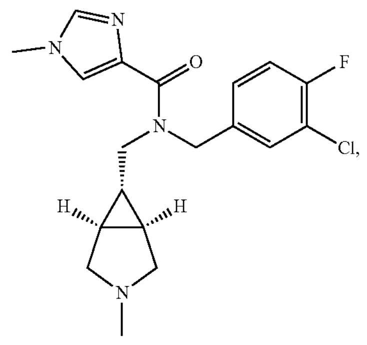 [SMILES: CN1C[C@@H]2[C@H](C1)[C@H]2CN(Cc1ccc(F)c(Cl)c1)C(=O)c1cn(C)cn1]

PF-3463275, or a pharmaceutically acceptable salt thereof, or a prodrug of the compound or its pharmaceutically acceptable salt.

In certain embodiments, the GlyT1 inhibitor is a compound having a formula of

Formula III

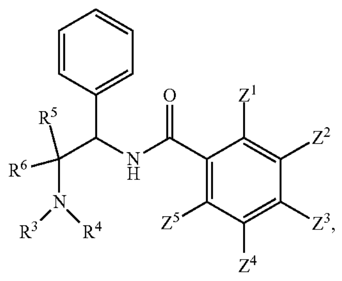

wherein $Z^1$ is selected from the group consisting of $C_{1\text{-}4}$alkyl, $C_{3\text{-}6}$CycloalkVI, $C_{1\text{-}4}$alkoxy, $C_{1\text{-}4}$alkylthio, halo$C_{1\text{-}4}$alkyl, phenyl, halo$C_{1\text{-}4}$alkoxy, halophenyl, $C_{1\text{-}4}$alkylsulfoxy, $C_{1\text{-}4}$alkylsulfonyl, bromo and chloro; $Z^2$ is selected from the group consisting of hydrogen, halogen, cyano, $C_{1\text{-}4}$alkyl, phenyl, halo$C_{1\text{-}4}$alkyl, halo$C_{1\text{-}4}$alkoxy, halophenyl, $C_{1\text{-}4}$alkoxy$C_{1\text{-}4}$alkyl and $C_{3\text{-}6}$cycloalkyl; $Z^3$ is selected from the group consisting of hydrogen, halogen, $C_{1\text{-}4}$alkyl, $C_{1\text{-}4}$alkoxy, $C_{1\text{-}4}$alkylthio, halo$C_{1\text{-}4}$alkyl, halo$C_{1\text{-}4}$alkoxy, and $C_{3\text{-}6}$cycloalkyl; $Z^4$ is selected from the group consisting of hydrogen, halogen, $C_{1\text{-}3}$alkyl, halo$C_{1\text{-}4}$alkyl, $C_{1\text{-}4}$alkoxy, $C_{1-4}$alkylthio, phenyl, halo$C_{1-4}$alkoxy, halophenyl, $C_{1-4}$alkoxy$C_{1-4}$alkyl and $C_3$-6cycloalkyl; $Z^5$ is selected from the group consisting of hydrogen, fluoro, chloro, bromo, iodo, hydroxy, $C_{1-4}$alkyl, $C_{1-4}$alkoxy, $C_{1-4}$alkylthio, phenyl, halo$C_{1-4}$alkyl, halo$C_{1-4}$alkoxy, halophenyl, $C_{1-4}$alkoxy$C_{1-4}$alkyl and $C_{3-6}$cycloalkyl; whereby if more than one of $Z^1$ to $Z^5$ is methoxy, then only $Z^1$ and $Z^5$ are methoxy $R^3$ and $R^4$ are independently selected from hydrogen and $C_{1-4}$alkyl, optionally substituted with one or more groups Y; or $R^3$ and R4 together with the nitrogen atom to which they are attached form a saturated or partially unsaturated A-, 5-6- or 7-membered carbocyclic ring optionally substituted with a group Y'; Y is selected from the group consisting of $C_{1-4}$alkoxy, hydroxy, halo$C_{1-4}$alkoxy and $C_{3-5}$cycloalkyl; Y' is selected from the group consisting of $C_{1-4}$alkyl, $C_{1-4}$alkoxy, halogen, hydroxy, halo$C_{1-4}$alkoxy, $C_{3-5}$cycloalkyl and $C_{5-10}$aryl or Y' forms a —CH2- or —CH2-CH2- bridge between two atoms on the A-, 5-, 6- or 7-membered carbocyclic ring; $R^5$ and $R^6$ are independently $C_{1-4}$alkyl, optionally substituted with one or more groups X; or $R^5$ and $R^6$ together with the carbon atom to which they are attached form a saturated 5- or 6-membered ring carbocyclic optionally substituted with one or more groups X', in the case of $R^5$ and $R^6$ together with the carbon atom to which they are attached forming a 5-membered saturated carbocyclic ring, that ring may optionally further comprising an additional heteroatom group selected from O, N and S(O)m, where m=0, 1 or 2; X is selected from the group consisting of halogen, hydroxy, $C_{1-4}$alkoxy, halo$C_{1-4}$alkyl, halo$C_{1-4}$ alkoxy and $C_{5-10}$aryl; and X' is selected from the group consisting of halogen, hydroxy, $C_{1-4}$alkyl, $C_{1-4}$alkoxy, halo$C_{1-4}$alkyl, halo$C_{1-4}$alkoxy and $C_{5-10}$aryl; whereby $R^3$, $R^4$, $R^5$ and $R^6$ are not all simultaneously unsubstituted methyl; with the provisos that when simultaneously $Z^1$ is propyloxy, $Z^3$ is chloro, $Z^2$═$Z^4$═$Z^5$═H, and $R^5$ and $R^6$ are both methyl, then $R^3$ and $R^4$ together with the nitrogen atom to which they are attached do not form a 2-methylpyrrolidine group; when simultaneously $Z^1$ is methyl, $Z^3$ is methoxy, $Z^2$═Z4=Z5=H, and $R^5$ and $R^6$ are both methyl, then $R^3$ and $R^4$ together with the nitrogen atom to which they are attached do not form a pyrrolidine group, or a pharmaceutically acceptable salt thereof, or a prodrug of the compound or its pharmaceutically acceptable salt. In certain such embodiments, the GlyT1 inhibitor is a compound having a formula of

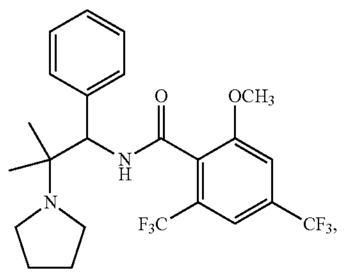 [SMILES: COc1cc(C(F)(F)F)cc(C(F)(F)F)c1C(=O)NC(c1ccccc1)C(C)(C)N1CCCC1]

or a pharmaceutically acceptable salt thereof, or a prodrug of the compound or its pharmaceutically acceptable salt.

In certain embodiments, the GlyT1 inhibitor is a compound having a formula of

Formula IV

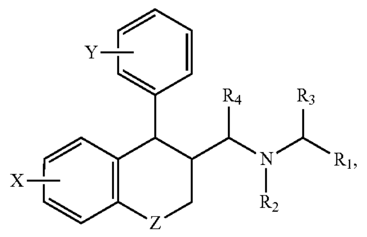

wherein Z is $(CH_2)_n$, O, S, SO, $SO_2$ or N—$R_5$; n is 0, 1 or 2; X represents 1-3 substituents independently selected from hydrogen, halogen, $(C_{1-6})$alkyioxy, $(C_{3-6})$cycloalkyloxy, $(C_{6-12})$aryloxy, $(C_{6-12})$aryl, thienyl, $SR_6$, $SOR_6$, $SO_2R_6$, $NR_6R_6$, $NHR_6$, $NH_2$, $NHCOR_6$, $NSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together represent a fused $(C_{5-6})$aryl group, a fused $(C_{5-6})$cycloalkyl ring or O—$(CH_2)_m$—O; m is 1 or 2; Y represents 1-3 substituents independently selected from hydrogen, halogen, $(C_{1-4})$alkyloxy, $SR_6$, $NR_6R_6$ and $(C_{1-4})$ alkyl, optionally substituted with halogen; $R_1$ is $COOR_7$ or $CONR_8R_9$; $R_2$ and R6 are $(C_{1-4})$alkyl; $R_3$, $R_4$ are $R_5$ are independently hydrogen or $(C_{1-4})$alkyl; $R_7$, $R_8$ and $R_9$ are independently hydrogen, $(C_{1-4})$alkyl, $(C_{6-12})$aryl or arylalkyl, or a pharmaceutically acceptable salt thereof, or a prodrug of the compound or its pharmaceutically acceptable salt. In certain such embodiments, the GlyT1 inhibitor is a compound having a formula of

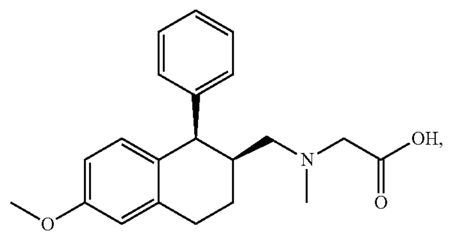 [SMILES: COc1ccc2c(c1)CC[C@H](CN(C)CC(=O)O)[C@@H]2c1ccccc1]

or a pharmaceutically acceptable salt thereof, or a prodrug of the compound or its pharmaceutically acceptable salt.

In certain embodiments, the GlyT1 inhibitor is a compound having a formula of

Formula V

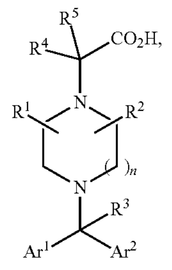

wherein n is an integer from 1 to 3; $R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^o$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$-alkylene chain wherein one of the carbon atoms in the alkylene chain is optionally replaced by a —NR—, —O—, —S(O)n- (where R is hydrogen or alkyl and n is 0-2) and further wherein one or two hydrogen atoms in the alkylene chain can be optionally substituted with one or two alkyl; $R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C═C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring-in $R^g$, $R^h$ and $R^i$ is optionally substituted with $R^j$, $R^k$, or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula V is not 2-(4-benzhydrylpiperazin-1-yl)acetic acid, 2-(4-((4-chlorophenyl)(phenyl)methyl)piperazin-1-yl)acetic acid, 2-((2R,5S)-4-((R)-(4-(1H-tetrazol-5-yl)phenyl)(3-hydroxyphenyl)methyl)-2,5-dimethylpiperazin-1-yl)acetic acid, or 2-((2R,5S)-4-((R)-(4-cyanophenyl)(3-hydroxyphenyl)methyl)-2,5-dimethylpiperazin-1-yl)acetic acid, or a pharmaceutically acceptable salt thereof, or a prodrug of the compound or its pharmaceutically acceptable salt. In certain such embodiments, the GlyT1 inhibitor is a compound having a formula of

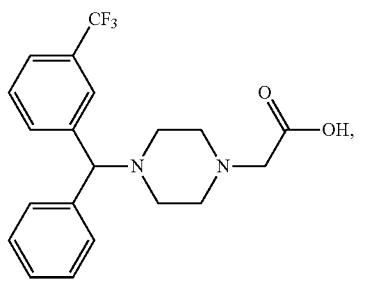 [SMILES: O=C(O)CN1CCN(C(c2ccccc2)c2cccc(C(F)(F)F)c2)CC1]

or a pharmaceutically acceptable salt thereof, or a prodrug of the compound or its pharmaceutically acceptable salt.

In certain embodiments, the GlyT1 inhibitor is a compound having a formula of

Formula VI

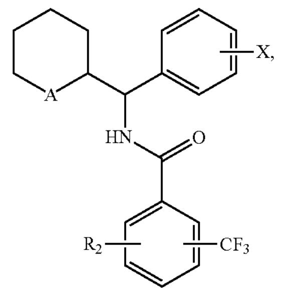

wherein A represents a group of general formula N—$R_1$, a group of general formula N+(O—)$R_1$ or a group of general formula N+(R')$R_1$, and in which $R_1$ represents either a hydrogen atom, or a linear or branched ($C_1$-$C_7$)alkyl group optionally substituted with one or more fluorine atoms, or a ($C_4$-$C_7$)cycloalkyl group, or a ($C_3$-$C_7$)cycloalkyl($C_1$-$C_3$)alkyl group, or a phenyl($C_1$-$C_3$)alkyl group optionally substituted with one or two hydroxyl or methoxy groups, or a ($C_2$-$C_4$)alkenyl group, or a ($C_2$-$C_4$)alkynyl group; R' represents a linear or branched ($C_1$-$C_7$)alkyl group; X represents a hydrogen atom or one or more substituents chosen from halogen atoms and trifluoromethyl, linear or branched (C1-C4)alkyl and ($C_1$-$C_4$)alkoxy groups; $R_2$ represents either a hydrogen atom, or one or more substituents chosen from halogen atoms and trifluoromethyl, ($C_1$-$C_4$)alkyl or ($C_1$-$C_4$) alkoxy groups, or amino groups of general formula $NR_3R_4$ in which $R_3$ and $R_4$ each represent, independently of each other, a hydrogen atom or a ($C_1$-$C_4$)alkyl group, or form with the nitrogen atom carrying them a pyrrolidine, piperidine or morpholine ring, or a phenyl group optionally substituted with an atom or a group as defined for the symbol X above, or a pharmaceutically acceptable salt thereof, or a prodrug of the compound or its pharmaceutically acceptable salt. In certain such embodiments, the GlyT1 inhibitor is a compound having a formula of

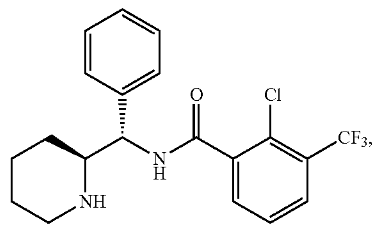 [SMILES: O=C(N[C@@H](c1ccccc1)[C@@H]1CCCCN1)c1cccc(C(F)(F)F)c1Cl]

or a pharmaceutically acceptable salt thereof, or a prodrug of the compound or its pharmaceutically acceptable salt.

In certain embodiments, the GlyT1 inhibitor is a compound having a formula of

Formula VII

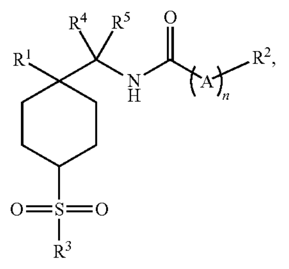

wherein $R^1$ is —$(CH_2)_n$—$R^{1a}$, wherein n is independently 0-6, and $R^{1a}$ is selected from the group consisting of: (1) $C_{1-6}$alkyl, which is unsubstituted or substituted with 1-6 halogen, hydroxy, (2) phenyl substituted with $R^{2a}$, $R^{2b}$ and $R^{2c}$, (3) $C_{3-6}$cycloallyl, which is unsubstituted or substituted with $C_{1-6}$alkyl, 1-6 halogen, hydroxy or —$NR^{10}R^{11}$, (4) —O—$C_{1-6}$alkyl, which is unsubstituted or substituted with 1-6 halogen, hydroxy or —$NR^{10}R^{11}$, (5) —CO2$R^9$, wherein R9 is independently selected from: (a) hydrogen, (b) —$C_{1-6}$alkyl, which is unsubstituted or substituted with 1-6 fluoro, (c) benzyl, and (d) phenyl, (6) —$NR^{10}R^{11}$, wherein $R^{10}$ and $R^{11}$ are independently selected from: (a) hydrogen, (b) —$C_{1-6}$alkyl, which is unsubstituted or substituted with hydroxy, 1-6 fluoro or —$NR^{12}R^{13}$, where $R^{12}$ and $R^{13}$ are independently selected from hydrogen and —$C_{1-6}$alkyl, (c) —$C_{3-6}$cycloalkyl, which is unsubstituted or substituted with hydroxy, 1-6 fluoro or —$NR^{12}R^{13}$, (d) benzyl, (e) phenyl, and (7) —$CONR^{10}R^{11}$; R2 is selected from the group consisting of: (1) phenyl, which is substituted with $R^{2a}$, $R^{2b}$ and $R^{2c}$, (2) —$C_{1-8}$alkyl, which is unsubstituted or substituted with 1-6 halogen, hydroxy, —$NR^{10}R^{11}$, phenyl or heterocycle, where the phenyl or heterocycle is substituted with $R^{2a}$, $R^{2b}$ and $R^{2c}$, (3) $C_{3-6}$cycloalkyl, which is unsubstituted or substituted with 1-6 halogen, hydroxy or —$NR^{10}R^{11}$, and (4) —$C_{1-6}$alkyl-($C_{3-6}$cycloalkyl), which is unsubstituted or substituted with 1-6 halogen, hydroxy or —$NR^{10}R^{11}$; $R^{2a}$, $R^{2b}$ and $R^{2c}$ are independently selected from the group consisting of: (1) hydrogen, (2) halogen, (3) —$C_{1-6}$alkyl, which is unsubstituted or substituted with: (a) 1-6 halogen, (b) phenyl, (c) $C_{3-6}$cycloalkyl, or (d) —$NR^{10}R^{11}$, (4) —O—$C_{1-6}$alkyl, which is unsubstituted or substituted with 1-6 halogen, (5) hydroxy, (6) —$SCF_3$, (7) —$SCHF_2$, (8) —$SCH_3$, (9) —$CO_2R^9$, (10) —CN, (11) —$SO_2R^9$, (12) —$SO_2$—$NR^{10}R^{11}$, (13) —$NR^{10}R^{11}$, (14) —$CONR^{10}R^{11}$, and (15) —$NO_2$; $R^3$ is selected from the group consisting of: (1) $C_{1-6}$alkyl, which is unsubstituted or substituted with 1-6 halogen, hydroxyl, or —$NR^{10}R^{11}$, (2) $C_{3-6}$cycloalkyl, which is unsubstituted or substituted with 1-6 halogen, hydroxyl or —$NR^{10}R^{11}$, $R^4$ and $R^5$ are independently selected from the group consisting of: (1) hydrogen, and (2) $C_{1-6}$alkyl, which is unsubstituted or substituted with halogen or hydroxyl, or $R^4$ and $R^5$ taken together form a $C_{3-6}$cycloalkyl ring; A is selected from the group consisting of: (1) —O—, and (2) —$NR^{10}$—; m is zero or one, whereby when m is zero $R^2$ is attached directly to the carbonyl; and pharmaceutically acceptable salts thereof and individual enantiomers and diastereomers thereof, or a pharmaceutically acceptable salt thereof, or a prodrug of the compound or its pharmaceutically acceptable salt. In certain such embodiments, the GlyT1 inhibitor is a compound having a formula of

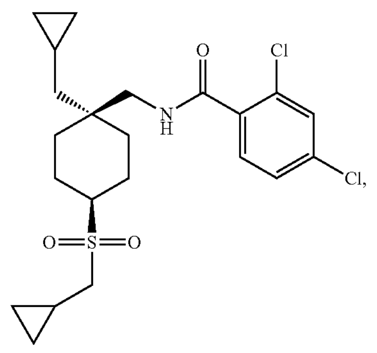 [SMILES: O=C(NC[C@]1(CC2CC2)CC[C@H](S(=O)(=O)CC2CC2)CC1)c1ccc(Cl)cc1Cl]

or a pharmaceutically acceptable salt thereof, or a prodrug of the compound or its pharmaceutically acceptable salt.

In certain embodiments, the GlyT1 inhibitor is a compound having a formula of

Formula VIII

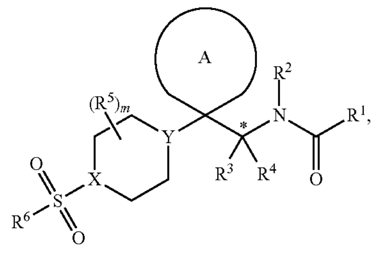

wherein $R^1$ is phenyl independently substituted from 1 to 5 times with halogen, $C_1$-$C_3$ alkyl, $C_3$-$C_6$ cycloalkyl, $OR^9$, or $SR^{10}$, wherein $C_1$-$C_3$ alkyl and $C_3$-$C_6$ cycloalkyl are optionally substituted with 1 to 10 times with $R^7$; $R^2$ is H; $R^3$ and R4 are each individually H or $CH_3$; $R^5$ is selected from the group consisting of: (1) hydrogen, (2) $C_1$-$C_6$ alkyl which is optionally substituted from 1 to 11 times with $R^7$, (3) gem-dialkyl, and (4) gem-dihalo; or two $R^5$ substituents on the same carbon, together with the carbon atom to which they are attached, may form a 3-, 4-, or 5-membered cycloalkyl optionally substituted from 1 to 10 times with $R^7$; or two $R^5$ substituents on adjacent carbons of the ring to which they are attached, together may form a 3-, 4-, 5- or 6-membered cycloalkyl optionally substituted from 1 to 10 times with $R^7$; $R^6$ is

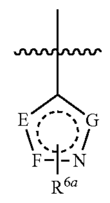

wherein E, F, and G are each independently nitrogen or carbon and $R^{6a}$ is $C_1$-$C_2$ alkyl, which is optionally substituted 1 to 5 times with halogen or deuterium; $R^7$ is selected from the group consisting of: (1) hydrogen, (2) halogen, (3) deuterium, (4) gem-dialkyl, (5) gem-dihalo, (6) —$OR^9$, —$NR^{11}R^{12}$, —$NR^{11}C(O)_pR^{10}$, —$S(O)_pR^{10}$, —CN, —NO2, —$C(O)_pR^{10}$, —$C(O)NR^{11}R^{12}$, or —$NR^{11}C(S)R^{10}$, and (7) oxo or thio; $R^8$ is selected from the group consisting of: (1)

hydrogen, (2) halogen, (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is independently and optionally substituted from 1 to 11 times with $R^7$, or (4) —$OR^9$, —$NR^{11}R^{12}$, —$NR^{11}C(O)_pR^{10}$, —$S(O)_pR^{10}$, —CN, —NO2, —$C(O)_pR^{10}$, —$C(O)NR^{11}R^{12}$, or —$NR^{11}C(S)R^{10}$; $R^9$ is selected from the group consisting of hydrogen, $C_1$-$C_4$ alkyl, $C_3$-$C_7$ cycloalkyl, $C_4$-$C_7$ cycloalkylalkyl, —$C(O)NR^{11}R^{12}$, and —$C(O)_pR^{10}$, wherein each of $C_1$-$C_4$ alkyl, $C_3$-$C_7$ cycloalkyl, and $C_4$-$C_7$ cycloalkylalkyl is optionally substituted from 1 to 11 times with $R^7$; $R^{10}$ is selected from the group consisting of hydrogen, $C_1$-$C_4$ alkyl, $C_3$-$C_7$ cycloalkyl $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$; $R^{11}$ and $R^{12}$ are each independently selected from the group consisting hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$, or $R^{11}$ and $R^{12}$ are taken together with the nitrogen to which they are attached to form a saturated or partially saturated monocyclic or fused bicyclic heterocycle optionally substituted from 1 to 11 times with $R^7$; A is

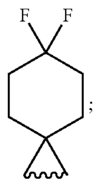

X is N; Y is N; p is 1, or 2; and m is 0; with the following provisos that: $R^6$ cannot be (a) 1H-1,2,3-triazol-4-yl, or (b) 5-methylisoxazol-4-yl; or an oxide thereof, a pharmaceutically acceptable salt of the compound or its oxide, or an individual enantiomer or diastereomer thereof.

In certain embodiments, the GlyT1 inhibitor is a compound having a formula of

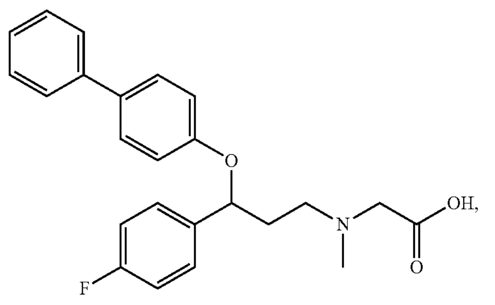

-continued

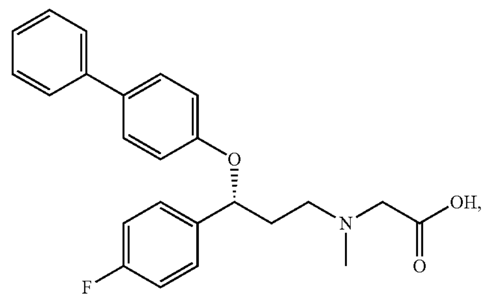

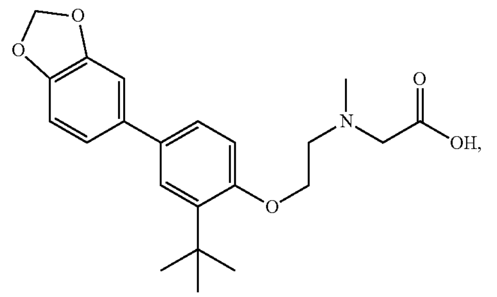

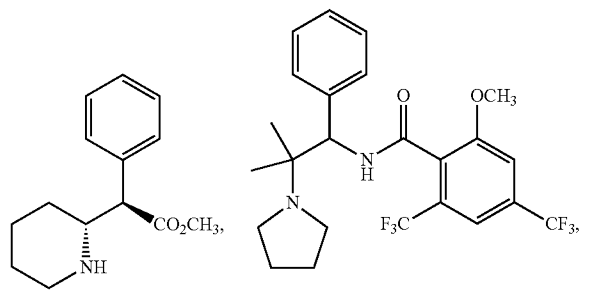

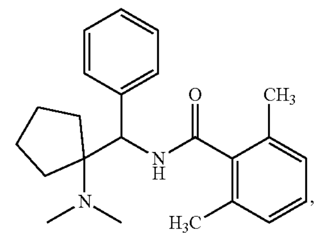

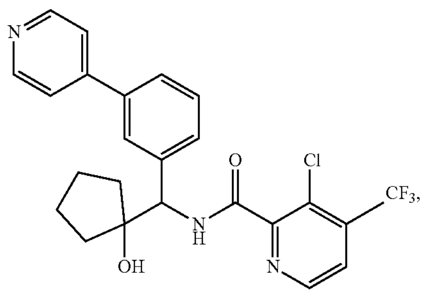

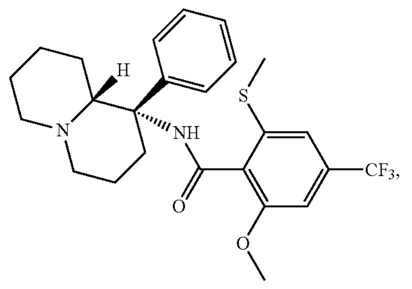

-continued
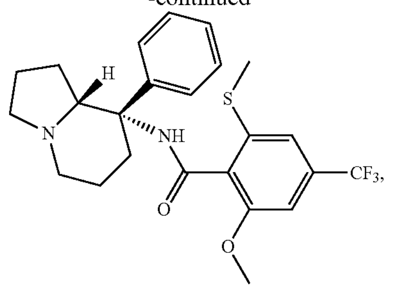
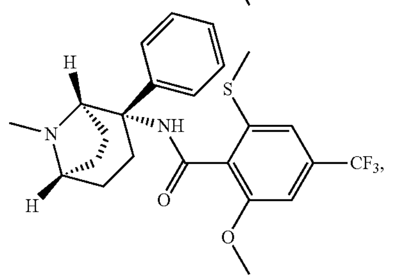
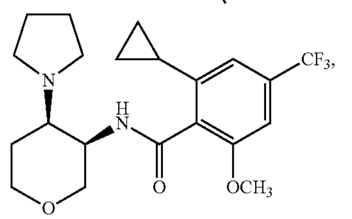
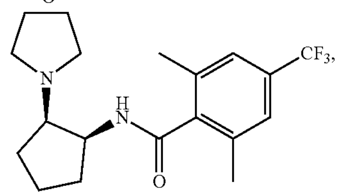
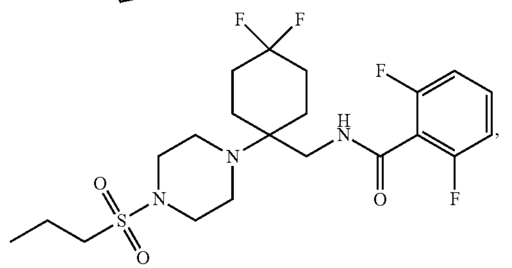
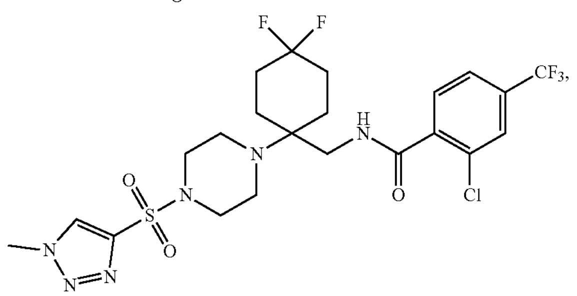
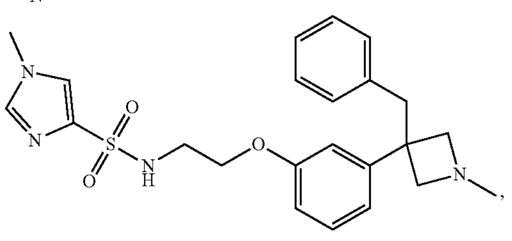
-continued
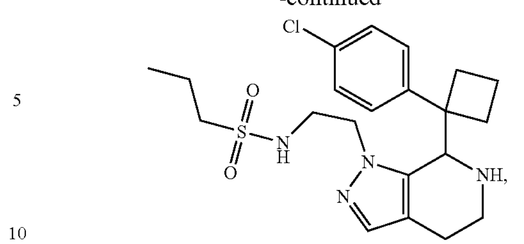
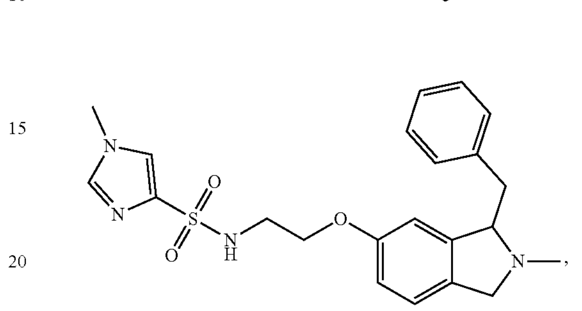
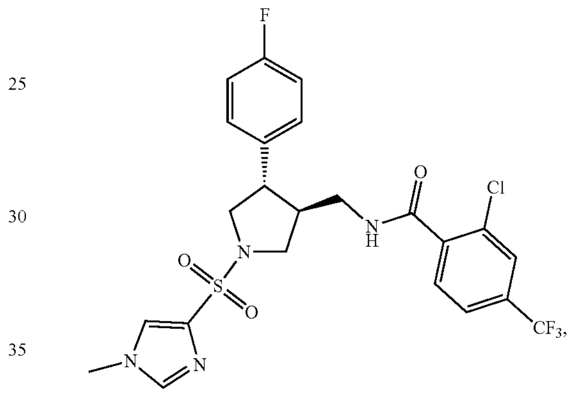
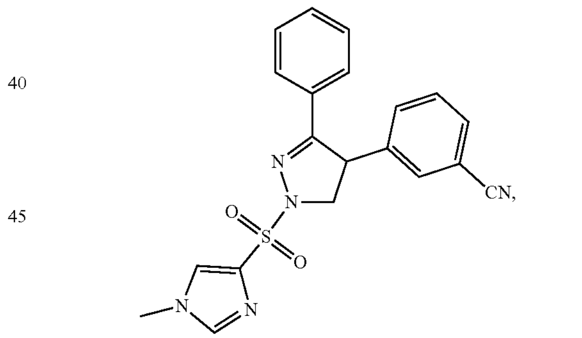
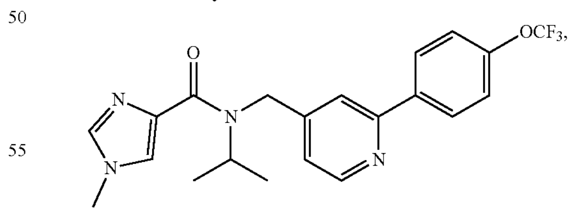
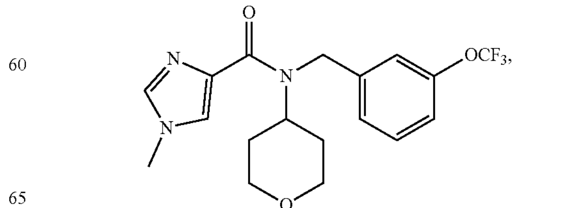
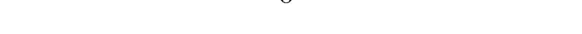

-continued
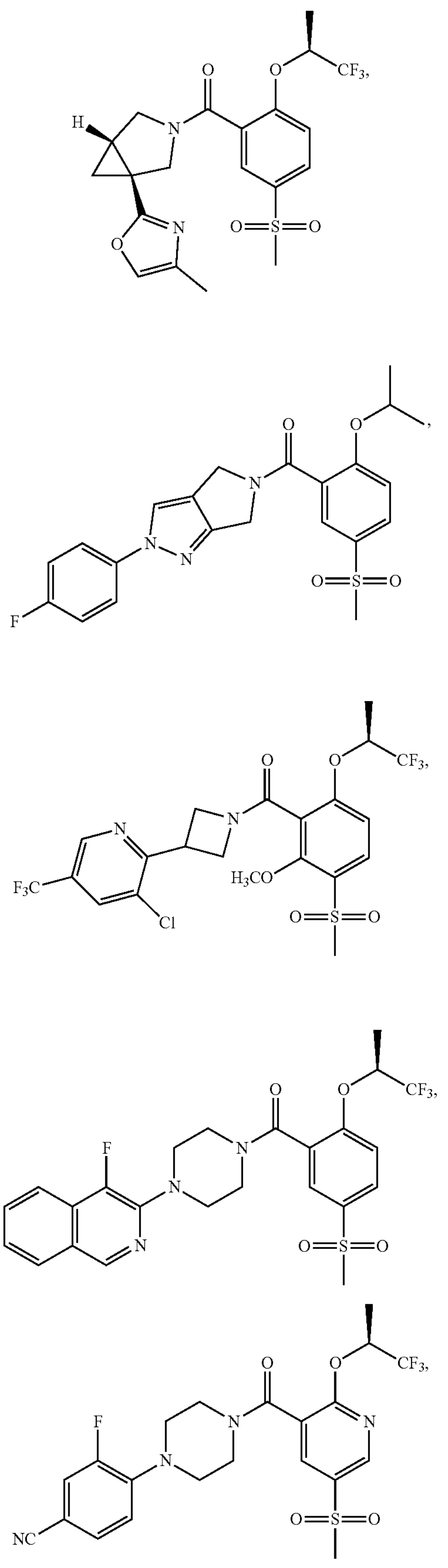
-continued
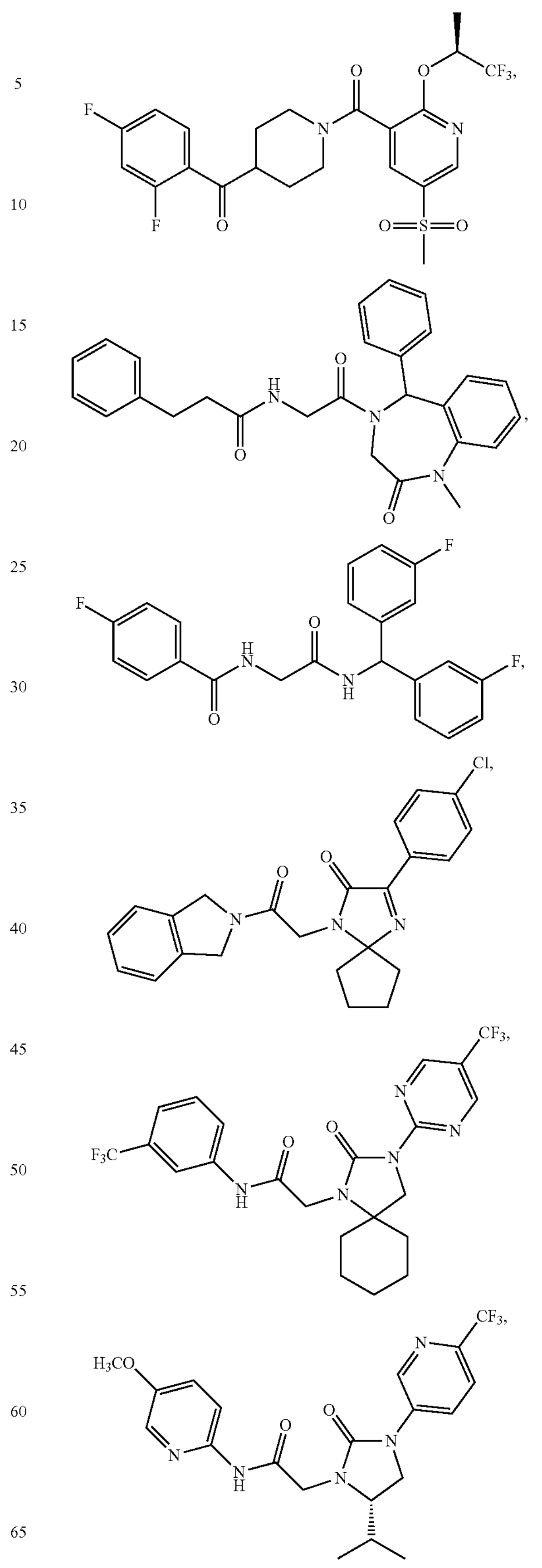

-continued

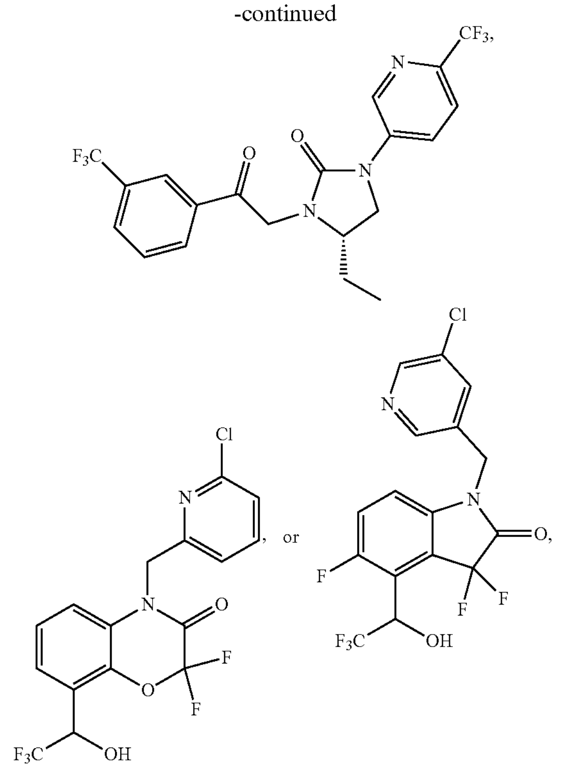

, or

, or a pharmaceutically acceptable salt thereof, or a prodrug of the compound or its pharmaceutically acceptable salt.

In certain embodiments, the GlyT1 inhibitor is a compound of formula IX,

Formula IX

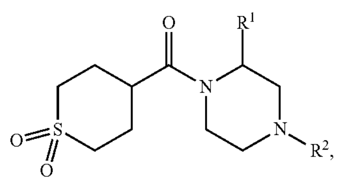

wherein $R^1$ represents phenyl or a 5 or 6 membered monocyclic heteroaryl having 1, 2, or 3 heteroatoms independently selected from O, N or S, wherein the phenyl or the heteroaryl is optionally substituted with one or more $R^3$; $R^2$ represents aryl, a 5 or 6 membered monocyclic heteroaryl or a 8 to 10 membered bicyclic heteroaryl, the mono- or bicyclic heteroaryl having 1, 2, or 3 heteroatoms independently selected from O, N or S, wherein the aryl or the heteroaryl is optionally substituted with one or more $R^4$; $R^3$ is a halogen, a $C_{1-4}$-alkyl or a $C_{3-6}$-cycloalkyl, wherein the $C_{1-4}$-alkyl or the $C_{3-6}$-cycloalkyl is optionally substituted with one or more halogens; and $R^4$ is a halogen, —CN, $C_{1-4}$-alkyl, $C_{3-6}$-cycloalkyl, —$C_{1-3}$-alkyl —$C_{3-6}$-cycloalkyl or —O—$C_{1-6}$ alkyl, wherein the $C_{1-4}$-alkyl, $C_{3-6}$-cycloalkyl, —$C_{1-3}$-alkyl —$C_{3-6}$-cycloalkyl or the —O—$C_{1-6}$-alkyl is optionally substituted with one or more halogens; or a pharmaceutically acceptable salt thereof, or a tautomer or stereoisomer of the compound or its pharmaceutically acceptable salt, or a mixture of any of the foregoing.

In certain embodiments, the GlyT1 inhibitor is a compound of formula X,

Formula X

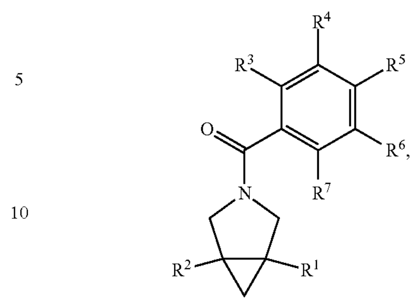

wherein $R^1$ is selected from the group consisting of a) 5 or 6 membered monocyclic heteroaryl, having 1, 2, 3 or 4 heteroatoms independently selected from the group consisting of O, N and S(O)r, b) 5 or 6 membered monocyclic partially saturated heterocycloalkyl, having 1, 2 or 3 heteroatoms independently selected from the group consisting of O, N and S(O)r, and c) 9 or 10 membered bicyclic heteroaryl, having 1, 2 or 3 heteroatoms independently selected from the group consisting of O, N and $S(O)_r$, wherein r is 0, 1 or 2; wherein each of said groups a), b) and c) is optionally substituted with 1 or more substituents independently selected from the group consisting of $C_{1-4}$-alkyl-, $C_{1-4}$-alkyl-O—, oxetanyl, tetrahydrofuranyl, tetrahydropyranyl, $C_{3-6}$-cycloalkyl- and $C_{3-6}$-cycloalkyl-O— and in case a substituent is attached to a nitrogen ring atom said substituent is selected from the group consisting of $C_{1-4}$-alkyl-, $C_{1-4}$-alkyl-CO—, $C_{3-6}$-cycloalkyl- and $C_{3-6}$-cycloalkyl-CO—, and wherein each of said $C_{1-4}$-alkyl-, $C_{1-4}$-alkyl-O—, $C_{1-4}$-alkyl-CO—, oxetanyl, tetrahydrofuranyl, tetrahydropyranyl, $C_{3-6}$-cycloalkyl-, $C_{3-6}$-cycloalkyl-CO— or $C_{3-6}$-cycloalkyl-O— substituents may be substituted by 1 or more substituents independently selected from the group consisting of fluoro, —$CF_3$, —$CHF_2$, —$CH_2F$ and —CN; $R^2$ is selected from the group consisting of hydrogen, $C_{1-4}$-alkyl-, $C_{1-4}$-alkyl-O—, —CN and $C_{3-6}$-cycloalkyl-, wherein each of said $C_{1-4}$-alkyl-, $C_{1-4}$-alkyl-O— and $C_{3-6}$-cycloalkyl-group may be optionally substituted with 1, 2, 3 or more substituents independently selected from the group consisting of fluoro, —$CF_3$, —$CHF_2$, —$CH_2F$ and —CN; $R^3$ is selected from the group consisting of $C_{1-6}$-alkyl-O—, $C_{3-6}$-cycloalkyl-O—, morpholino, pyrazolyl and a 4 to 7 membered, monocyclic heterocycloalkyl-O— with 1 oxygen atom as ring member and optionally 1 or 2 heteroatoms independently selected from the group consisting of O, N and $S(O)_s$ with s=0, 1 or 2, wherein said $C_{1-6}$-alkyl-O— and said $C_{3-6}$-cycloalkyl-O— may be optionally substituted with 1, 2, 3 or more substituents independently selected from the group consisting of fluoro, —$CF_3$, —$CHF_2$, —$CH_2F$, —CN, $C_{1-4}$-alkyl-, $C_{3-6}$-cycloalkyl-, $C_{1-6}$-alkyl-O— and $C_{3-6}$-cycloalkyl-O—; $R^4$ is hydrogen; or $R^3$ and $R^4$ together with the ring atoms of the phenyl group to which they are bound may form a 4, 5 or 6 membered, monocyclic, partially saturated heterocycloalkyl or a heteroaryl each of which having 1, 2 or 3 heteroatoms independently selected from the group consisting of O, N and $S(O)_s$ with s=0, 1 or 2, wherein there must be 1 ring oxygen atom that is directly attached to the ring carbon atom of said phenyl group to which $R^3$ is attached to in general formula (I); wherein said heterocycloalkyl group may be optionally substituted with 1, 2, 3 or more substituents independently selected from the group consisting of fluoro, —$CF_3$, —$CHF_2$, —$CH_2F$, —CN, $C_{1-4}$-alkyl-, $C_{3-6}$-cycloalkyl-, $C_{1-6}$-alkyl-O—, $C_{3-6}$-cycloalkyl- O—, oxetanyl-O—, tetrahydrofuranyl-O— and tetrahydropyranyl-O—; $R^5$ is hydrogen; $R^6$ is selected from the group consisting of hydrogen, $C_{1-4}$-alkyl-$SO_2$—, $C_{3-6}$-cycloalkyl-$SO_2$ and CN; $R^7$ is hydrogen; or one of the pairs a) $R^6$ and $R^7$ or b) $R^6$ and $R^5$ form together with the ring atoms of the phenyl group to which they are bound, a 5 or 6 membered, partially saturated monocyclic heterocycloalkyl group having 1, 2 or 3 heteroatoms independently selected from the group consisting of O, N and $S(O)_u$ with u=0, 1 or 2, wherein there must be 1 —$SO_2$— member that is directly attached to the ring carbon atom of said phenyl group to which $R^6$ is attached to in general formula (I), wherein said heterocycloalkyl group may be optionally substituted with 1, 2, 3 or more substituents independently selected from the group consisting of fluoro, —$CF_3$, —$CHF_2$, —$CH_2F$, —CN, $C_{1-4}$-alkyl-, $C_{1-6}$-alkyl-O— and $C_{3-6}$-cycloalkyl-O— or a pharmaceutically acceptable salt thereof.

In certain embodiments, the pharmaceutical composition further comprises a pharmaceutically acceptable carrier.

In certain embodiments, the subject is a subject in need thereof.

In certain embodiments, the GlyT1 inhibitor, or pharmaceutically acceptable salt thereof, or prodrug of the GlyT1 inhibitor or its pharmaceutically acceptable salt, is administered in a therapeutically effective amount.

DETAILED DESCRIPTION OF THE APPLICATION

Figure 1:
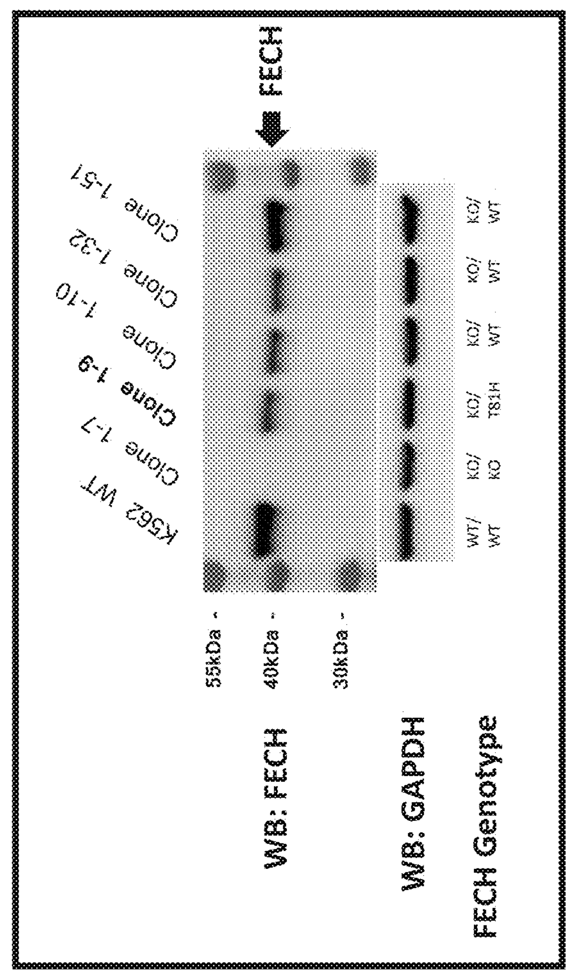
FIG. 1 shows western blot determination of ferrochelatase (FECH) protein expression levels for various K562 clones.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

The term "acyl" is art-recognized and refers to a group represented by the general formula hydrocarbylC(O)—, preferably alkylC(O)—.

As used herein, the term "acylamino" means an amino group substituted by an acyl group (e.g., —O—C(═O)—H or —O—C(═O)-alkyl). An example of an acylamino is —NHC(═O)H or —NHC(═O)$CH_3$. The term "lower acylamino" refers to an amino group substituted by a lower acyl group (e.g., —O—C(═O)—H or —O—C(═O)—$C_{1-6}$alkyl). An example of a lower acylamino is —NHC(═O)H or —NHC(═O)$CH_3$.

The term "acyloxy" is art-recognized and refers to a group represented by the general formula hydrocarbylC(O)O—, preferably alkylC(O)O—.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —$NHCH_2CH_3$.

As used herein, the term "alkylene" or "alkylenyl" means a divalent alkyl linking group. An example of an alkylene (or alkylenyl) is methylene or methylenyl (—$CH_2$—).

As used herein, the term "alkylthio" means an —S-alkyl group having from 1 to 6 carbon atoms. An example of an alkylthio group is $—SCH_2CH_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

The term "amide", as used herein, refers to a group

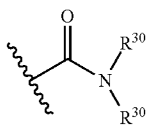

wherein each $R^{30}$ independently represent a hydrogen or hydrocarbyl group, or two $R^{30}$ are taken together with the N atom to which they are attached complete a heterocycle having from 4 to 8 atoms in the ring structure.

As used herein, the term "amidino" means —C(═NH)$NH_2$.

The terms "amine" and "amino" are art-recognized and refer to both unsubstituted and substituted amines and salts thereof, e.g., a moiety that can be represented by

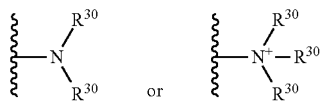

wherein each $R^{30}$ independently represents a hydrogen or a hydrocarbyl group, or two $R^{30}$ are taken together with the N atom to which they are attached complete a heterocycle having from 4 to 8 atoms in the ring structure.

As used herein, the term "aminoalkoxy" means an alkoxy group substituted by an amino group. An example of an aminoalkoxy is $—OCH_2CH_2NH_2$.

As used herein, the term "aminoalkyl" means an alkyl group substituted by an amino group. An example of an aminoalkyl is $—CH_2CH_2NH_2$.

As used herein, the term "aminosulfonyl" means $—S(═O)_2NH_2$.

As used herein, the term "aminoalkylthio" means an alkylthio group substituted by an amino group. An example of an aminoalkylthio is $—SCH_2CH_2NH_2$.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:

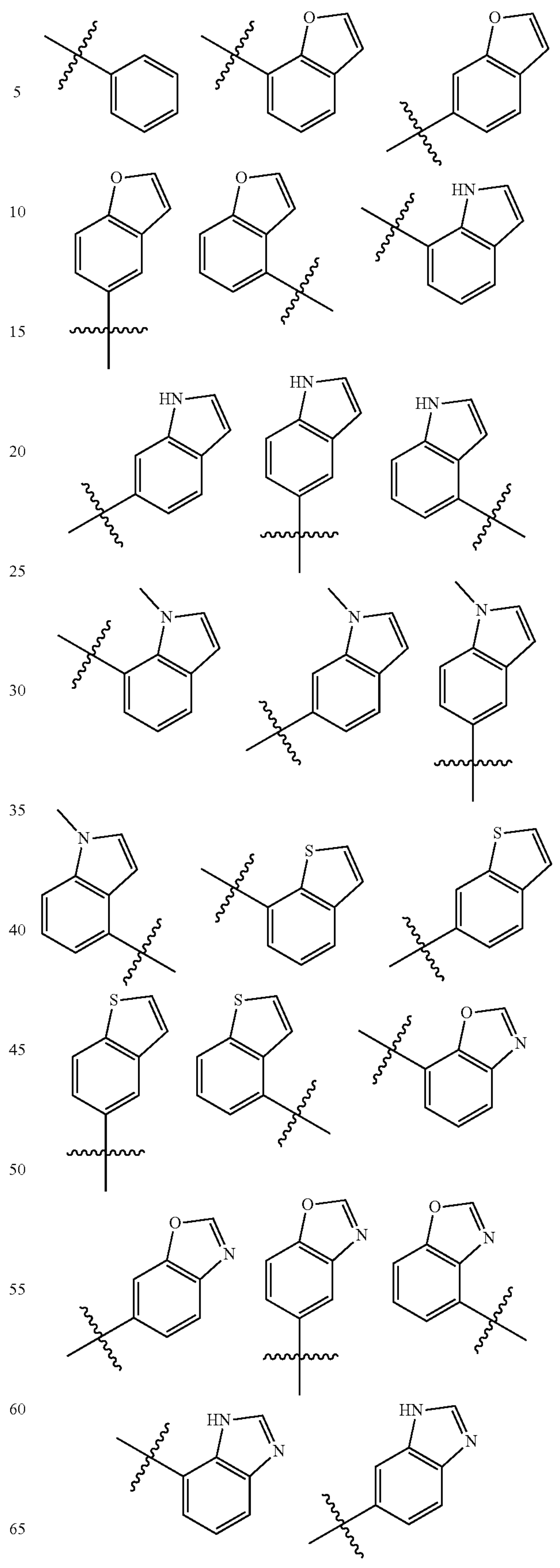

-continued
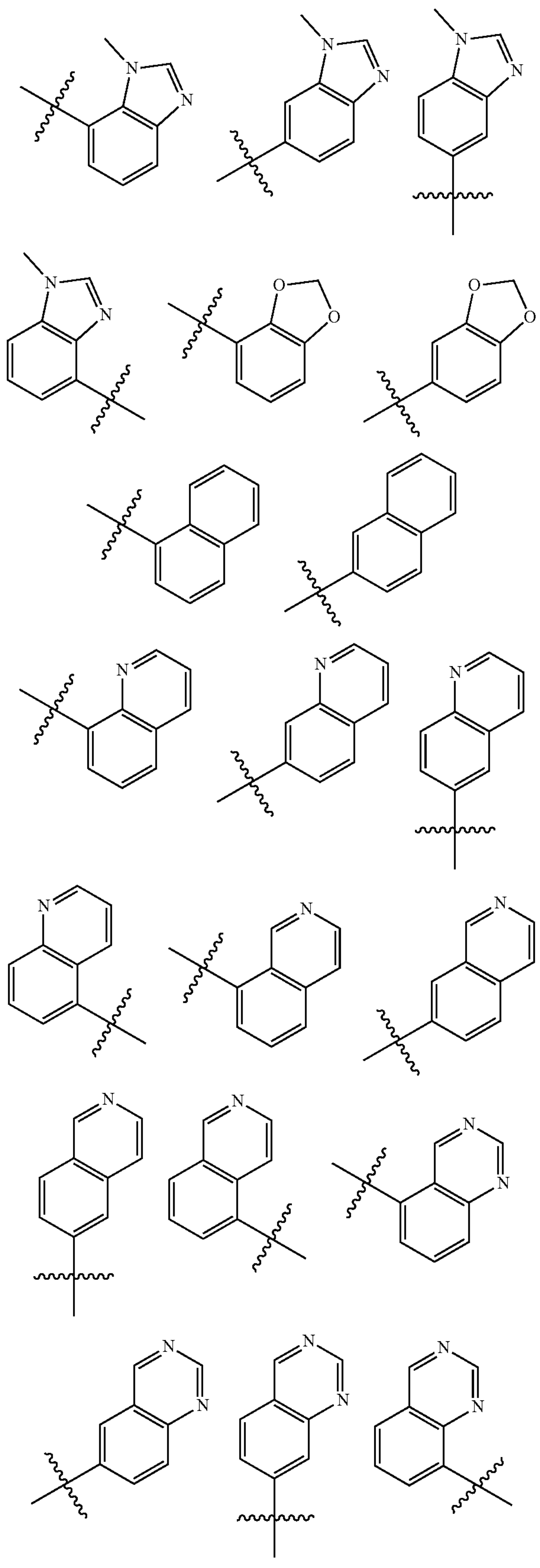
-continued
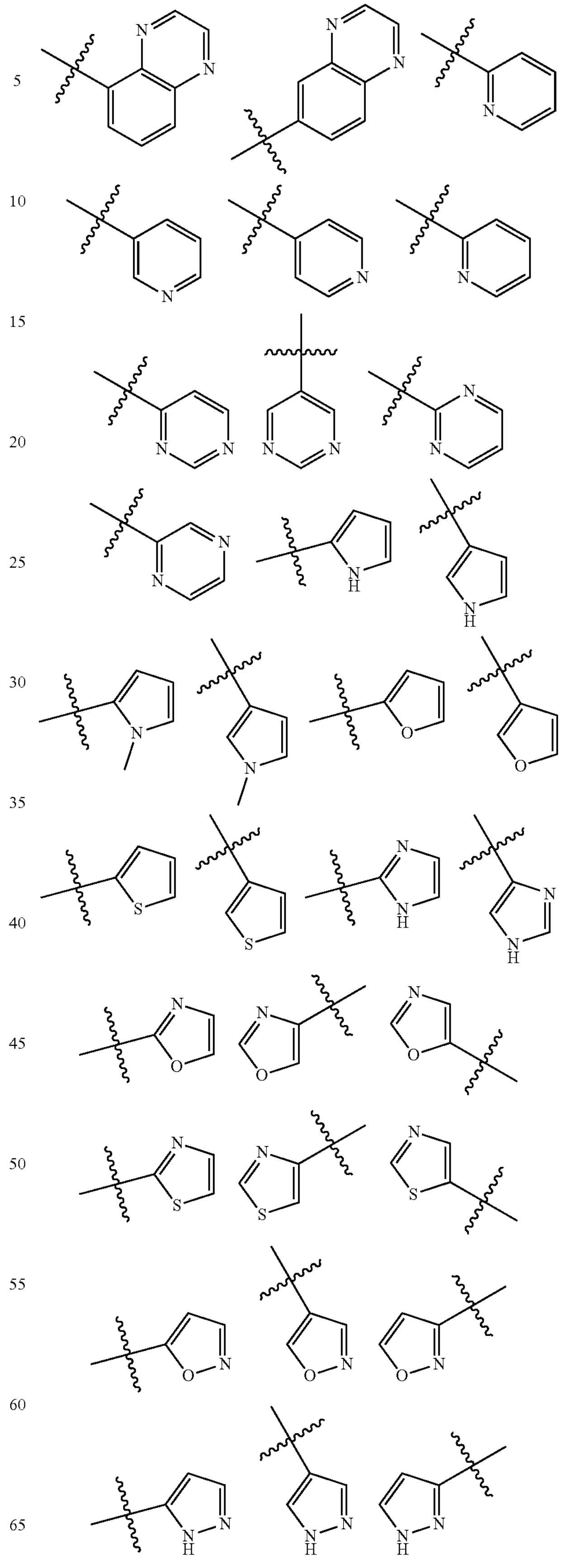

-continued

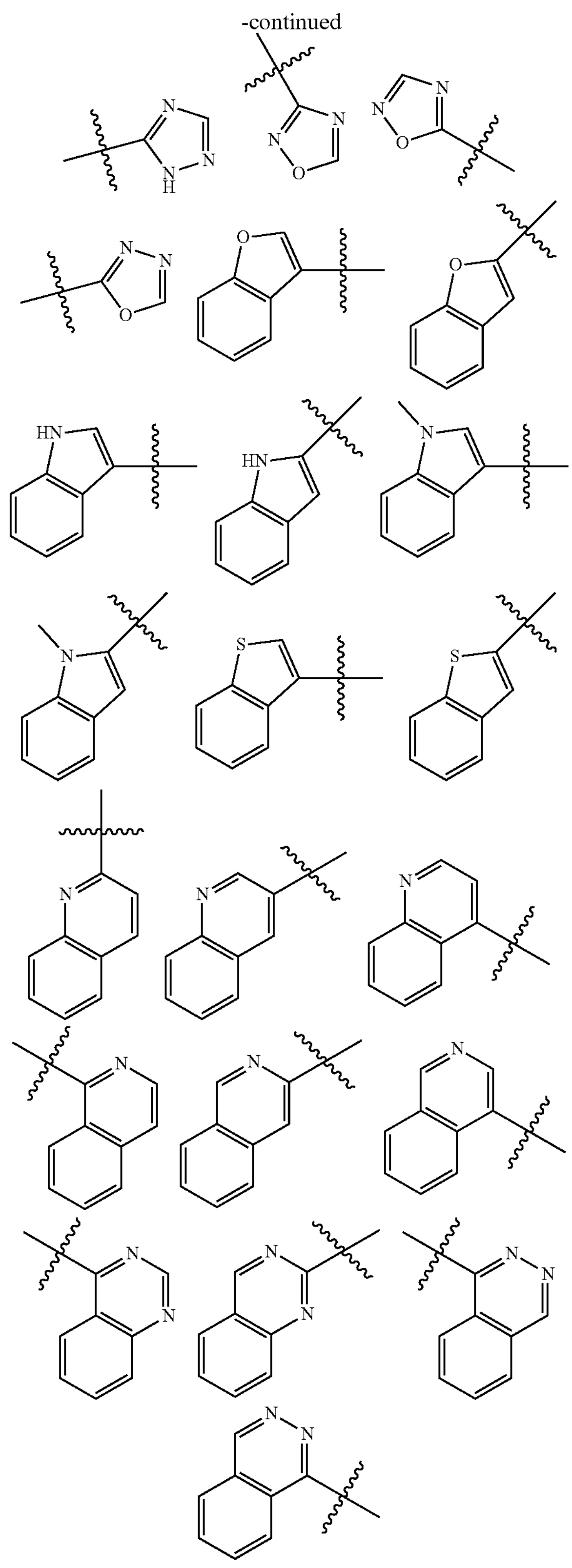

As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

The term "carbamate" is art-recognized and refers to a group

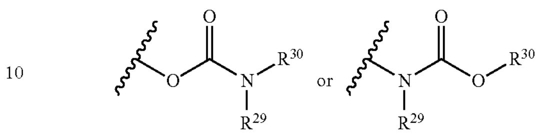

wherein $R^{29}$ and $R^{30}$ independently represent hydrogen or a hydrocarbyl group, such as an alkyl group, or $R^{29}$ and $R^{30}$ taken together with the intervening atom(s) complete a heterocycle having from 4 to 8 atoms in the ring structure.

As used herein, the term "carbamoyl" means —C(=O)—$NH_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

The term "carbocyclylalkyl", as used herein, refers to an alkyl group substituted with a carbocycle group.

The term "carbonate" is art-recognized and refers to a group —$OCO_2$—$R^{30}$, wherein $R^{30}$ represents a hydrocarbyl group.

The term "carboxy", as used herein, refers to a group represented by the formula —$CO_2H$.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a GlyT1 transporter inhibitor with a GlyT1 transporter with an individual or patient or cell includes the administration of the compound to an individual or patient, such as a human, as well as, for example, introducing a compound into a sample containing a cellular or purified preparation containing the GlyT1 transporter.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means $—N(NH_2)_2$.

The term "ester", as used herein, refers to a group $—C(O)OR^{30}$ wherein $R^{30}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the term "glycine transporter" or "GlyT" refers to membrane protein that facilitates the transport of glycine across the plasma membrane of a cell. Non-limiting examples of glycine transports include glycine transporter 1 (GlyT1) and glycine transporter 2 (GlyT2).

As used herein, the term "GlyT1" or "GlyT1 transporter" means sodium- and chloride-dependent glycine transporter 1, also known as glycine transporter 1, is a protein that in humans is encoded by the SLC6A9 gene (Kim K M, Kingsmore S F, Han H, Yang-Feng T L, Godinot N, Seldin M F, Caron M G, Giros B (June 1994). "Cloning of the human glycine transporter type 1: molecular and pharmacological characterization of novel isoform variants and chromosomal localization of the gene in the human and mouse genomes". Mol Pharmacol. 45 (4): 608-17; Jones E M, Fernald A, Bell G I, Le Beau M M (November 1995). "Assignment of SLC6A9 to human chromosome band 1p33 by in situ hybridization". Cytogenet Cell Genet. 71 (3): 211), which is hereby incorporated by reference in its entirety.

As used herein, the term "GlyT2" or "GlyT2 transporter" means sodium- and chloride-dependent glycine transporter 2, also known as glycine transporter 2, is a protein that in humans is encoded by the SLC6A5 gene (Morrow J A, Collie I T, Dunbar D R, Walker G B, Shahid M, Hill D R (November 1998). "Molecular cloning and functional expression of the human glycine transporter GlyT2 and chromosomal localisation of the gene in the human genome". FEBS Lett. 439 (3): 334-40), which is hereby incorporated by reference in its entirety.

As used herein, the term "GlyT1 inhibitor" means a compound that inhibits or blocks the activity of GlyT1 transporter including compounds inhibiting the activity of any isoform of GlyT1. Non-limiting examples of GlyT1 inhibitors are provided herein. In some embodiments, the GlyT1 inhibitor is a specific GlyT1 inhibitor, which means that the inhibitor has an inhibitor activity that is greater for GlyT1 as compared to GlyT2. In some embodiments, the inhibitor inhibits GlyT1 as compared to GlyT2 with at least, or about, 10%, 20%, 30%, 40%, 50%, 60%, 70%, 80%, 90%, 95%, 96%, 97%, 98%, 99% selectivity. In some embodiments, the GlyT1 inhibitor inhibits GlyT1 but does not inhibit or significantly inhibit the activity of GlyT2. A GlyT1 inhibitor that does not significantly inhibit the activity of GlyT2 if it inhibits the activity of GlyT2 less than 5%, 4%, 3%, 2%, or 1%. The selectivity of GlyT1 inhibitor is determined based on the known assays in the art such as the assays described in the published journal article (B. N. Atkinson, S. C. Bell, M. De Vivo, L. R. Kowalski, S. M. Lechner, V. I. Ognyanov, C.-S. Tham, C. Tsai, J. Jia, D. Ashton and M. A. Klitenick, ALX 5407: A Potent, Selective Inhibitor of the hGlyT1 Glycine Transporter, Molecular Pharmacology December 2001, 60 (6) 1414-1420), which is incorporated by its entirety.

As used herein, the term "GlyT2 inhibitor" means a compound that inhibits or blocks the activity of GlyT2 transporter including compounds inhibiting the activity of any isoform of GlyT2. In some embodiments, the GlyT2 inhibitor is a non-specific inhibitor, which means that it can also inhibit or block the activity of GlyT1. In some embodiments, the GlyT2 inhibitor is a specific GlyT2 inhibitor, which means that the inhibitor has an inhibitor activity that is greater for GlyT2 as compared to GlyT1. In some embodiments, the inhibitor inhibits GlyT2 as compared to GlyT1 with at least, or about, 10%, 20%, 30%, 40%, 50%, 60%, 70%, 80%, 90%, 95%, 96%, 97%, 98%, 99% selectivity. In some embodiments, the GlyT2 inhibitor inhibits GlyT2 activity but does not inhibit or significantly inhibit the activity of GlyT1. A GlyT2 inhibitor that does not significantly inhibit the activity of GlyT1 if it inhibits the activity of GlyT1 less than 5%, 4%, 3%, 2%, or 1%. The selectivity of GlyT2 inhibitor is determined based on the known assays in the art such as the assays based described in the published journal article (B. N. Atkinson, S. C. Bell, M. De Vivo, L. R. Kowalski, S. M. Lechner, V. I. Ognyanov, C.-S. Tham, C. Tsai, J. Jia, D. Ashton and M. A. Klitenick, ALX 5407: A Potent, Selective Inhibitor of the hGlyT1 Glycine Transporter, Molecular Pharmacology December 2001, 60 (6) 1414-1420), which is incorporated by its entirety.

As used herein, the term "guanidino" means $—NH(=NH)NH_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is $OCF_3$.

As used herein, the term "haloalkyl" means a $C_{1-6}$alkyl group having one or more halogen substituents. Examples of haloalkyl groups include, but are not limited to, $CF_3$, $C_2F_5$, $CH_2F$, $CHF_2$, $CCl_3$, $CHCl_2$, $CH_2CF_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which is, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

The term "heteroatom" as used herein means an atom of any element other than carbon or hydrogen. Exemplary heteroatoms are nitrogen, oxygen, and sulfur.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or $S(O)_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$alkyl substituted by heterocycloalkyl.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, $—CH_2OH$ and $—CH_2CH_2OH$.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting activity," such as enzymatic or transporter activity means reducing by any measurable amount the activity of an enzyme or transporter, such as the GlyT1 transporter.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "in situ gellable" means embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

As used herein, the phrase "integer from X to Y" means any integer that includes the endpoints. For example, the phrase "integer from X to Y" means 1, 2, 3, 4, or 5.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "N-alkyl" refers to a alkyl chain that is substituted with an amine group. Non-limiting examples, include, but are not limited to

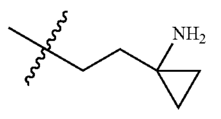 [SMILES: *CCC1(N)CC1]

and the like. The alkyl chain can be linear, branched, cyclic, or any combination thereof. In some embodiments, the alkyl comprises 1-10, 1-9, 1-8, 1-7, 1-6, 1-5, 1-4, 1-3, or 1-2 carbons.

As used herein, the term "nitro" means $-NO_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

For a compound described herein that contains a basic group, such as an amine, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

For a compound described herein that contains an acidic group, such as a carboxylic acid group, base addition salts can be prepared by any suitable method available in the art, for example, treatment of such compound with a sufficient amount of the desired the desired base, either neat or in a suitable inert solvent. Examples of pharmaceutically acceptable base addition salts include, but are not limited to, lithium, sodium, potassium, calcium, ammonium, zinc, or magnesium salt, or other metal salts; organic amino salts, such as, alkyl, dialkyl, trialkyl, or tetra-alkyl ammonium salts.

Other examples of pharmaceutically acceptable salts include, but are not limited to, camsylate, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, 7-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present application.

As used herein, the term "phenyl" means $—C_6H_5$. A phenyl group can be unsubstituted or substituted with one, two, or three suitable substituents.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

As used herein, the term "prodrug" means a derivative of a known direct acting drug, which derivative has enhanced delivery characteristics and therapeutic value as compared to the drug, and is transformed into the active drug by an enzymatic or chemical process. A common method for making a prodrug is to include one or more selected moieties which are hydrolyzed under physiologic conditions to yield the desired molecule. In certain embodiments, the prodrug is converted by an enzymatic activity of the host animal. For example, a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds of described herein in a formulation represented above can be replaced with the corresponding suitable prodrug.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the term "semicarbazone" means $=NNHC(=O)NH_2$.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $—OSO_3H$, or a pharmaceutically acceptable salt thereof.

The term "sulfonamide" is art-recognized and refers to the group represented by the general formulae

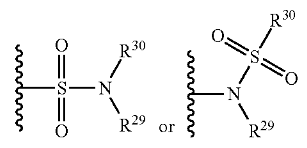

wherein $R^{29}$ and $R^{30}$ independently represents hydrogen or hydrocarbyl, such as alkyl, or $R^{29}$ and $R^{30}$ taken together with the intervening atom(s) complete a heterocycle having from 4 to 8 atoms in the ring structure.

The term "sulfoxide" is art-recognized and refers to the group —S(O)—$R^{30}$, wherein $R^{30}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{30}$, wherein $R^{30}$ represents a hydrocarbyl.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

The term "thioalkyl", as used herein, refers to an alkyl group substituted with a thiol group.

The term "thioester", as used herein, refers to a group —C(O)$SR^{30}$ or —SC(O)$R^{30}$ wherein $R^{30}$ represents a hydrocarbyl.

The term "thioether", as used herein, is equivalent to an ether, wherein the oxygen is replaced with a sulfur.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of erythropoietic protoporphyria" or "treating erythropoietic protoporphyria" means an activity that alleviates or ameliorates any of the primary phenomena or secondary symptoms associated with the erythropoietic protoporphyria or other condition described herein.

The term "urea" is art-recognized and may be represented by the general formula

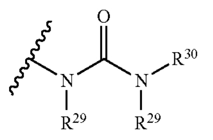

wherein $R^{29}$ and $R^{30}$ independently represent hydrogen or a hydrocarbyl, such as alkyl, or either occurrence of $R^{29}$ taken together with $R^{30}$ and the intervening atom(s) complete a heterocycle having from 4 to 8 atoms in the ring structure.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

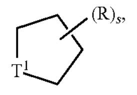

then it is understood that substituent R can occur s number of times on the ring, and R can be a different moiety at each occurrence. In the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present embodiments encompasses the use, where applicable, of stereoisomers, diastereomers and optical stereoisomers of the compounds, as well as mixtures thereof. Additionally, it is understood that stereoisomers, diastereomers, and optical stereoisomers of the compounds, and mixtures thereof, are within the scope of the embodiments. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the embodiments unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are provided herein. Cis and trans geometric isomers of the compounds are also included within the present embodiments and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

In some embodiments, the composition comprises a compound, or a pharmaceutically acceptable salt, solvate or prodrug thereof, that is at least 90%, at least 95%, at least 98%, or at least 99%, or 100% enantiomeric pure, which means that the ratio of one enantiomer to the other in the composition is at least 90:1 at least 95:1, at least 98:1, or at least 99:1, or is completely in the form of one enantiomer over the other. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

Resolution of racemic mixtures of compounds can be carried out by any of numerous methods known in the art, including, for example, chiral HPLC, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Glycine transporter inhibitors, such as GlyT1 inhibitors, including their pharmaceutically acceptable salts (e.g., the GlyT1 inhibitors as disclosed herein) can also exist as hydrates and solvates, as well as anhydrous and non-solvated forms. A "hydrate" is a compound that exists in a composition with water molecules. The composition can include water in stoichiometric quantities, such as a monohydrate or a dihydrate, or can include water in random amounts. A "solvate" is a similar composition except that a solvent other that water, such as with methanol, ethanol, dimethylformamide, diethyl ether and the like replaces the water. For example, methanol or ethanol can form an "alcoholate,"" which can again be stoichiometic or non-stoichiometric. Mixtures of such solvates or hydrates can also be prepared. The source of such solvate or hydrate can be from the solvent of crystallization, inherent in the solvent of preparation or crystallization, or adventitious to such solvent.

The compounds of the application, including their pharmaceutically acceptable salts and prodrugs, can exist as various polymorphs, pseudo-polymorphs, or in amorphous state. The term "polymorph", as used herein, refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Embodiments of various compounds and salts thereof are provided. Where a variable is not specifically recited, the variable can be any option described herein, except as otherwise noted or dictated by context.

In some embodiments, the compound is as described in the appended exemplary, non-limiting claims, or a pharmaceutically acceptable salt, solvate or prodrug thereof.

In some embodiments of the methods and uses disclosed herein, the GlyT1 inhibitor is a compound having a formula of Formula I

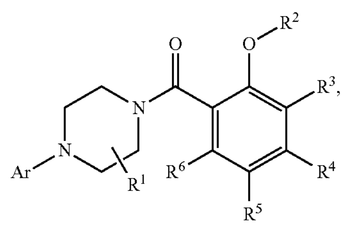

wherein:

Ar is unsubstituted or substituted aryl or 6-membered heteroaryl containing one, two or three nitrogen atoms, wherein the substituted aryl and the substituted heteroaryl groups are substituted by one or more substituents selected from the group consisting of hydroxy, halogen, $NO_2$, CN, $(C_1\text{-}C_6)$-alkyl, $(C_1\text{-}C_6)$-alkyl substituted by halogen, $(C_1\text{-}C_6)$-alkyl substituted by hydroxy, $(CH_2)n\text{-}(C_1\text{-}C_6)$-alkoxy, $(C_1\text{-}C_6)$-alkoxy substituted by halogen, $NR^7R^8$, $C(O)R^9$, $SO2R^{10}$, and $—C(CH_3)═NOR^7$, or are substituted by a 5-membered aromatic heterocycle containing 1-4 heteroatoms selected from N and O, which is optionally substituted by $(C_1\text{-}C_6)$-alkyl;

$R^1$ is hydrogen or $(C_1\text{-}C_6)$-alkyl;

$R^2$ is hydrogen, $(C_1\text{-}C_6)$-alkyl, $(C_2\text{-}C_6)$-alkenyl, $(C_1\text{-}C_6)$-alkyl substituted by halogen, $(C_1\text{-}C_6)$-alkyl substituted by hydroxy, $(CH2)n\text{-}(C_3\text{-}C_7)$-cycloalkyl optionally substituted by $(C_1\text{-}C_6)$-alkoxy or by halogen, $CH(CH_3)—(C_3\text{-}C_7)$-cycloalkyl, $(CH_2)_{n+1}—C(O)—R^9$, $(CH_2)_{n+1}—CN$, bicyclo[2.2.1]heptyl, $(CH_2)_{n+1}—O—(C_1\text{-}C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1\text{-}C_6)$-alkyl and $(C_1\text{-}C_6)$-alkoxy;

$R^3$, $R^4$ and $R^6$ are each independently hydrogen, hydroxy, halogen, $(C_1\text{-}C_6)$-alkyl, $(C_1\text{-}C_6)$-alkoxy or $O—(C_3\text{-}C_6)$-cycloalkyl;

$R^5$ is $NO_2$, CN, $C(O)R^9$ or $SO_2R^{10}$;

$R^7$ and $R^8$ are each independently hydrogen or $(C_1\text{-}C_6)$-alkyl;

$R^9$ is hydrogen, $(C_1\text{-}C_6)$-alkyl, $(C_1\text{-}C_6)$-alkoxy or $NR^7R^8$;

$R^{10}$ is $(C_1\text{-}C_6)$-alkyl optionally substituted by halogen, $(CH_2)_n—(C_3\text{-}C_6)$-cycloalkyl, $(CH_2)_n—(C_3\text{-}C_6)$-alkoxy, $(CH_2)_n$-heterocycloalkyl or $NR^7R^8$;

n is 0, 1, or 2;

or a pharmaceutically acceptable salt thereof, or a prodrug of the compound or its pharmaceutically acceptable salt.

In some embodiments of the methods and uses disclosed herein, the GlyT1 inhibitor is a compound having a formula of

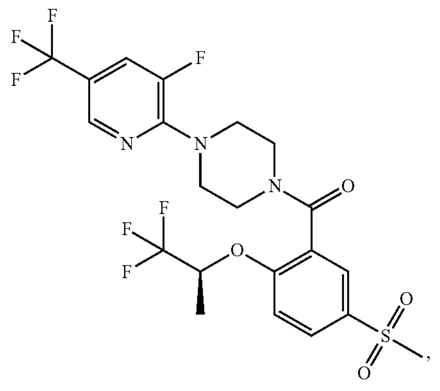 [SMILES: C[C@H](Oc1ccc(S(C)(=O)=O)cc1C(=O)N1CCN(c2ncc(C(F)(F)F)cc2F)CC1)C(F)(F)F]

bitopertin, or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula II

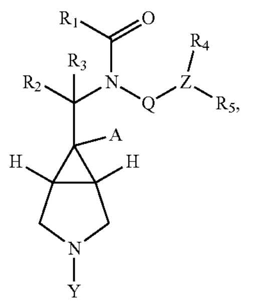

wherein:

$R^1$ represents a heteroaryl selected from the group consisting of: imidazolyl, thiazolyl, pyridyl, oxazolyl, pyrazolyl, triazolyl, oxadiazolyl, quinolinyl, isoxazolyl, pyrroloimidazoyl, and thiadiazole, wherein said heteroaryl is optionally substituted by one or more substituents selected from —OH, —$NR_7R_8$, halogen, $(C_1-C_8)$alkyl, $(C_3-C_{10})$cycloalkyl, $(C_1-C_8)$alkoxy, $(C_1-C_{12})$alkoxyalkyl, $(C_1-C_8)$hydroxyalkyl, $(C_6-C_{14})$aryl and benzyl;

$R_2$, $R_3$ and A independently represent H or $(C_1-C_8)$alkoxy, wherein said alkyl is optionally substituted by one or more —OH, $(C_1-C_8)$alkoxy, —$NR_7R_8$ or halogen;

Q represents —$(CH_2)_n$—, where n=1, 2, 3 or 4 or —$(CH_2)_m$ —O—, where m=2, 3 or 4;

Z represents $(C_6-C_{14})$aryl, $(C_1-C_8)$alkyl or $(C_3-C_8)$cycloalkyl;

$R_4$ and $R_5$ each independently represent H, halogen, $(C_1-C_8)$alkyl, $(C_6-C_{14})$aryl, $(C_6-C_{14})$aryloxy, $(C_1-C_8)$alkoxy, (3-10 membered)heterocycloalkyl or $(C_3-C_8)$cycloalkoxy; wherein $R_4$ and $R_5$ are optionally substituted by one or more —OH, $(C_1-C_8)$alkoxy, —$NR_7R_8$ or halogen;

Y represents —$R_6$, —$(CH_2)$o-$R_6$, —$C(R_6)_3$ or —$CH(R_6)_2$, wherein 0=1, 2 or 3;

$R_6$ represents H, $(C_6-C_{14})$aryl, $(C_{1-10})$alkyl, $(C_3-C_{10})$cycloalkyl, $(C_5-C_{18})$bicycloalkyl, $(C_5-C_{18})$tricycloalkyl, (3-10 membered)heterocycloalkyl, (5-10 membered) heteroaryl, —C(═O)$NR_7R_8$, or —C(═O)$OR_7$, wherein said $R_6$ groups can optionally be substituted with one or more X groups;

wherein X═—OH, $(C_1-C_8)$alkoxy, —$NR_{11}R_{12}$, —$SO_2R_{10}$, —C(═O)$R_{10}$, halogen, cyano, $(C_1-C_8)$alkyl, $(C_1-C_{10})$alkoxyalkyl, (5-10 membered)heteroaryl, $(C_6-C_{14})$aryl, $(C_6-C_{14})$aryloxy, benzyl, or $(C_1-C_8)$hydroxyalkyl;

wherein $R_7$ and $R_8$ independently represent H, $(C_1-C_8)$ alkyl, $(C_3$-C8)cycloalkyl, (5-10 membered)heterocycloalkyl, $(C_1-C_8)$hydroxyalky, (5-10 membered)heteroaryl or $(C_1-C_{10})$alkoxyalkyl; wherein $R_7$ and $R_8$ may optionally be substituted by one or more X groups;

or $R_7$ and $R_8$ together with the nitrogen in which they may be attached may form a (3-10 membered)heterocycloalkyl group optionally substituted by one or more X groups;

wherein $R_{10}$ represents $(C_1-C_8)$alkyl, $(C_3-C_8)$cycloalkyl, (3-10 membered)heterocycloalkyl, $(C_1-C_8)$hydroxyalky, (5-10 membered)heteroaryl or $(C_1-C_{10})$alkoxyalkyl;

wherein $R^{11}$ and $R^{12}$ independently represent H, $(C_1-C_8)$ alkyl, $(C_3-C_8)$cycloalkyl, (5-10 membered)heterocycloalkyl, $(C_1-C_8)$hydroxyalky, (5-10 membered)heteroaryl or $(C_1-C_{10})$alkoxyalkyl; or a pharmaceutically acceptable salt thereof, or a prodrug of the compound or its pharmaceutically acceptable salt.

In some embodiments of the methods and uses disclosed herein, the GlyT1 inhibitor is a compound having a formula of

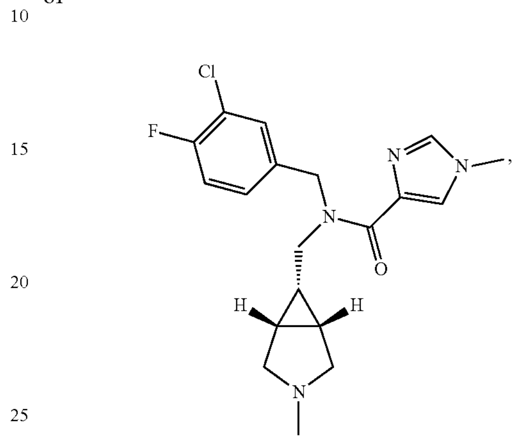

or a pharmaceutically acceptable salt thereof, or a prodrug of the compound or its pharmaceutically acceptable salt.

In some embodiments of the methods and uses disclosed herein, the GlyT1 inhibitor is a compound having a formula of

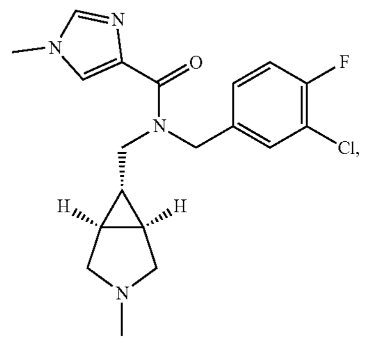 [SMILES: CN1C[C@@H]2[C@H](C1)[C@H]2CN(Cc1ccc(F)c(Cl)c1)C(=O)c1cn(C)cn1]

PF-3463275, or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula III

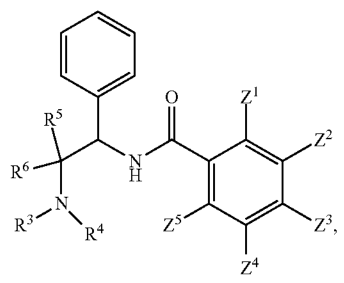

wherein:

$Z^1$ is selected from the group consisting of $C_{1-4}$alkyl, $C_{3-6}$CycloalkVI, $C_{1-4}$alkoxy, $C_{1-4}$alkylthio, halo$C_{1-4}$alkyl, phenyl, halo$C_{1-4}$alkoxy, halophenyl, $C_{1-4}$alkylsulfoxy, $C_{1-4}$alkylsulfonyl, bromo and chloro;

$Z^2$ is selected from the group consisting of hydrogen, halogen, cyano, $C_{1-4}$alkyl, phenyl, halo$C_{1-4}$alkyl, halo$C_{1-4}$alkoxy, halophenyl, $C_{1-4}$alkoxy$C_{1-4}$alkyl and $C_{3-6}$cycloalkyl;

$Z^3$ is selected from the group consisting of hydrogen, halogen, $C_{1-4}$alkyl, $C_{1-4}$alkoxy, $C_{1-4}$alkylthio, halo$C_{1-4}$alkyl, halo$C_{1-4}$alkoxy, and $C_{3-6}$cycloalkyl;

$Z^4$ is selected from the group consisting of hydrogen, halogen, C1-3alkyl, halo$C_{1-4}$alkyl, $C_{1-4}$alkoxy, $C_{1-4}$alkylthio, phenyl, halo$C_{1-4}$alkoxy, halophenyl, $C_{1-4}$alkoxy$C_{1-4}$alkyl and $C_{3-6}$cycloalkyl;

$Z^5$ is selected from the group consisting of hydrogen, fluoro, chloro, bromo, iodo, hydroxy, $C_{1-4}$alkyl, $C_{1-4}$alkoxy, $C_{1-4}$alkylthio, phenyl, halo$C_{1-4}$alkyl, halo$C_{1-4}$alkoxy, halophenyl, $C_{1-4}$alkoxy$C_{1-4}$alkyl and $C_{3-6}$cycloalkyl;

whereby if more than one of $Z^1$ to $Z^5$ is methoxy, then only $Z^1$ and $Z^5$ are methoxy $R^3$ and $R^4$ are independently selected from hydrogen and $C_{1-4}$alkyl, optionally substituted with one or more groups Y; or $R^3$ and $R^4$ together with the nitrogen atom to which they are attached form a saturated or partially unsaturated A-, 5-6- or 7-membered carbocyclic ring optionally substituted with a group Y';

Y is selected from the group consisting of $C_{1-4}$alkoxy, hydroxy, halo$C_{1-4}$alkoxy and $C_{3-5}$cycloalkyl;

Y' is selected from the group consisting of $C_{1-4}$alkyl, $C_{1-4}$alkoxy, halogen, hydroxy, halo$C_{1-4}$alkoxy, $C_{3-5}$cycloalkyl and $C_{5-10}$aryl or Y' forms a —CH2- or —CH2-CH2- bridge between two atoms on the A-, 5-, 6- or 7-membered carbocyclic ring;

$R^5$ and $R^6$ are independently $C_{1-4}$alkyl, optionally substituted with one or more groups X; or $R^5$ and $R^6$ together with the carbon atom to which they are attached form a saturated 5- or 6-membered ring carbocyclic optionally substituted with one or more groups X', in the case of $R^5$ and $R^6$ together with the carbon atom to which they are attached forming a 5-membered saturated carbocyclic ring, that ring may optionally further comprising an additional heteroatom group selected from O, N and S(O)m; where m=0, 1 or 2.

X is selected from the group consisting of halogen, hydroxy, $C_{1-4}$alkoxy, halo$C_{1-4}$alkyl, halo$C_{1-4}$alkoxy and $C_{5-10}$aryl; and X' is selected from the group consisting of halogen, hydroxy, $C_{1-4}$alkyl, $C_{1-4}$alkoxy, halo$C_{1-4}$alkyl, halo$C_{1-4}$alkoxy and $C_{5-10}$aryl;

whereby $R^3$, $R^4$, $R^5$ and $R^6$ are not all simultaneously unsubstituted methyl;

with the provisos that when simultaneously $Z^1$ is propyloxy, $Z^3$ is chloro, $Z^2$=$Z^4$=$Z^5$=H, and $R^5$ and $R^6$ are both methyl, then $R^3$ and $R^4$ together with the nitrogen atom to which they are attached do not form a 2-methylpyrrolidine group; when simultaneously $Z^1$ is methyl, $Z^3$ is methoxy, $Z^2$=Z4=Z5=H, and $R^5$ and $R^6$ are both methyl, then $R^3$ and $R^4$ together with the nitrogen atom to which they are attached do not form a pyrrolidine group, or a pharmaceutically acceptable salt thereof, or a prodrug of the compound or its pharmaceutically acceptable salt.

In some embodiments of the methods and uses disclosed herein, the GlyT1 inhibitor is a compound having a formula of

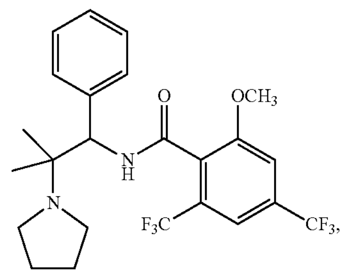 [SMILES: COc1cc(C(F)(F)F)cc(C(F)(F)F)c1C(=O)NC(c1ccccc1)C(C)(C)N1CCCC1]

or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula IV

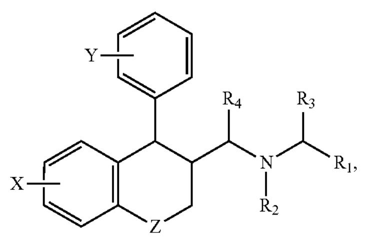

wherein:

Z is $(CH_2)_n$, O, S, SO, $SO_2$ or N—$R_5$;

n is 0, 1 or 2;

X represents 1-3 substituents independently selected from hydrogen, halogen, $(C_{1-6})$alkyioxy, $(C_{3-6})$cycloalkyloxy, $(C_{6-12})$aryloxy, $(C_{6-12})$aryl, thienyl, SR6, SOR6, $SO_2R_6$, $NR_6R_6$, $NHR_6$, $NH_2$, $NHCOR_6$, $NSO_2R_6$, CN, $COOR_6$ and $(C_{1-4})$alkyl, optionally substituted with halogen, $(C_{6-12})$aryl, $(C_{1-6})$alkyloxy or $(C_{6-12})$aryloxy; or 2 substituents at adjacent positions together represent a fused $(C_{5-6})$aryl group, a fused $(C_{5-6})$cycloalkyl ring or O—$(CH_2)_m$—O; m is 1 or 2;

Y represents 1-3 substituents independently selected from hydrogen, halogen, $(C_{1-4})$alkyloxy, $SR_6$, $NR_6R_6$ and $(C_{1-4})$alkyl, optionally substituted with halogen;

$R_1$ is $COOR_7$ or $CONR_8R^9$;

$R_2$ and R6 are $(C_{1-4})$alkyl;

$R_3$, $R_4$ are $R_5$ are independently hydrogen or $(C_{1-4})$alkyl;

$R_7$, $R_8$ and $R_9$ are independently hydrogen, $(C_{1-4})$alkyl, $(C_{6-12})$aryl or arylalkyl, or a pharmaceutically acceptable salt thereof, or a prodrug of the compound or its pharmaceutically acceptable salt.

In some embodiments of the methods and uses disclosed herein, the GlyT1 inhibitor is a compound having a formula of

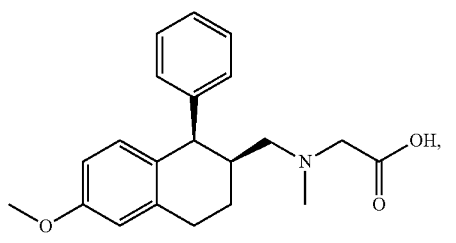 [SMILES: COc1ccc2c(c1)CC[C@H](CN(C)CC(=O)O)[C@@H]2c1ccccc1]

ORG-25935, or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula V

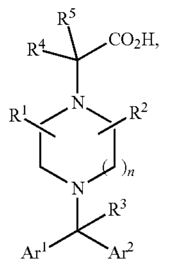

wherein:

n is an integer from 1 to 3;

$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^c$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$-alkylene chain wherein one of the carbon atoms in the alkylene chain is optionally replaced by a —NR—, —O—, —S(O)n- (where R is hydrogen or alkyl and n is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C≡C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring-in $R^g$, $R^h$ and $R^i$ is optionally substituted with $R^j$, $R^k$, or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula V is not 2-(4-benzhydrylpiperazin-1-yl)acetic acid, 2-(4-((4-chlorophenyl)(phenyl)methyl)piperazin-1-yl)acetic acid, 2-((2R,5S)-4-((R)-(4-(1H-tetrazol-5-yl)phenyl)(3-hydroxyphenyl)methyl)-2,5-dimethylpiperazin-1-yl)acetic acid, or 2-((2R,5S)-4-((R)-(4-cyanophenyl)(3-hydroxyphenyl)methyl)-2,5-dimethylpiperazin-1-yl)acetic acid, or a pharmaceutically acceptable salt thereof, or a prodrug of the compound or its pharmaceutically acceptable salt.

In some embodiments of the methods and uses disclosed herein, the GlyT1 inhibitor is a compound having a formula of

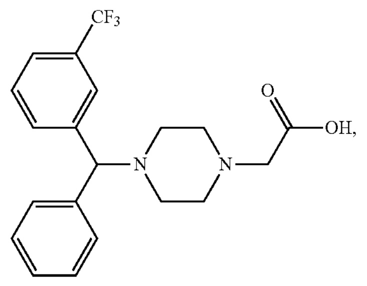 [SMILES: O=C(O)CN1CCN(C(c2ccccc2)c2cccc(C(F)(F)F)c2)CC1]

or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula VI

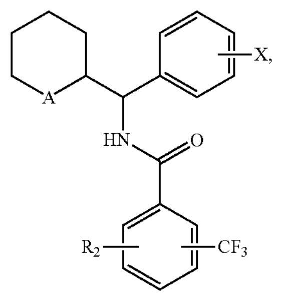

wherein:

A represents a group of general formula N—$R_1$, a group of general formula N+(O—)$R_1$ or a group of general formula N+(R')$R_1$, and in which $R_1$ represents either a hydrogen atom, or a linear or branched $(C_1-C_7)$alkyl group optionally substituted with one or more fluorine atoms, or a $(C_4-C_7)$cycloalkyl group, or a $(C_3-C_7)$cycloalkyl$(C_1-C_3)$alkyl group, or a phenyl$(C_1-C_3)$alkyl group optionally substituted with one or two hydroxyl or methoxy groups, or a $(C_2-C_4)$alkenyl group, or a $(C_2-C_4)$alkynyl group, R' represents a linear or branched $(C_1-C_7)$alkyl group, X represents a hydrogen atom or one or more substituents chosen from halogen atoms and trifluoromethyl, linear or branched (C1-C4)alkyl and $(C_1-C_4)$alkoxy groups, $R_2$ represents either a hydrogen atom, or one or more substituents chosen from halogen atoms and trifluoromethyl, (C1-C4)alkyl or $(C_1-C_4)$alkoxy groups, or amino groups of general formula $NR_3R_4$ in which $R_3$ and $R_4$ each represent, independently of each other, a hydrogen atom or a $(C_1-C_4)$alkyl group, or form with the nitrogen atom carrying them a pyrrolidine, piperidine or morpholine ring, or a phenyl group optionally substituted with an atom or a group as defined for the symbol X above, or a pharmaceutically acceptable salt thereof, or a prodrug of the compound or its pharmaceutically acceptable salt.

In some embodiments of the methods and uses disclosed herein, the GlyT1 inhibitor is a compound having a formula of

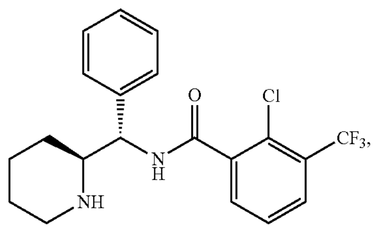 [SMILES: O=C(N[C@@H](c1ccccc1)[C@@H]1CCCCN1)c1cccc(C(F)(F)F)c1Cl]

SSR-504734, or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula VII

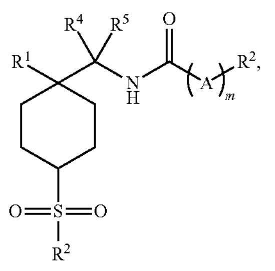

wherein:

$R^1$ is $-(CH_2)_n-R^{1a}$, wherein n is independently 0-6, and $R^{1a}$ is selected from the group consisting of:

(1) $C_{1-6}$alkyl, which is unsubstituted or substituted with 1-6 halogen, hydroxy, (2) phenyl substituted with $R^{2a}$, $R^{2b}$ and $R^{2c}$, (3) $C_{3-6}$cycloallyl, which is unsubstituted or substituted with $C_{1-6}$alkyl, 1-6 halogen, hydroxy or $-NR^{10}R^{11}$, (4) $-O-C_{1-6}$alkyl, which is unsubstituted or substituted with 1-6 halogen, hydroxy or $-NR^{10}R^{11}$, (5) $-CO2R^9$, wherein $R^9$ is independently selected from:

(a) hydrogen, (b) $-C_{1-6}$alkyl, which is unsubstituted or substituted with 1-6 fluoro, (c) benzyl, and (d) phenyl, (6) $-NR^{10}R^{11}$, wherein $R^{10}$ and $R^{11}$ are independently selected from:

(a) hydrogen, (b) $-C_{1-6}$alkyl, which is unsubstituted or substituted with hydroxy, 1-6 fluoro or $-NR^{12}R^{13}$, where $R^{12}$ and $R^{13}$ are independently selected from hydrogen and $-C_{1-6}$alkyl, (c) $-C_{3-6}$cycloalkyl, which is unsubstituted or substituted with hydroxy, 1-6 fluoro or $-NR^{12}R^{13}$, (d) benzyl, (e) phenyl, and (7) $-CONR^{10}R^{11}$;

$R^2$ is selected from the group consisting of:

(1) phenyl, which is substituted with $R^{2a}$, $R^{2b}$ and $R^{2c}$, (2) $C_{1-8}$alkyl, which is unsubstituted or substituted with 1-6 halogen, hydroxy, $-NR^{10}R^{11}$, phenyl or heterocycle, where the phenyl or heterocycle is substituted with $R^{2a}$, $R^{2b}$ and $R^{2c}$, (3) $C_{3-6}$cycloalkyl, which is unsubstituted or substituted with 1-6 halogen, hydroxy or $NR^{10}R^{11}$, and (4) $-C_{1-6}$alkyl-($C_{3-6}$cycloalkyl), which is unsubstituted or substituted with 1-6 halogen, hydroxy or $-NR^{10}R^{11}$;

$R^{2a}$, $R^{2b}$ and $R^{2c}$ are independently selected from the group consisting of:

(1) hydrogen, (2) halogen, (3) $-C_{1-6}$alkyl, which is unsubstituted or substituted with:

(a) 1-6 halogen, (b) phenyl, (c) $C_{3-6}$cycloalkyl, or (d) $-NR^{10}R^{11}$, (4) $-O-C_{1-6}$alkyl, which is unsubstituted or substituted with 1-6 halogen, (5) hydroxy, (6) $-SCF_3$, (7) $-SCHF_2$, (8) $-SCH_3$, (9) $-CO_2R^9$,

(10) CN,

(11) $-SO_2R^9$,

(12) $-SO_2-NR^{10}R^{11}$,

(13) $-NR^{10}R^{11}$,

(14) $-CONR^{10}R^{11}$, and

(15) $-NO_2$;

$R^3$ is selected from the group consisting of:

(1) $C_{1-6}$alkyl, which is unsubstituted or substituted with 1-6 halogen, hydroxyl, or $-NR^{10}R^{11}$, (2) $C_{3-6}$cycloalkyl, which is unsubstituted or substituted with 1-6 halogen, hydroxyl or $-NR^{10}R^{11}$, $R^4$ and $R^5$ are independently selected from the group consisting of:

(1) hydrogen, and (2) $C_{1-6}$alkyl, which is unsubstituted or substituted with halogen or hydroxyl, or $R^4$ and $R^5$ taken together form a $C_{3-6}$cycloalkyl ring; A is selected from the group consisting of:

(1) —O—, and (2) —$NR^{10}$—;

m is zero or one, whereby when m is zero $R^2$ is attached directly to the carbonyl;

and pharmaceutically acceptable salts thereof and individual enantiomers and diastereomers thereof, or a pharmaceutically acceptable salt thereof, or a prodrug of the compound or its pharmaceutically acceptable salt.

In some embodiments of the methods and uses disclosed herein, the GlyT1 inhibitor is a compound having a formula of

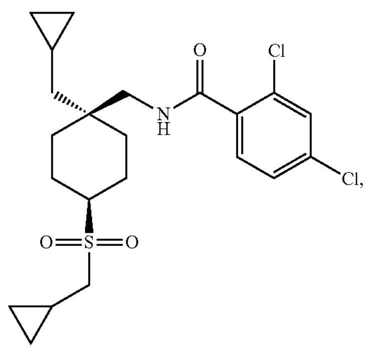 [SMILES: O=C(NC[C@]1(CC2CC2)CC[C@H](S(=O)(=O)CC2CC2)CC1)c1ccc(Cl)cc1Cl]

or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula VIII

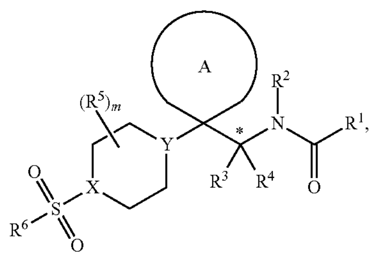

wherein:

$R^1$ is phenyl independently substituted from 1 to 5 times with halogen, $C_1$-$C_3$ alkyl, $C_3$-$C_6$ cycloalkyl, $OR^9$, or $SR^{10}$, wherein $C_1$-$C_3$ alkyl and $C_3$-$C_6$ cycloalkyl are optionally substituted with 1 to 10 times with $R^7$;

$R^2$ is H;

$R^3$ and R4 are each individually H or $CH_3$;

$R^5$ is selected from the group consisting of:

(1) hydrogen, (2) $C_1$-$C_6$ alkyl which is optionally substituted from 1 to 11 times with $R^7$, (3) gem-dialkyl, and (4) gem-dihalo; or two $R^5$ substituents on the same carbon, together with the carbon atom to which they are attached, may form a 3-, 4-, or 5-membered cycloalkyl optionally substituted from 1 to 10 times with $R^7$; or two $R^5$ substituents on adjacent carbons of the ring to which they are attached, together may form a 3-, 4-, 5- or 6-membered cycloalkyl optionally substituted from 1 to 10 times with $R^7$;

$R^6$ is

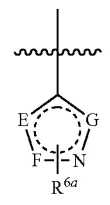

wherein E, F, and G are each independently nitrogen or carbon and $R^{6a}$ is $C_1$-$C_2$ alkyl, which is optionally substituted 1 to 5 times with halogen or deuterium;

$R^7$ is selected from the group consisting of:

(1) hydrogen, (2) halogen, (3) deuterium, (4) gem-dialkyl, (5) gem-dihalo, (6) —$OR^9$, —$NR^{11}R^{12}$, —$NR^{11}C(O)_pR^{10}$, —$S(O)_pR^{10}$, —CN, —NO2, —$C(O)_pR^{10}$, —$C(O)NR^{11}R^{12}$, or —$NR^{11}C(S)R^{10}$, and (7) oxo or thio;

$R^8$ is selected from the group consisting of:

(1) hydrogen, (2) halogen, (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$cycloalkylalkyl is independently and optionally substituted from 1 to 11 times with $R^7$, or (4) —$OR^9$, —$NR^{11}R^{12}$, —$NR^{11}C(O)_pR^{10}$, —$S(O)_pR^{10}$, —CN, —NO2, —$C(O)_pR^{10}$, —$C(O)NR^{11}R^{12}$, or —$NR^{11}C(S)R^{10}$;

$R^9$ is selected from the group consisting of hydrogen, $C_1$-$C_4$ alkyl, $C_3$-$C_7$ cycloalkyl, $C_4$-$C_7$ cycloalkylalkyl, —$C(O)NR^{11}R^{12}$, and —$C(O)_pR^{10}$, wherein each of $C_1$-$C_4$ alkyl, $C_3$-$C_7$ cycloalkyl, and $C_4$-$C_7$ cycloalkylalkyl is optionally substituted from 1 to 11 times with $R^7$;

$R^{10}$ is selected from the group consisting of hydrogen, $C_1$-$C_4$ alkyl, $C_3$-$C_7$ cycloalkyl $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$;

$R^{11}$ and $R^{12}$ are each independently selected from the group consisting hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$, or $R^{11}$ and $R^{12}$ are taken together with the nitrogen to which they are attached to form a saturated or partially saturated monocyclic or fused bicyclic heterocycle optionally substituted from 1 to 11 times with $R^7$;

A is

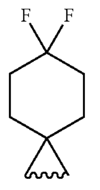

X is N;

Y is N;

p is 1, or 2; and m is 0;

with the following provisos that: $R^6$ cannot be (a) 1H-1,2,3-triazol-4-yl, or (b) 5-methylisoxazol-4-yl;

or an oxide thereof, a pharmaceutically acceptable salt of the compound or its oxide, or an individual enantiomer or diastereomer thereof.

In some embodiments of the methods and uses disclosed herein, the GlyT1 inhibitor is a compound having a formula of

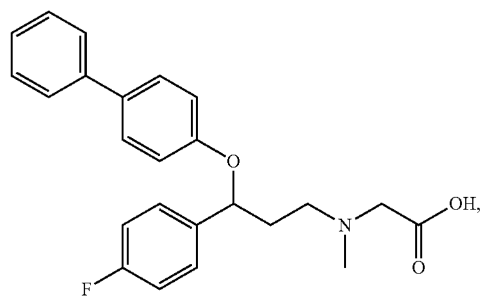

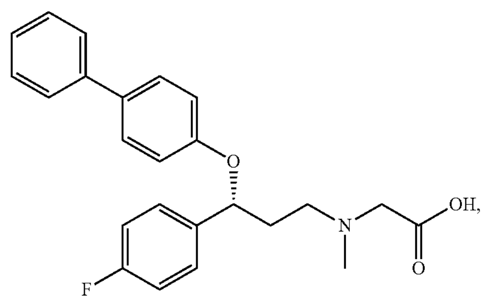

(ALX-5407)

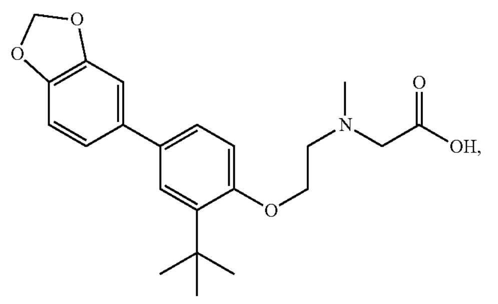

-continued

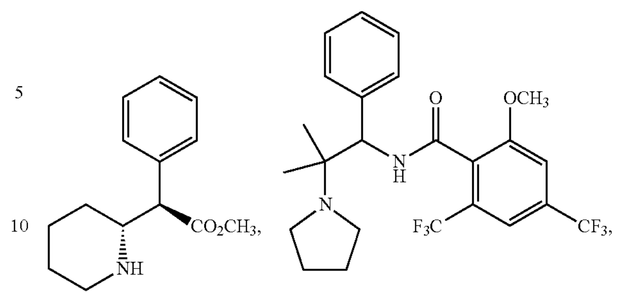

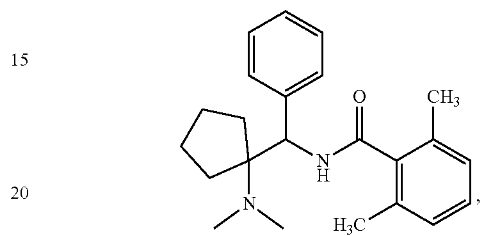

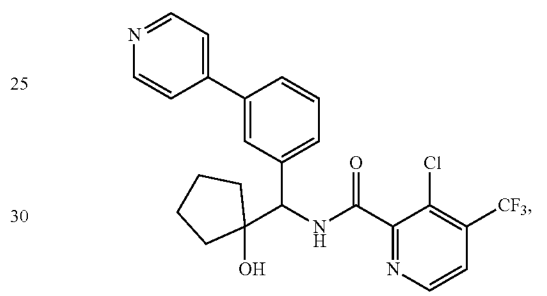

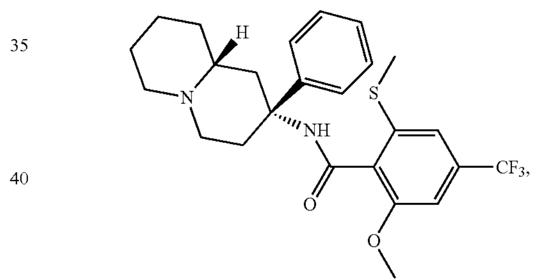

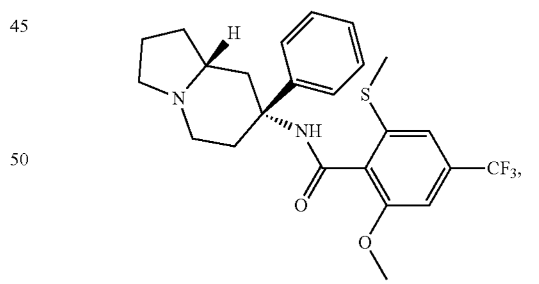

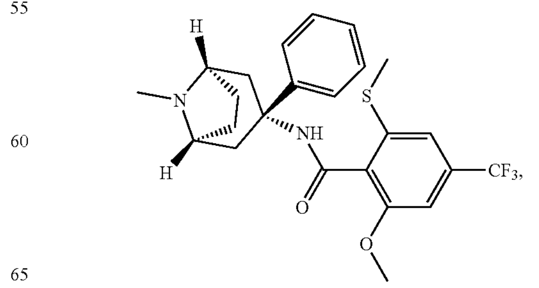

-continued
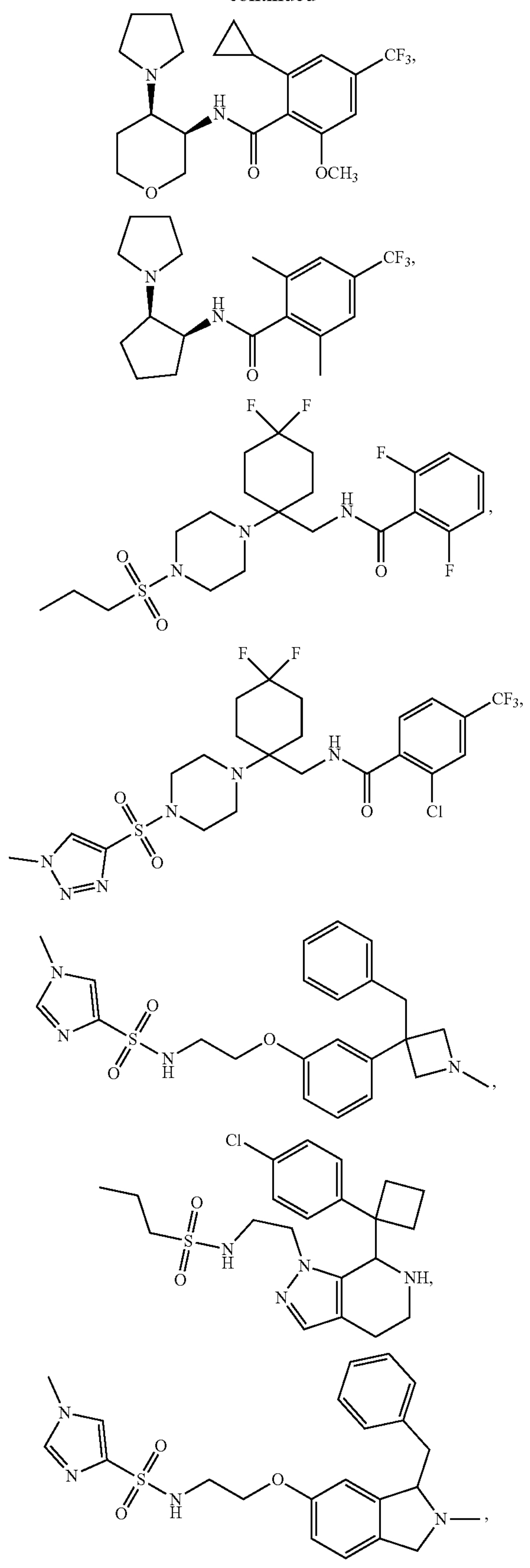
-continued
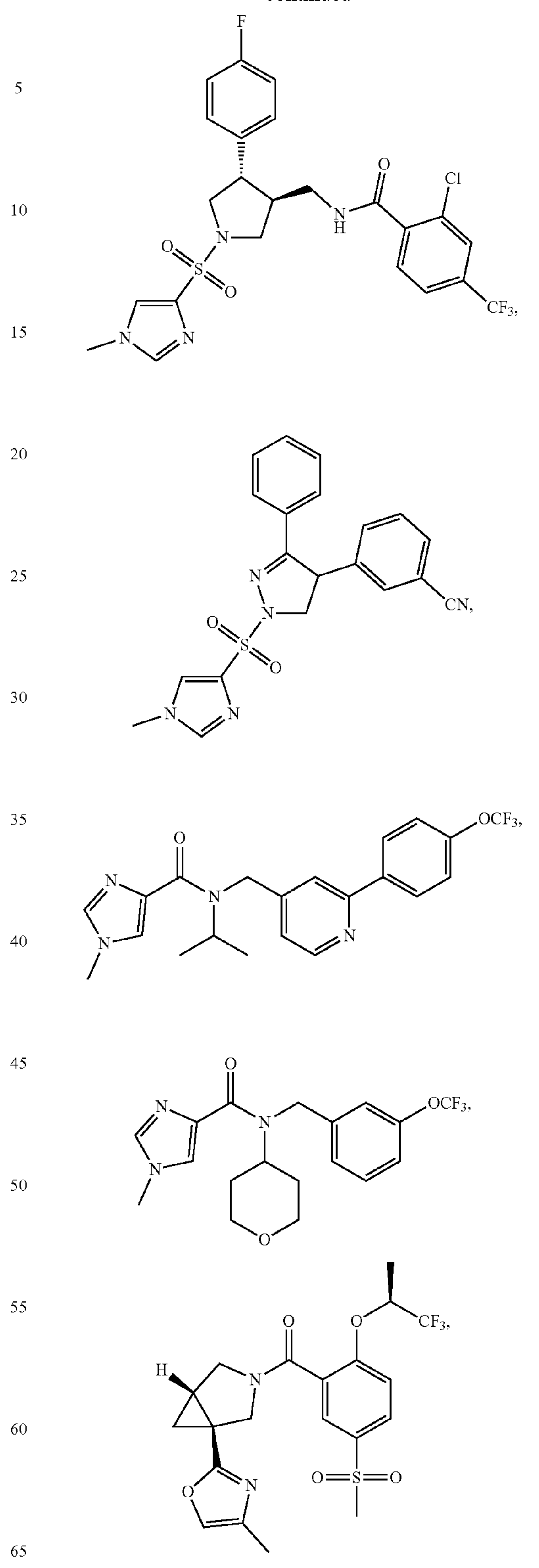

-continued
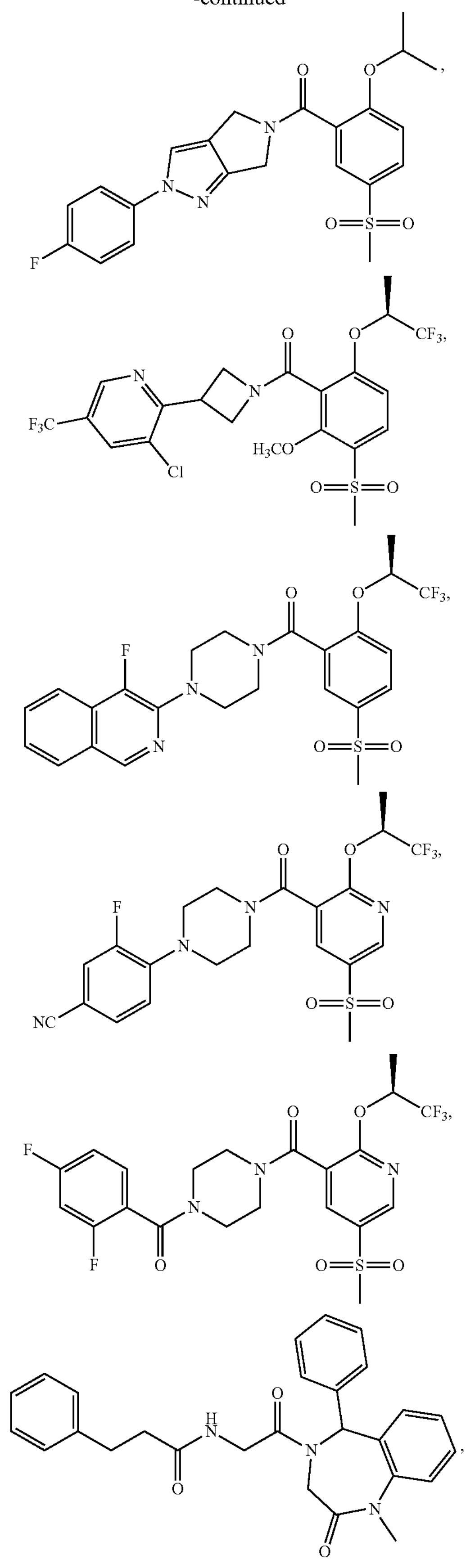
-continued
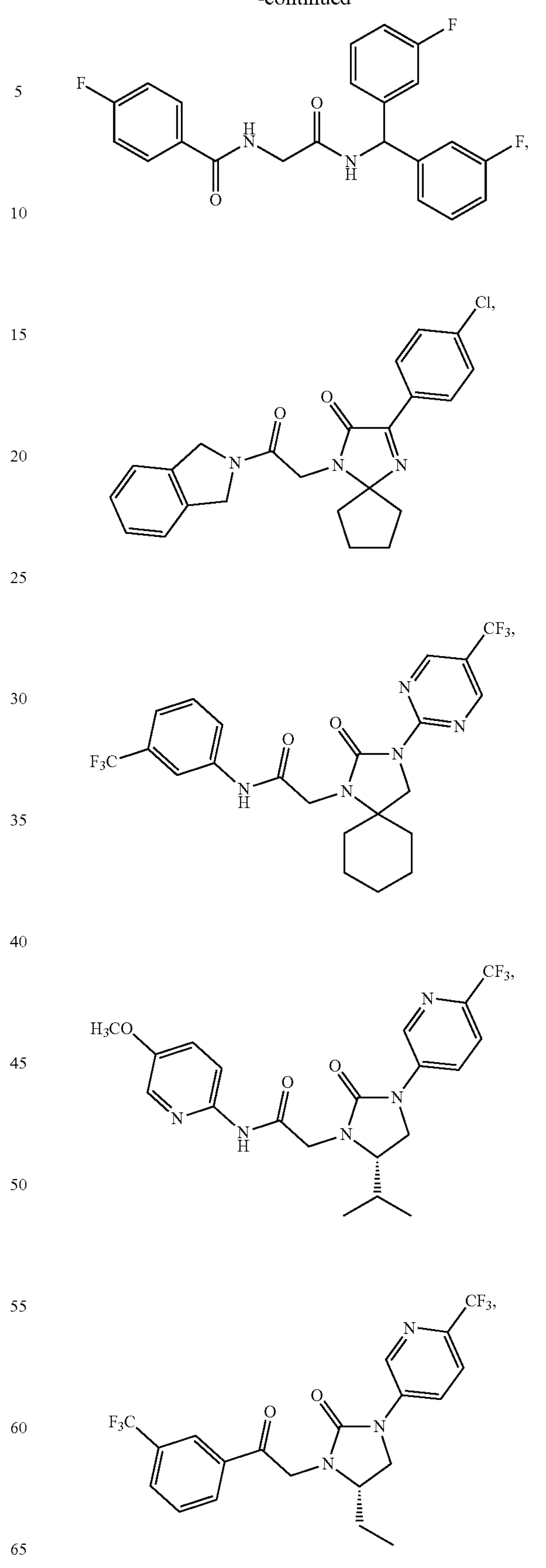

-continued

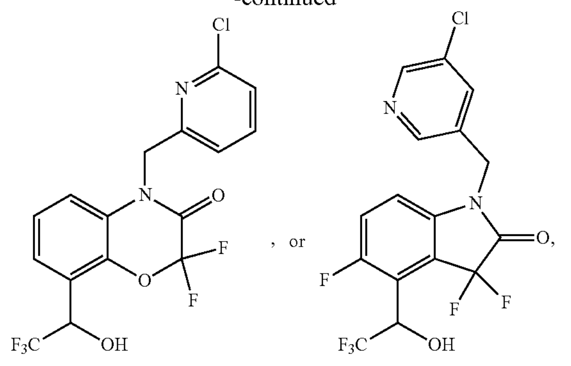

or a pharmaceutically acceptable salt thereof, or a prodrug of the compound or its pharmaceutically acceptable salt.

In some embodiments of the methods and uses disclosed herein, the GlyT1 inhibitor is a compound having a formula of

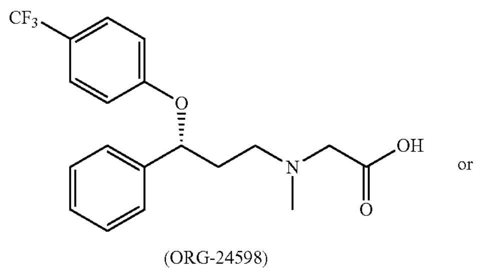

(ORG-24598)

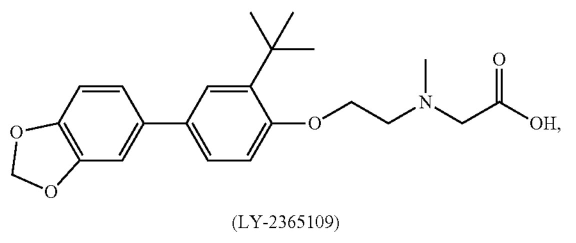

(LY-2365109)

or a pharmaceutically acceptable salt thereof, or a prodrug of the compound or its pharmaceutically acceptable salt.

In some embodiments of the methods and uses disclosed herein, the GlyT1 inhibitor is a compound having a formula of Formula IX

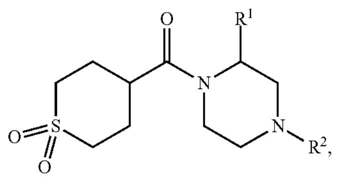

wherein:

$R^1$ represents phenyl or a 5 or 6 membered monocyclic heteroaryl having 1, 2, or 3 heteroatoms independently selected from O, N or S, wherein the phenyl or the heteroaryl is optionally substituted with one or more $R^3$;

$R^2$represents aryl, a 5 or 6 membered monocyclic heteroaryl or a 8 to 10 membered bicyclic heteroaryl, the mono- or bicyclic heteroaryl having 1, 2, or 3 heteroatoms independently selected from O, N or S, wherein the aryl or the heteroaryl is optionally substituted with one or more $R^4$;

$R^3$ is a halogen, a $C_{1-4}$-alkyl or a $C_{3-6}$-cycloalkyl, wherein the $C_{1-4}$-alkyl or the $C_{3-6}$-cycloalkyl is optionally substituted with one or more halogens; and $R^4$ is a halogen, —CN, $C_{1-4}$-alkyl, $C_{3-6}$-cycloalkyl, —$C_{1-3}$-alkyl —$C_{3-6}$-cycloalkyl or —O—$C_{1-6}$ alkyl, wherein the $C_{1-4}$-alkyl, $C_{3-6}$-cycloalkyl, —$C_{1-3}$-alkyl —$C_{3-6}$-cycloalkyl or the —O—$C_{1-6}$-alkyl is optionally substituted with one or more halogens;

or a pharmaceutically acceptable salt thereof, or a tautomer or stereoisomer of the compound or its pharmaceutically acceptable salt, or a mixture of any of the foregoing.

In certain embodiments, the compound of Formula IX can be represented by a compound of formula IX(a):

Formula IX(a)

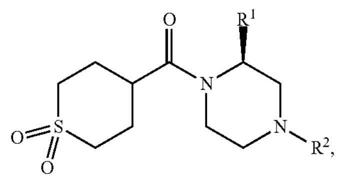

or a pharmaceutically acceptable salt thereof, or a tautomer the compound or its pharmaceutically acceptable salt, or a mixture of any of the foregoing.

In certain embodiments, the compound of Formula IX can be represented by a compound of formula IX(b):

Formula IX(b)

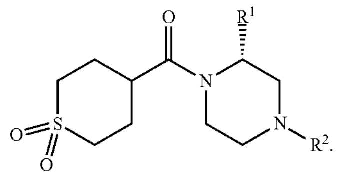

or a pharmaceutically acceptable salt thereof, or a tautomer the compound or its pharmaceutically acceptable salt, or a mixture of any of the foregoing.

In certain embodiments, the compound of formula IX is a compound selected from any of the following, a stereoisomer or stereoisomeric mixture thereof, or a pharmaceutically acceptable salt thereof:

-continued
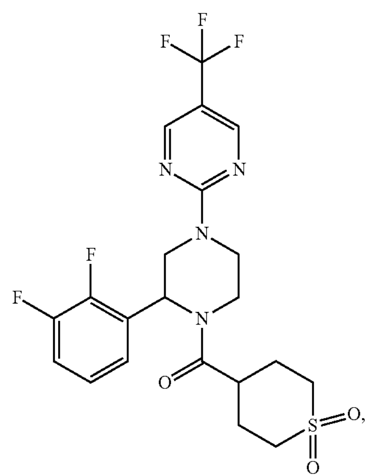
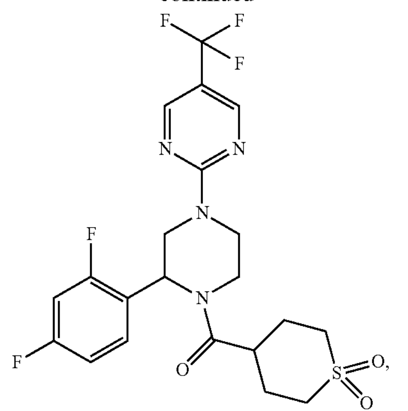
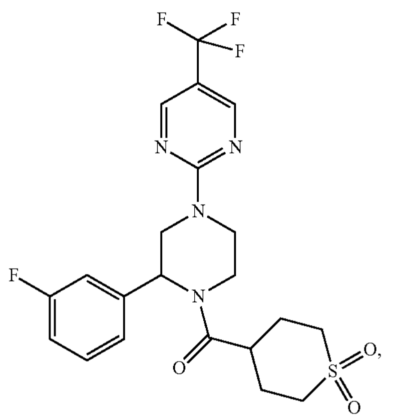
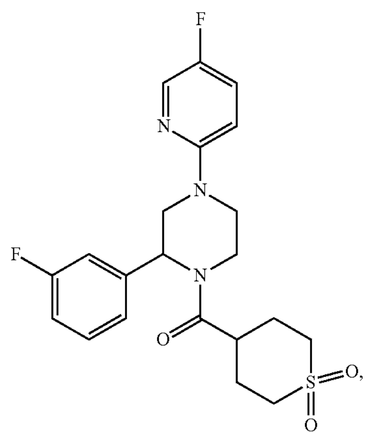
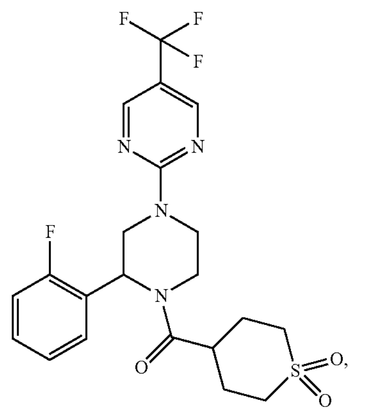
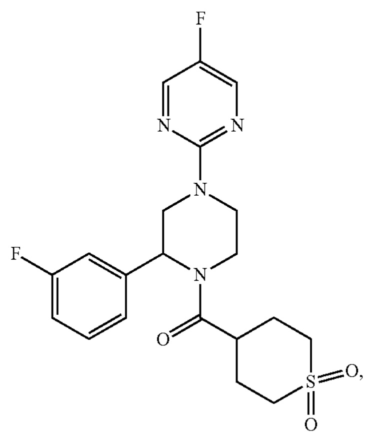
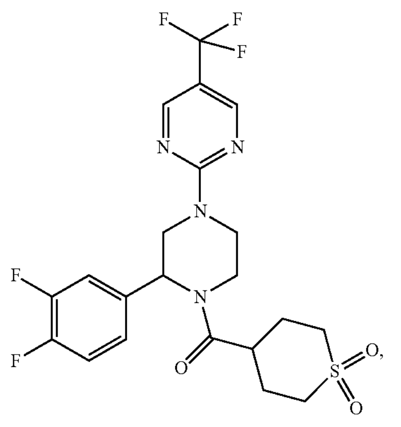
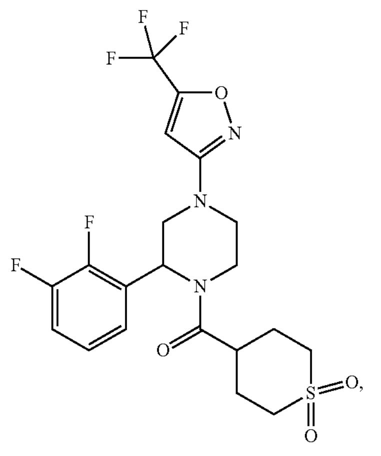

-continued
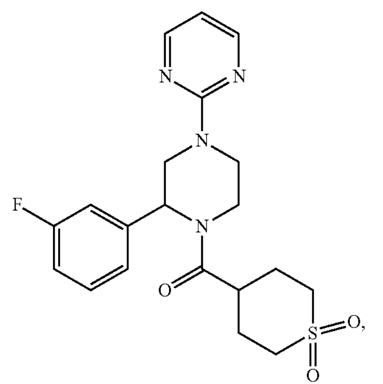
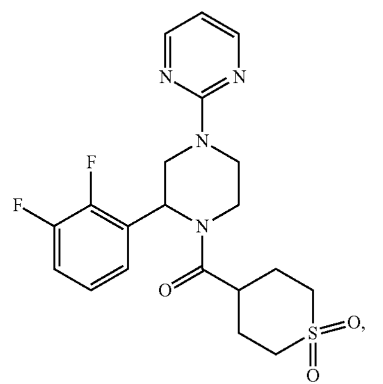
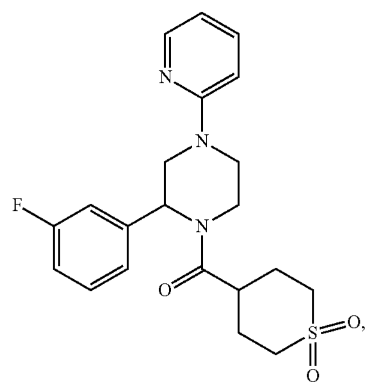
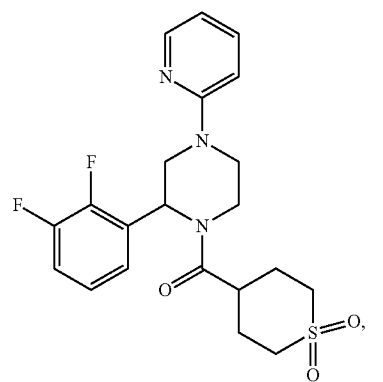
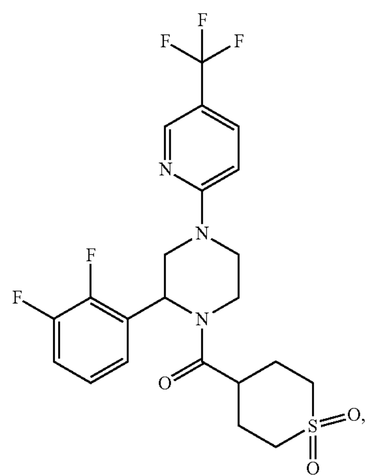
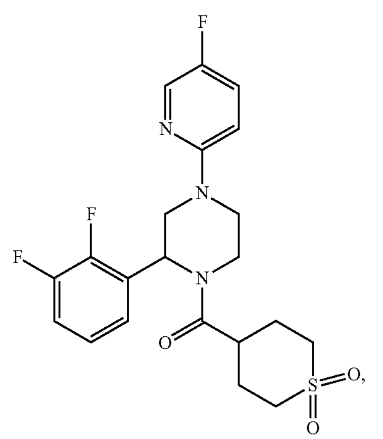
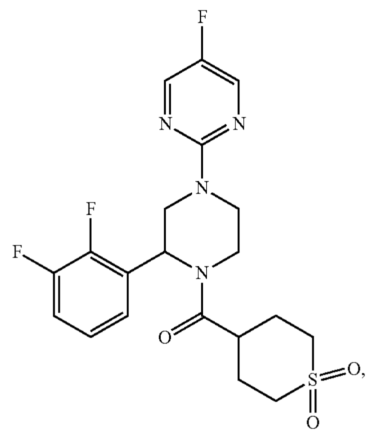
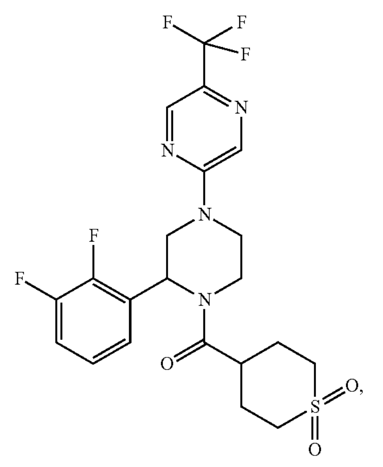

-continued
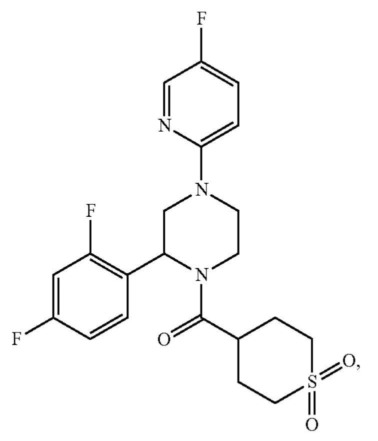
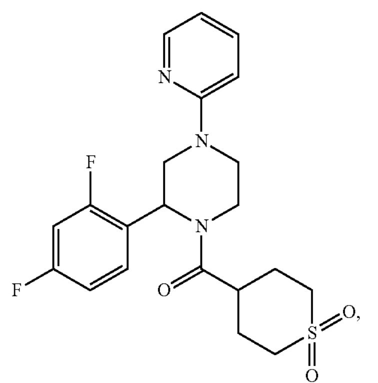
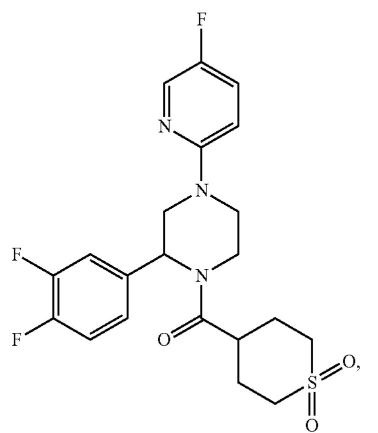
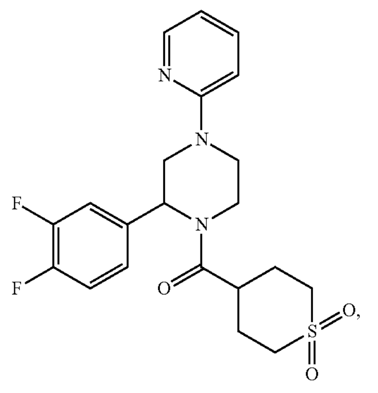
-continued
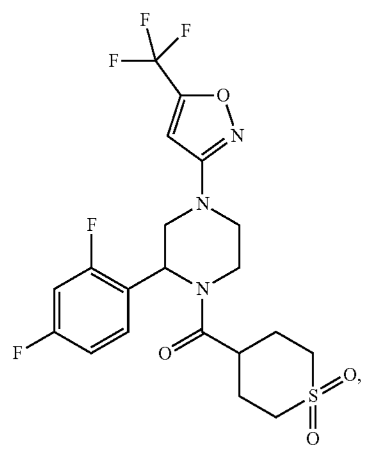
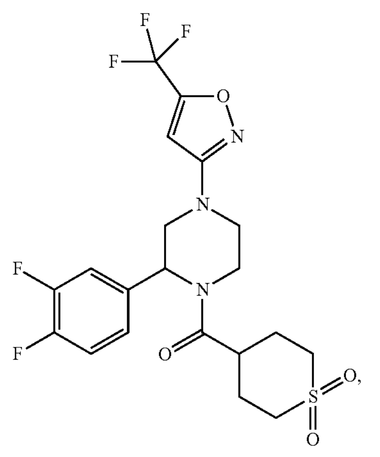
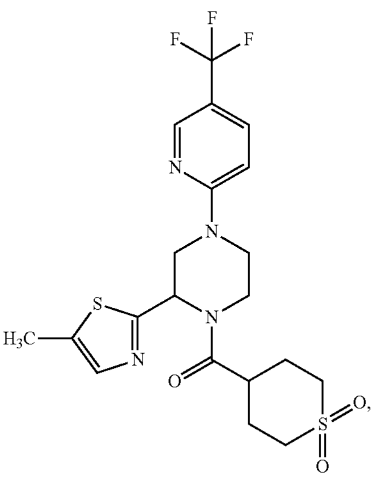

-continued
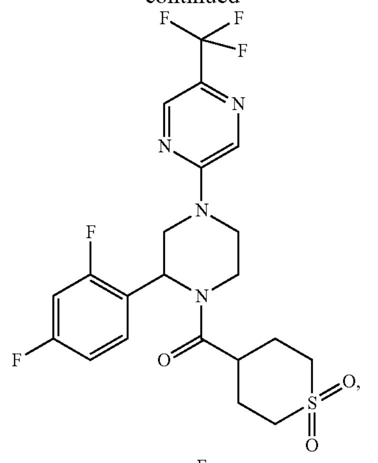
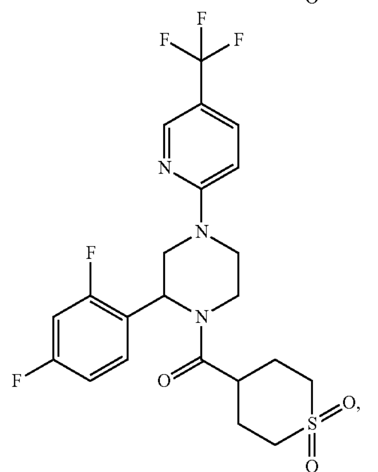
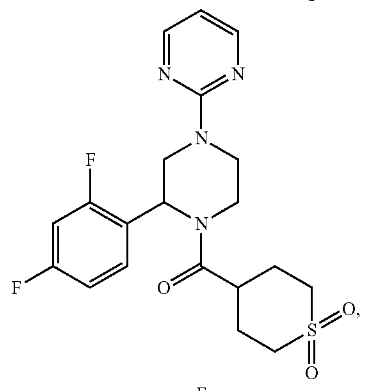
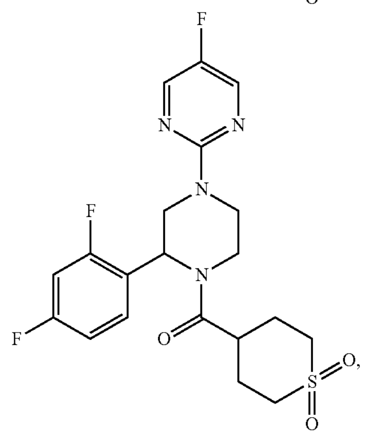
-continued
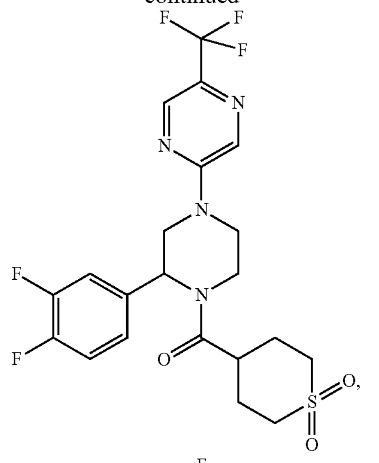
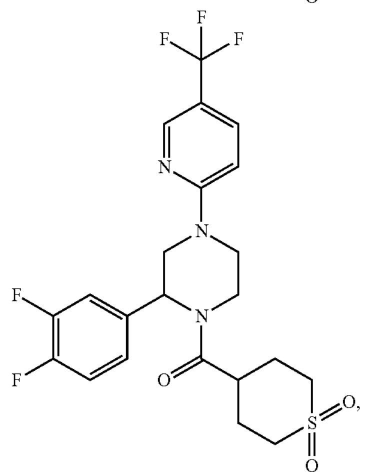
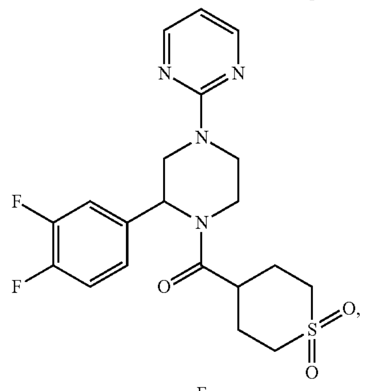
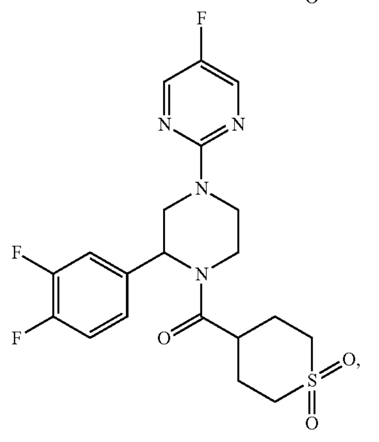

-continued
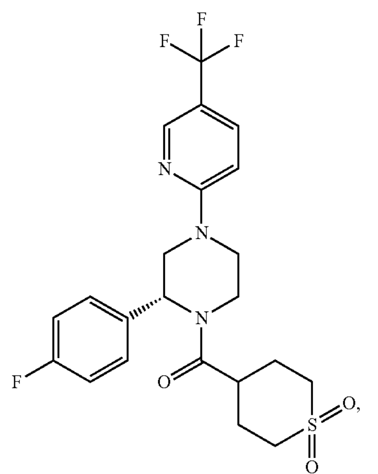
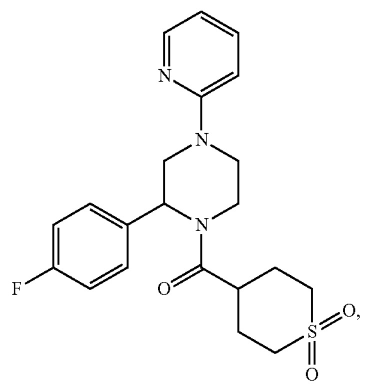
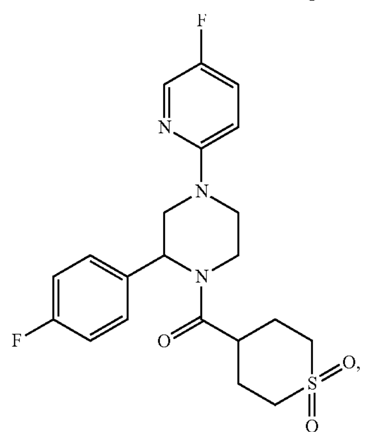
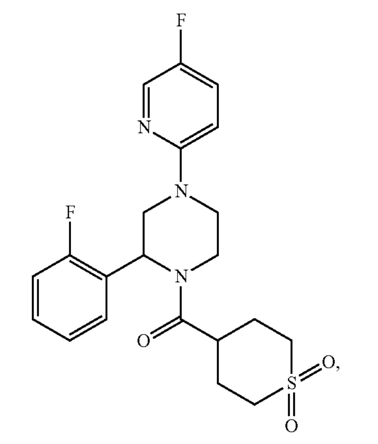
-continued
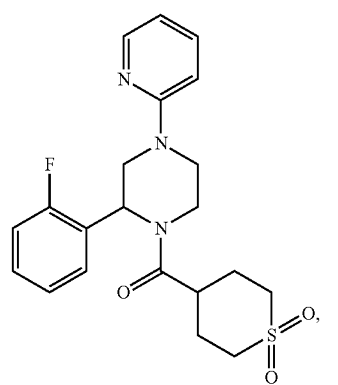
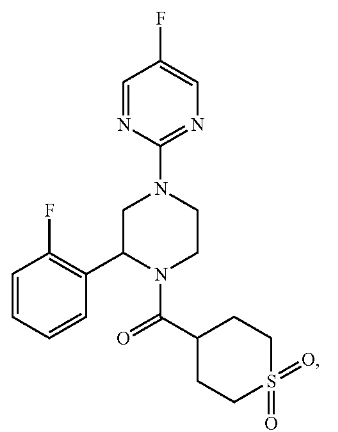
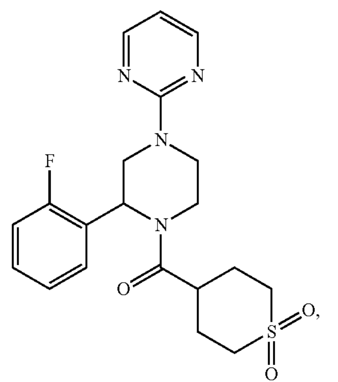
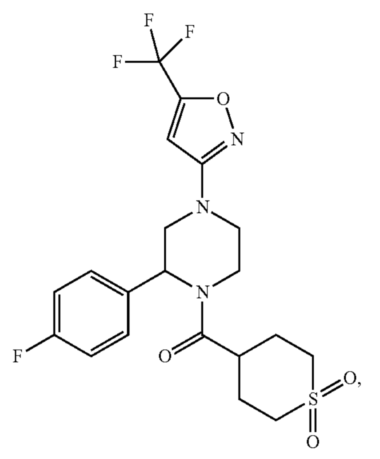

-continued
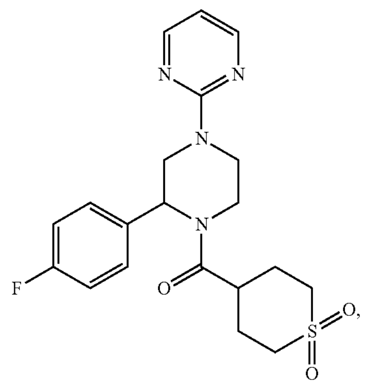
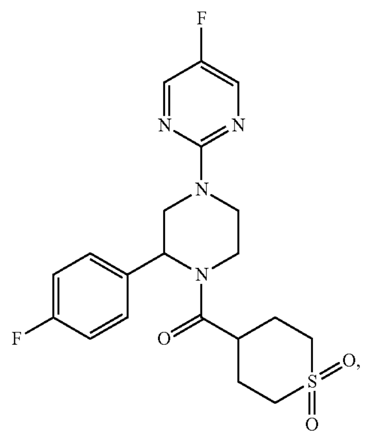
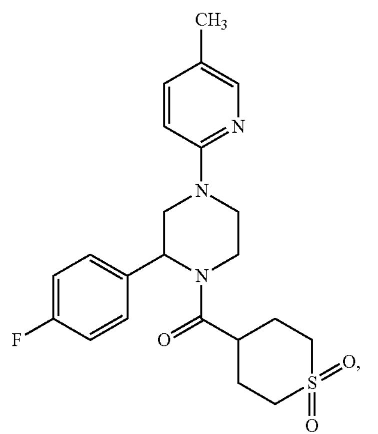
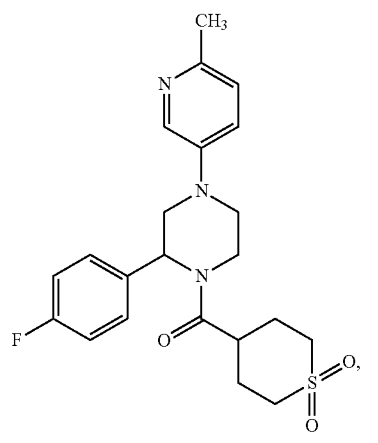
-continued
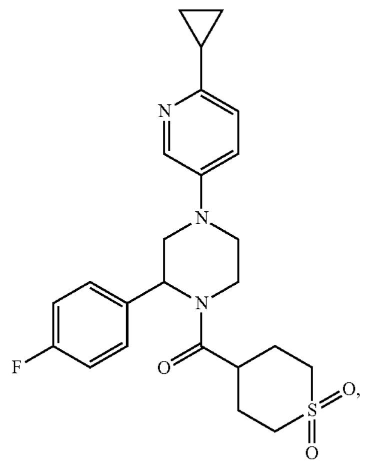
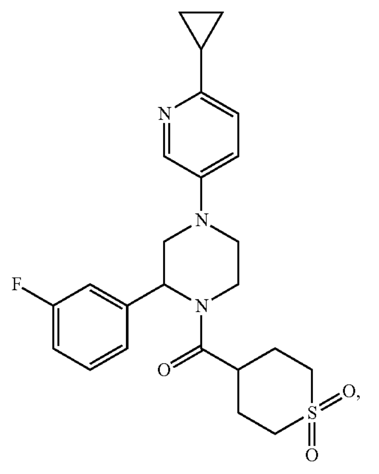
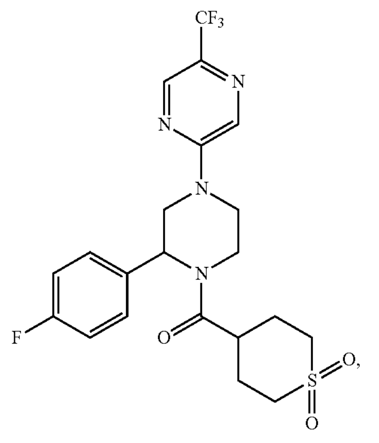

-continued
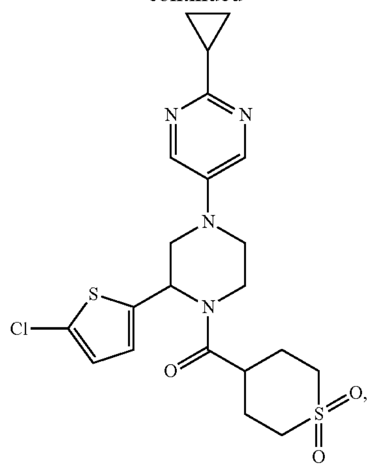
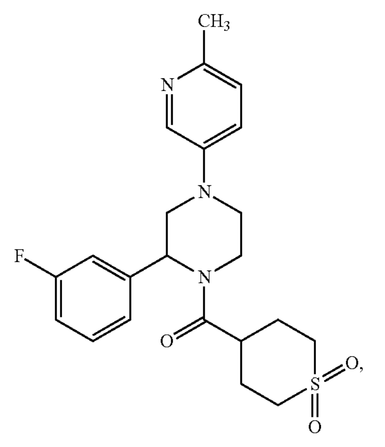
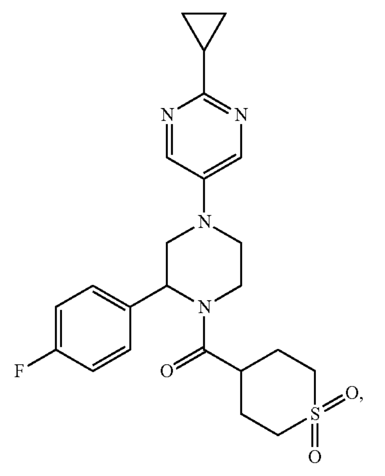
-continued
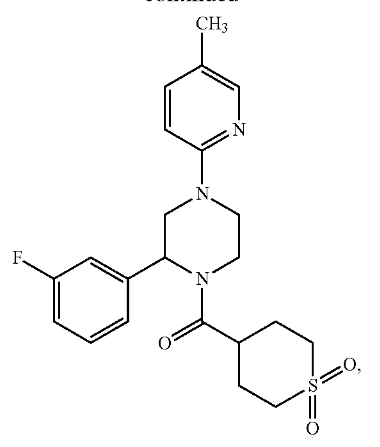
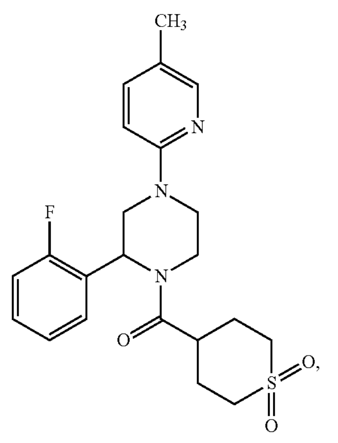
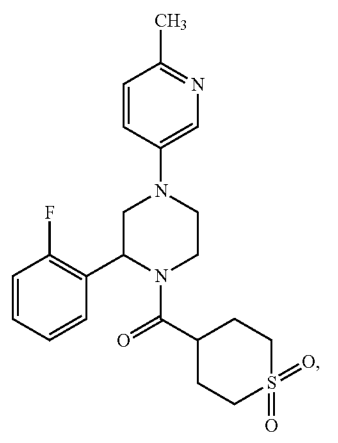

-continued
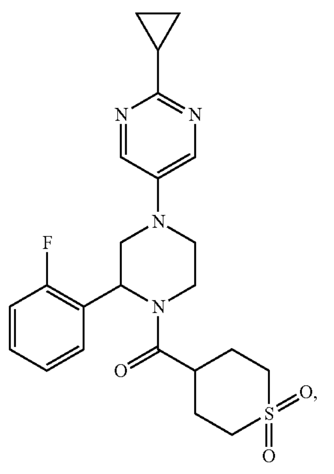
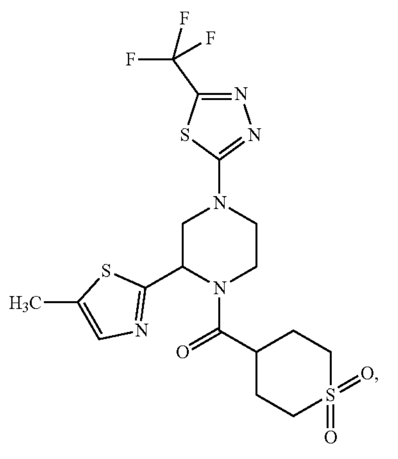
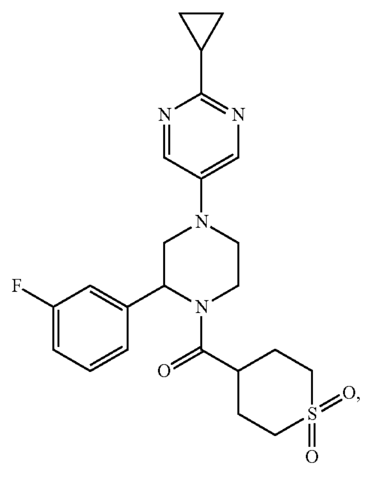
-continued
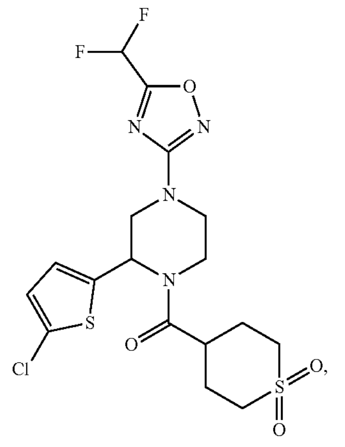
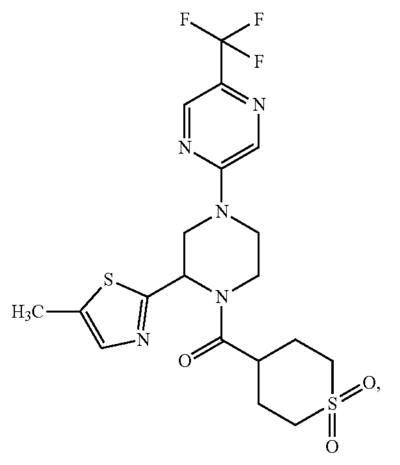
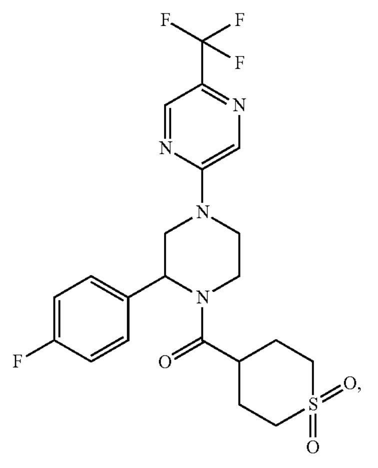

-continued
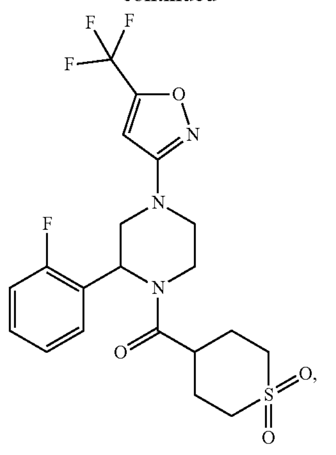
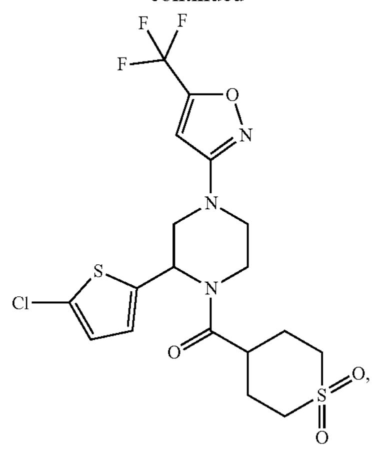
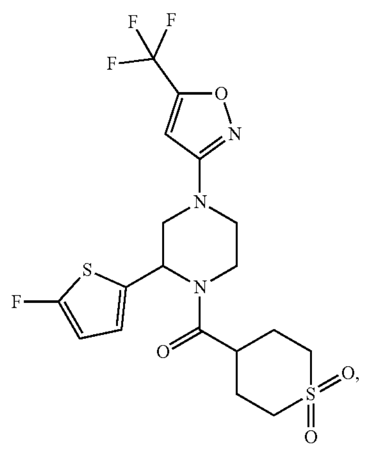
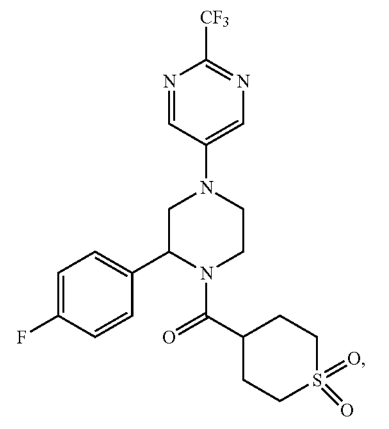
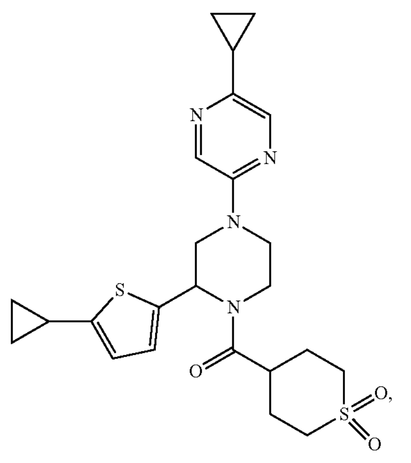
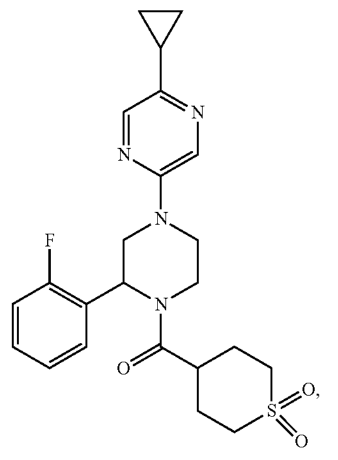

-continued
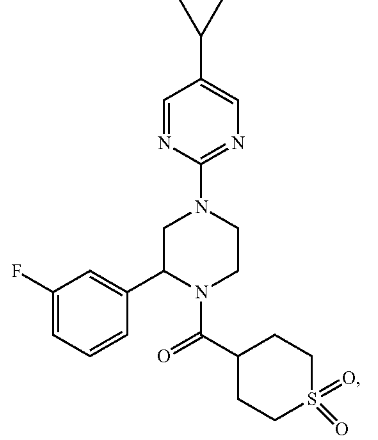
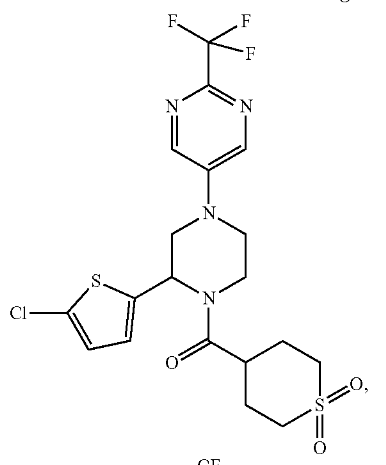
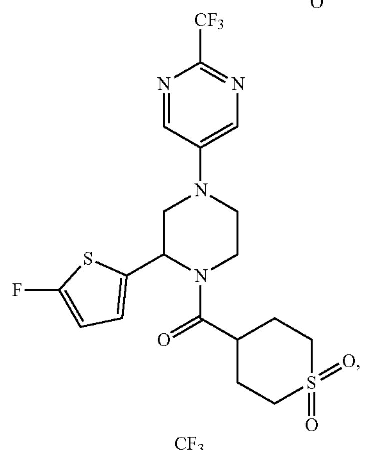
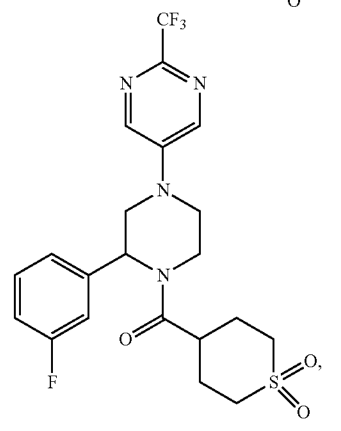
-continued
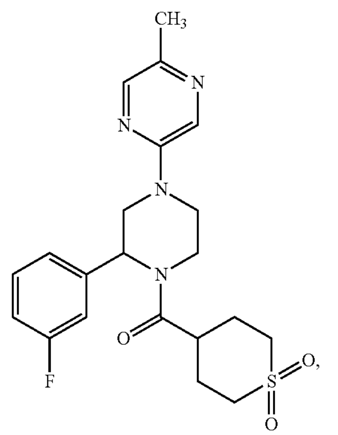
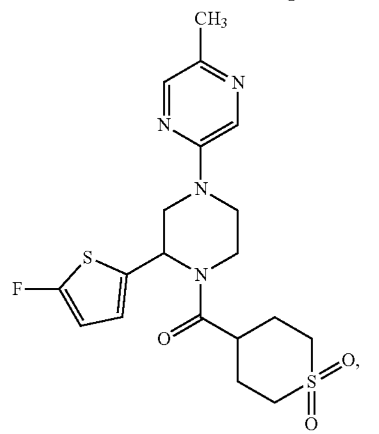
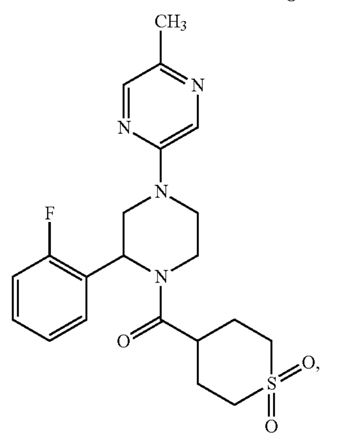
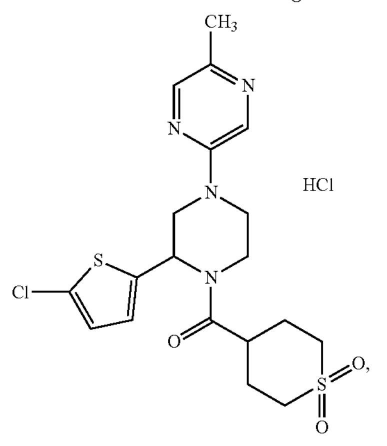

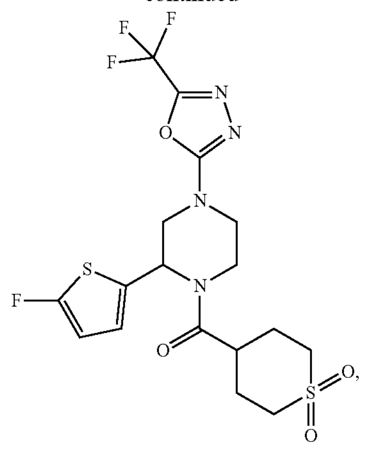
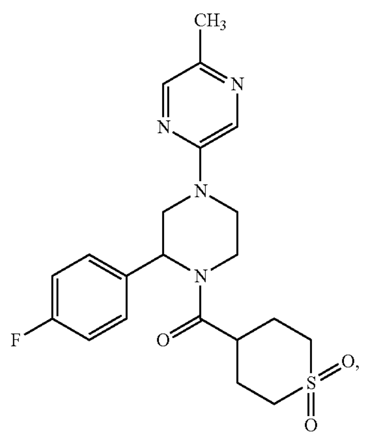
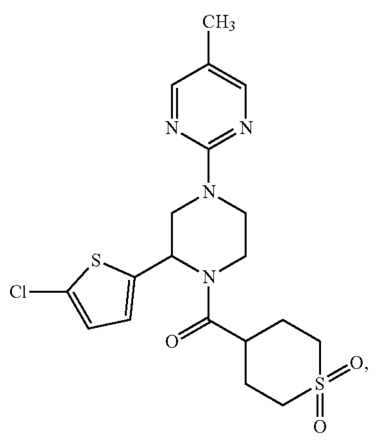
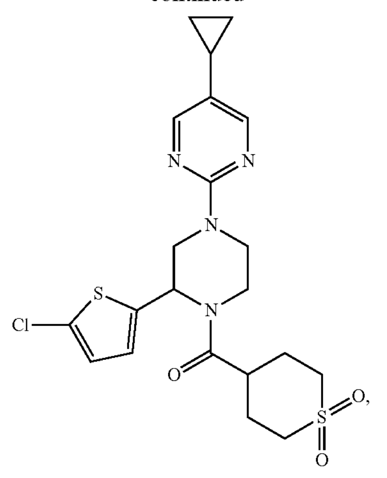
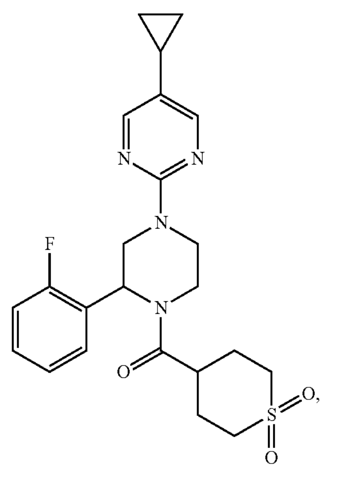
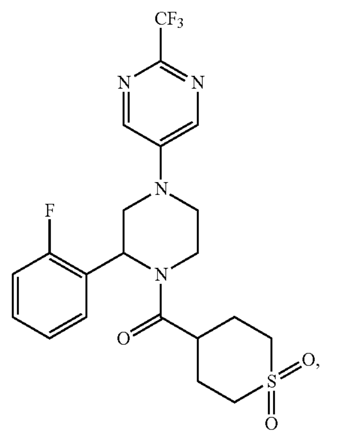

-continued
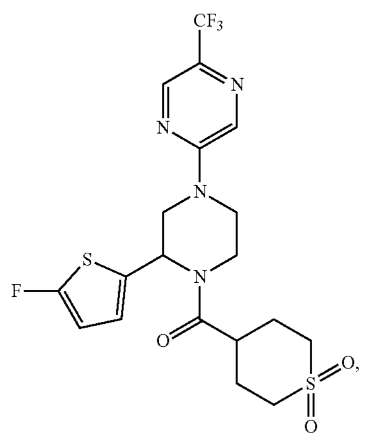
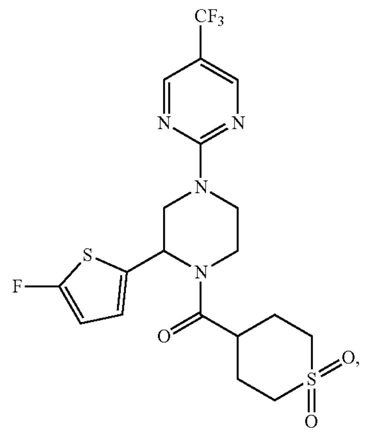
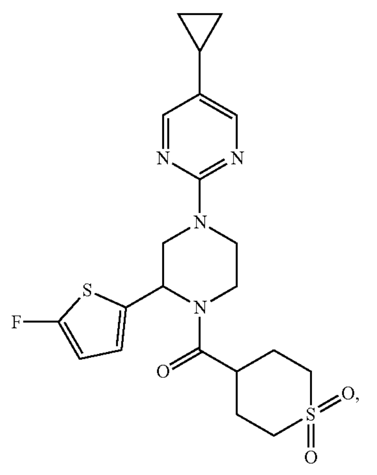
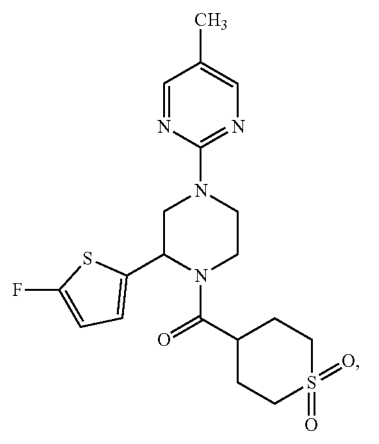
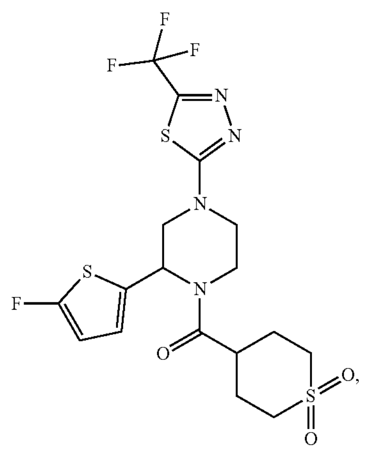
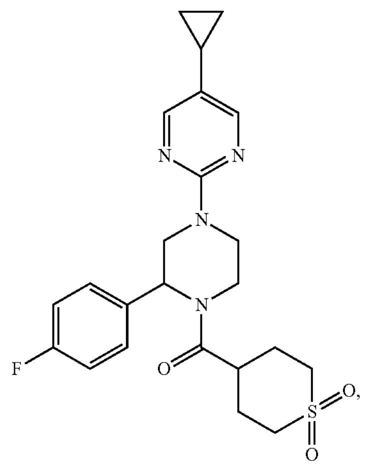

-continued
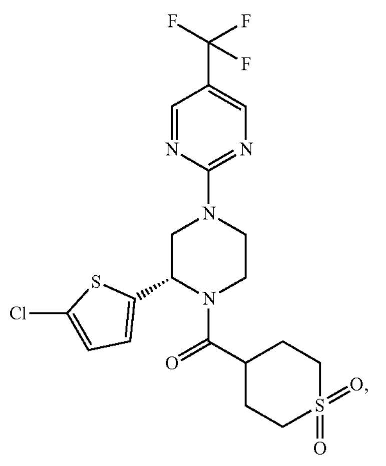
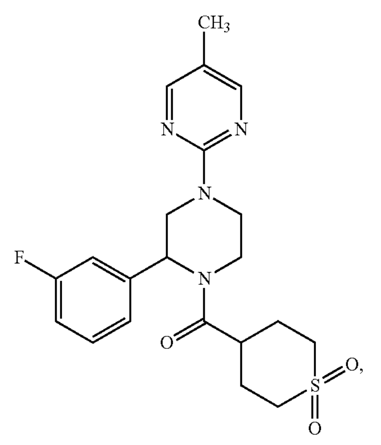
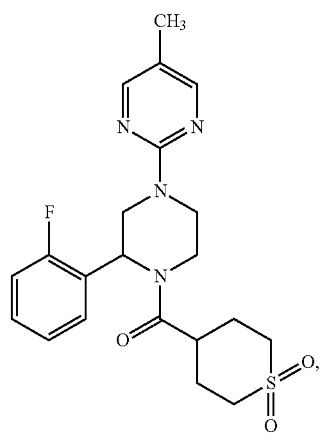
-continued
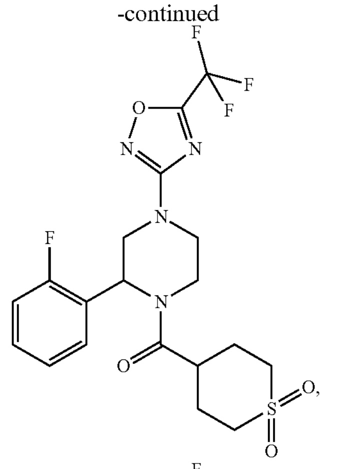
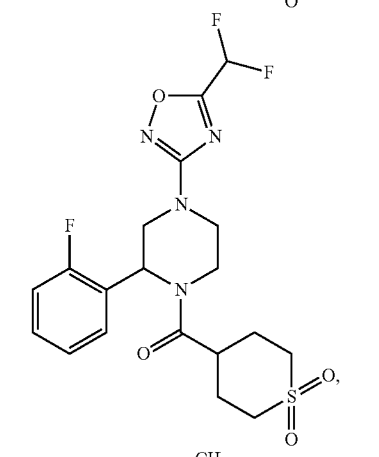
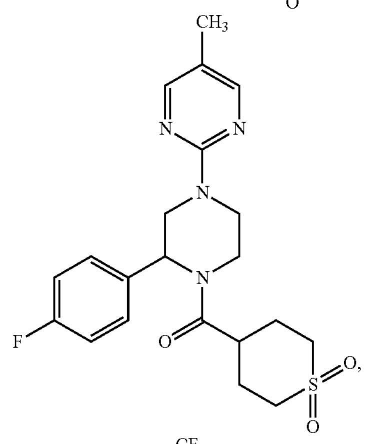
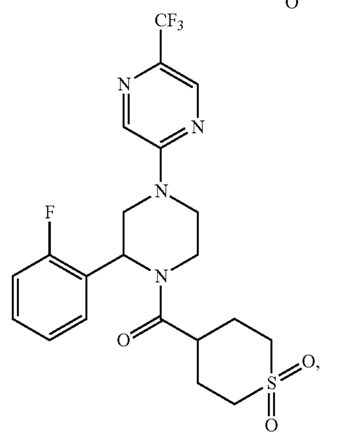

-continued
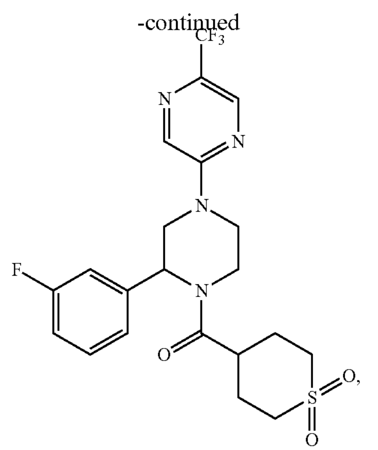
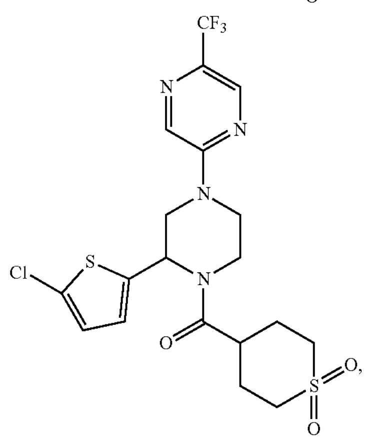
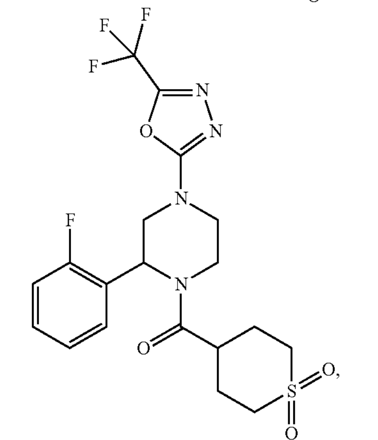
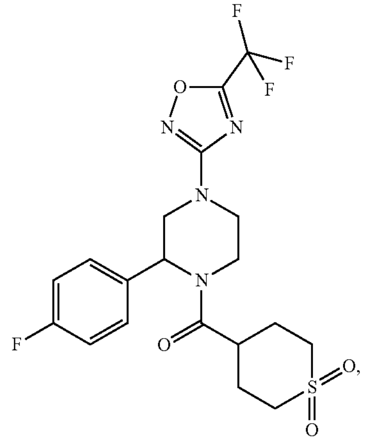
-continued
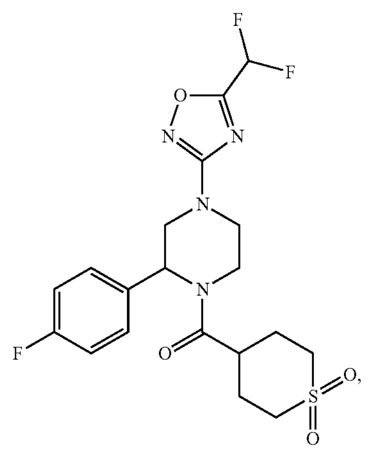
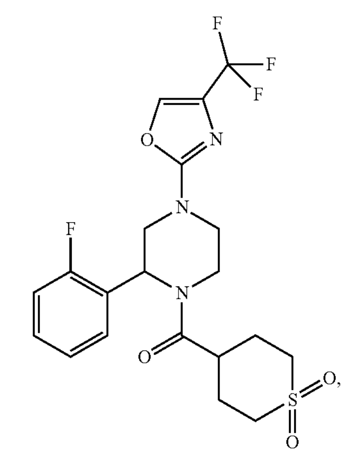
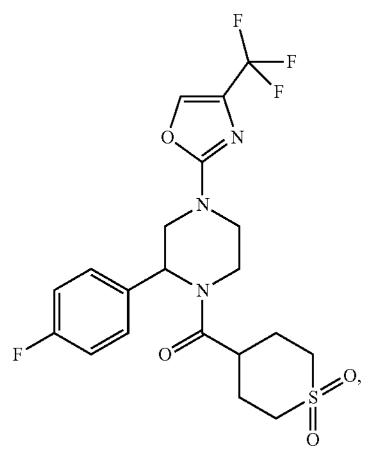

-continued
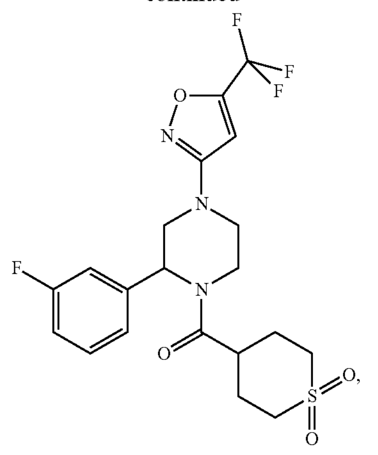
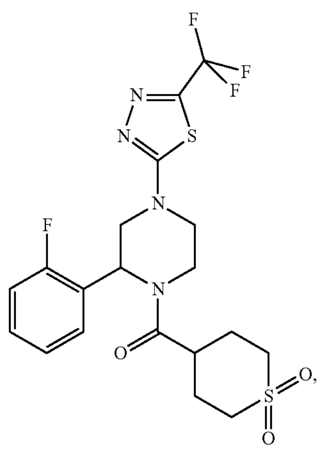
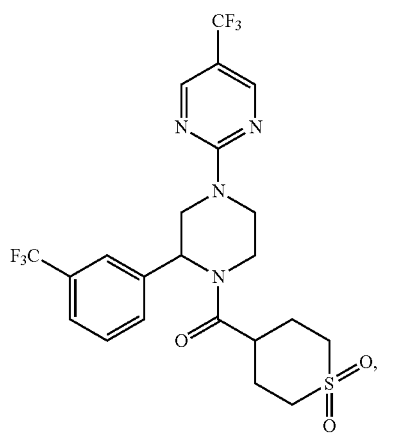
-continued
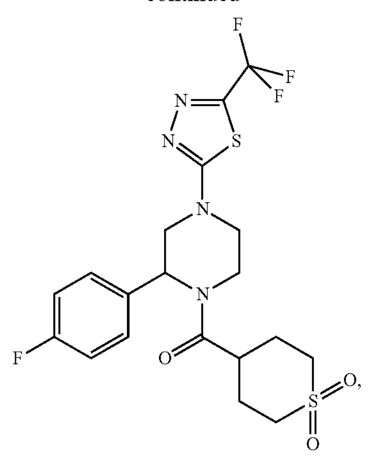
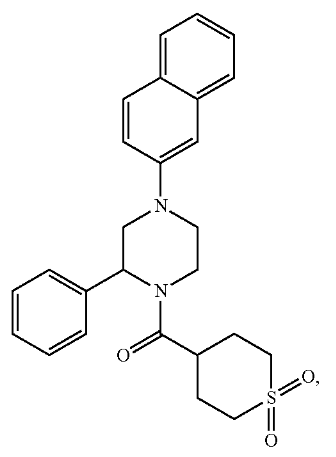
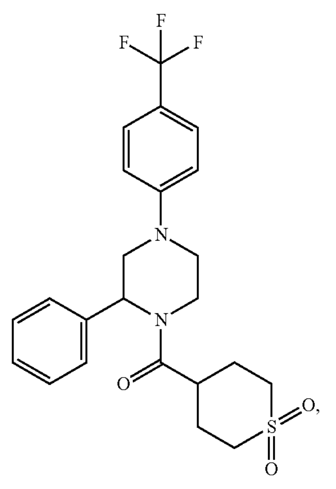

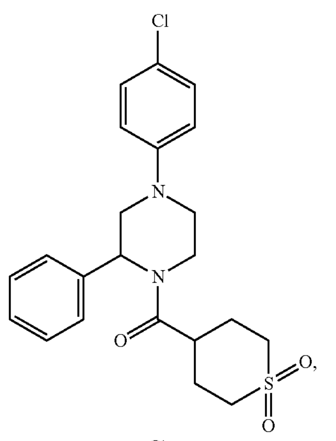
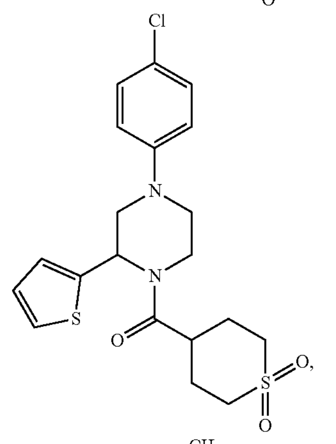
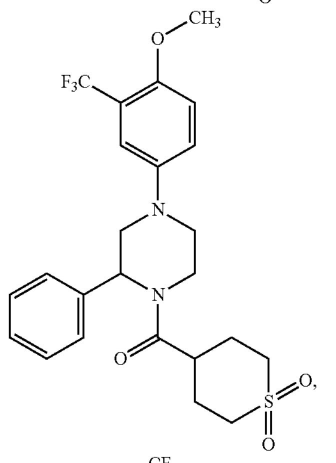
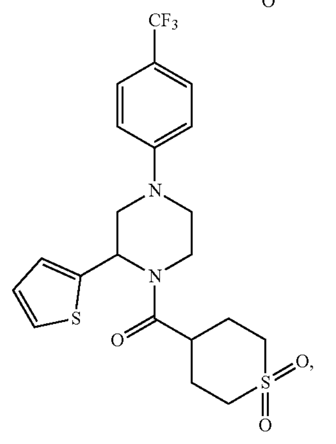
-continued
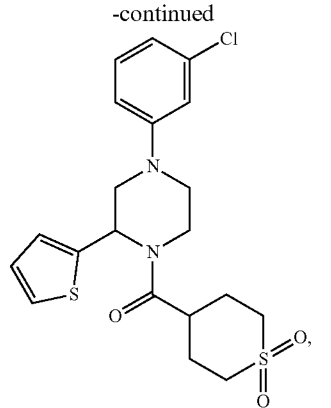
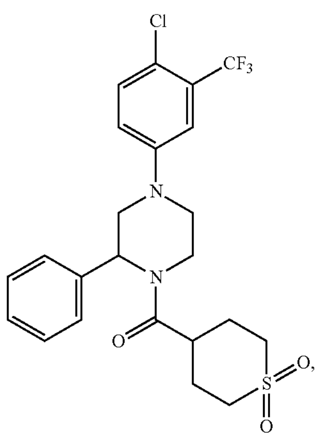
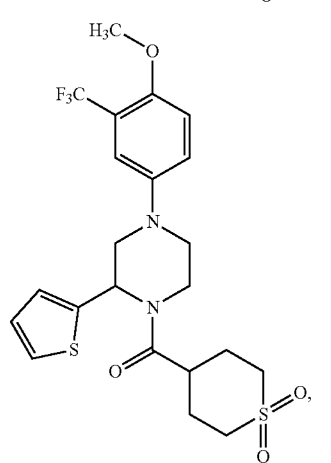
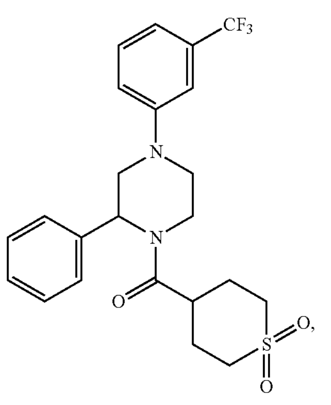

-continued
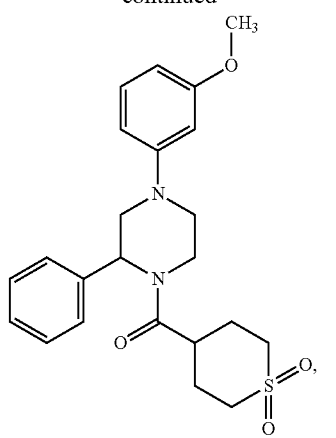
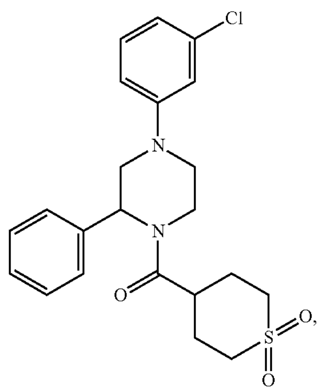
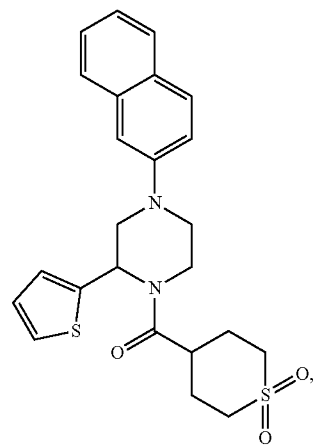
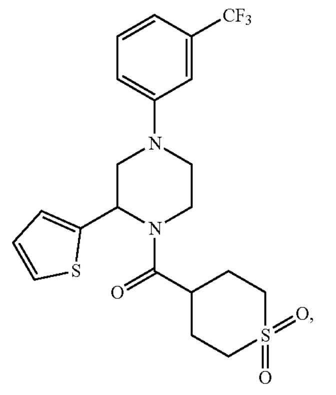
-continued
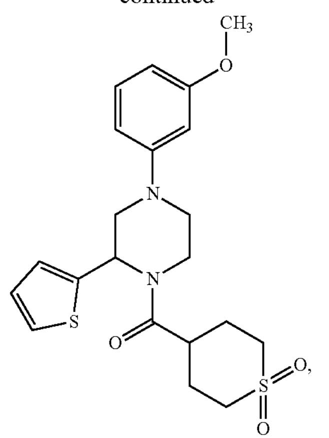
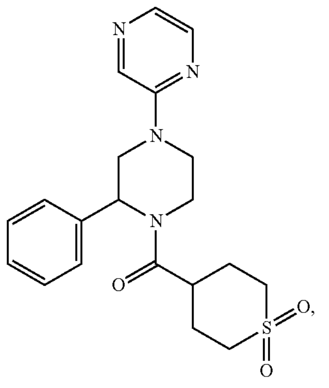
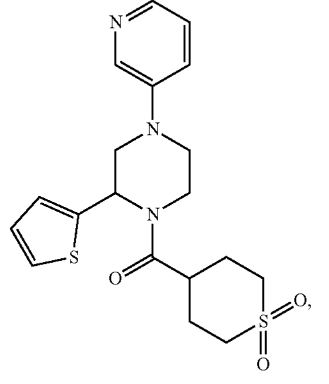
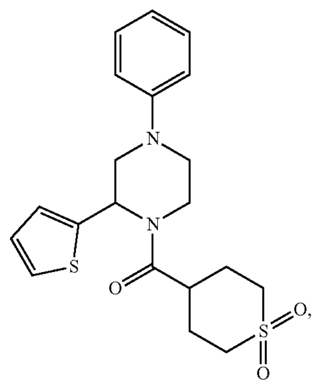

-continued
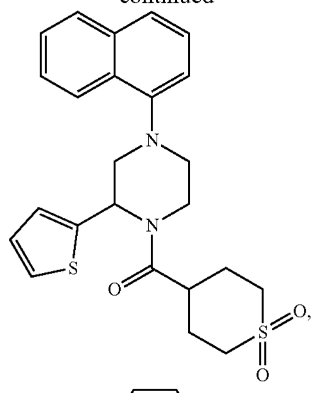
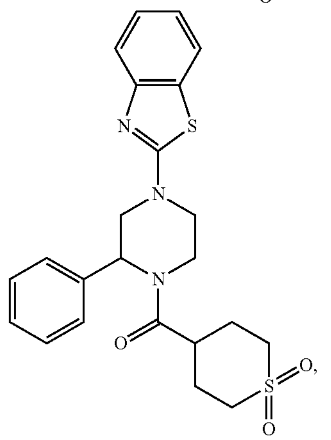
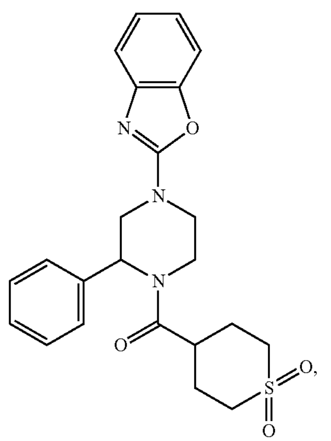
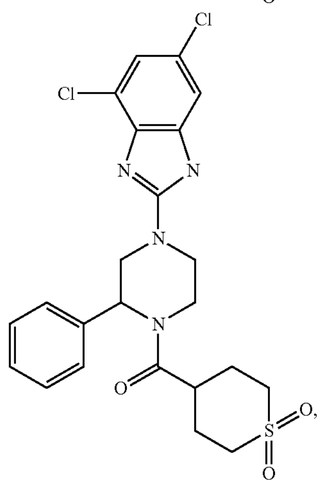
-continued
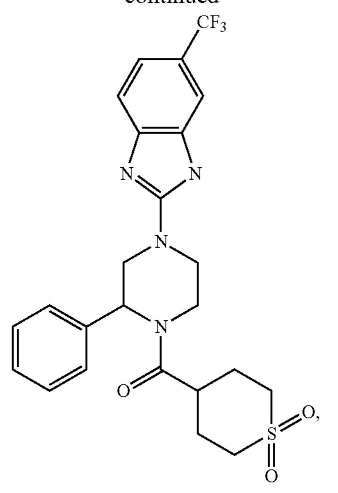
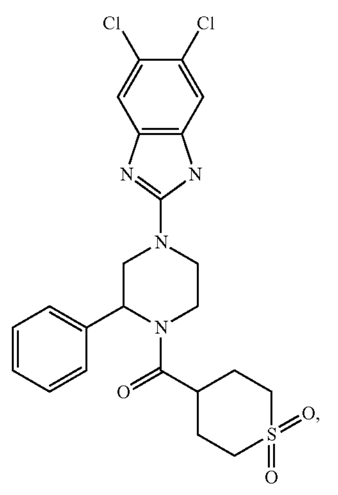
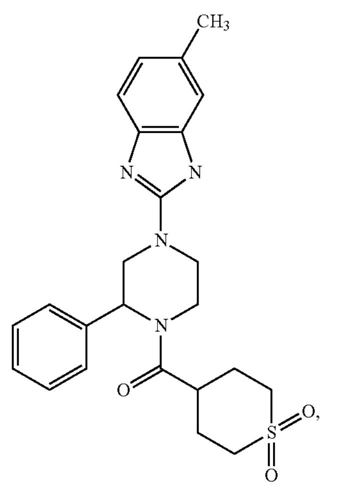

-continued
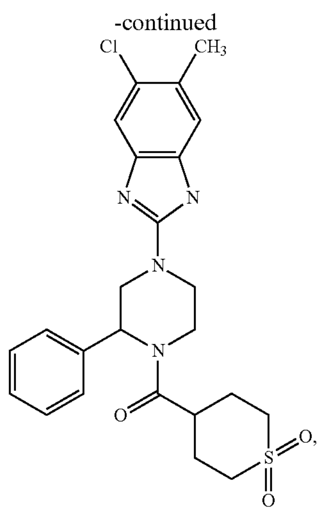
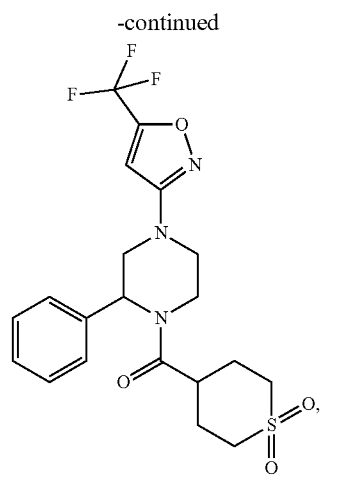
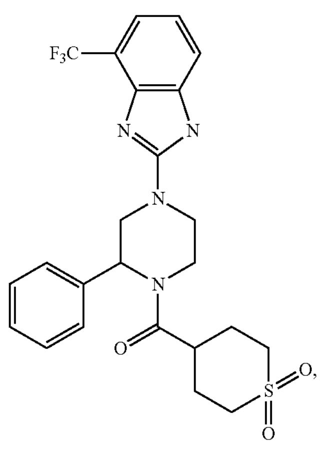
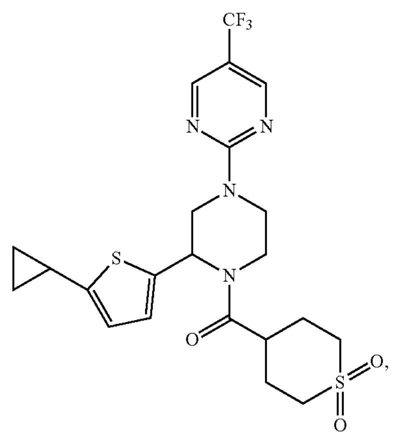
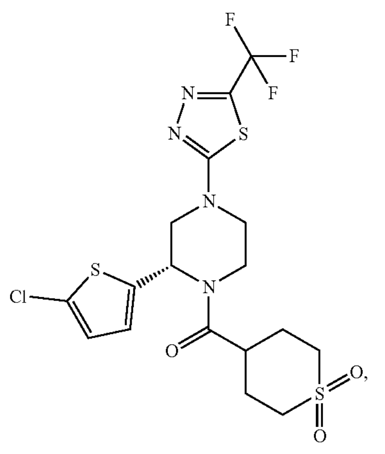
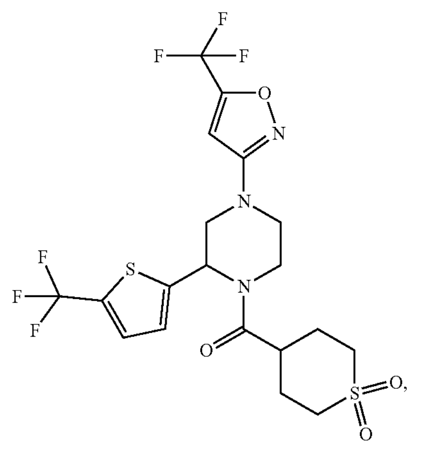

-continued
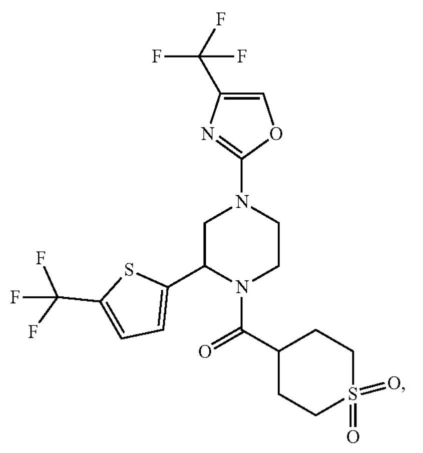
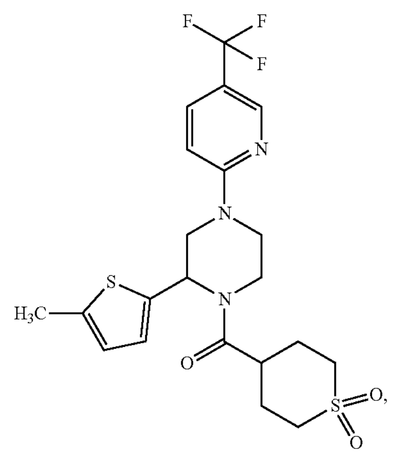
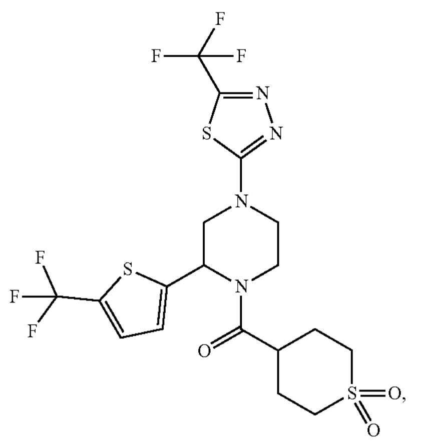
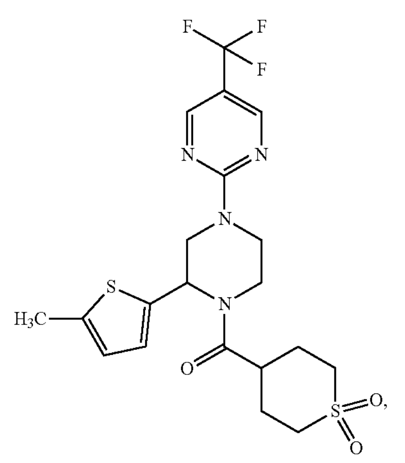
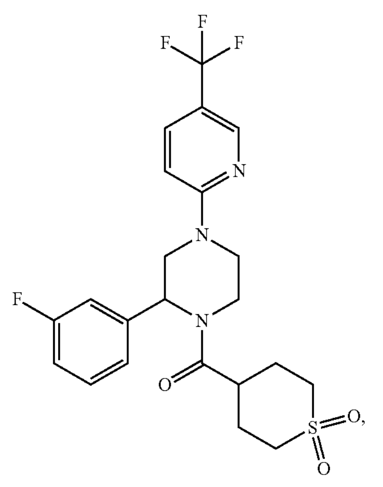
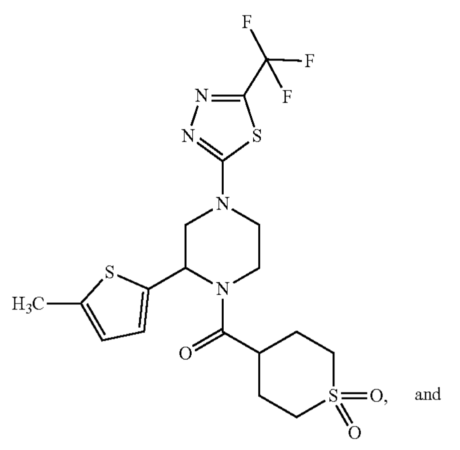
and -continued

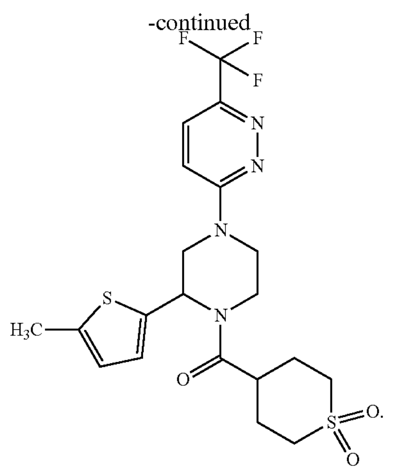

In some embodiments of the methods and uses disclosed herein, the GlyT1 inhibitor is a compound having a formula of Formula X

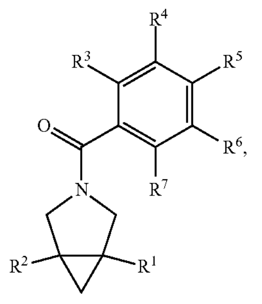

wherein:

$R^1$ is selected from the group consisting of a) 5 or 6 membered monocyclic heteroaryl, having 1, 2, 3 or 4 heteroatoms independently selected from the group consisting of O, N and S(O)r, b) 5 or 6 membered monocyclic partially saturated heterocycloalkyl, having 1, 2 or 3 heteroatoms independently selected from the group consisting of O, N and S(O)r, and c) 9 or 10 membered bicyclic heteroaryl, having 1, 2 or 3 heteroatoms independently selected from the group consisting of O, N and $S(O)_r$, wherein r is 0, 1 or 2;

wherein each of said groups a), b) and c) is optionally substituted with 1 or more substituents independently selected from the group consisting of $C_{1-4}$-alkyl-, $C_{1-4}$-alkyl-O—, oxetanyl, tetrahydrofuranyl, tetrahydropyranyl, $C_{3-6}$-cycloalkyl- and $C_{3-6}$-cycloalkyl-O— and in case a substituent is attached to a nitrogen ring atom said substituent is selected from the group consisting of $C_{1-4}$-alkyl-, $C_{1-4}$-alkyl-CO—, $C_{3-6}$-cycloalkyl- and $C_{3-6}$-cycloalkyl-CO—, and wherein each of said $C_{1-4}$-alkyl-, $C_{1-4}$-alkyl-O—, $C_{1-4}$-alkyl-CO—, oxetanyl, tetrahydrofuranyl, tetrahydropyranyl, $C_{3-6}$-cycloalkyl-, $C_{3-6}$-cycloalkyl-CO— or $C_{3-6}$-cycloalkyl-O— substituents may be substituted by 1 or more substituents independently selected from the group consisting of fluoro, —$CF_3$, —$CHF_2$, —$CH_2F$ and —CN;

$R^2$ is selected from the group consisting of hydrogen, $C_{1-4}$-alkyl-, $C_{1-4}$-alkyl-O—, CN and $C_{3-6}$-cycloalkyl-, wherein each of said $C_{1-4}$-alkyl-, $C_{1-4}$-alkyl-O— and $C_{3-6}$-cycloalkyl-group may be optionally substituted with 1, 2, 3 or more substituents independently selected from the group consisting of fluoro, —$CF_3$, —$CHF_2$, —$CH_2F$ and —CN;

$R^3$ is selected from the group consisting of $C_{1-6}$-alkyl-O—, $C_{3-6}$-cycloalkyl-O—, morpholino, pyrazolyl and a 4 to 7 membered, monocyclic heterocycloalkyl-O with 1 oxygen atom as ring member and optionally 1 or 2 heteroatoms independently selected from the group consisting of O, N and S(O)s with s=0, 1 or 2, wherein said $C_{1-6}$-alkyl-O— and said $C_{3-6}$-cycloalkyl-O— may be optionally substituted with 1, 2, 3 or more substituents independently selected from the group consisting of fluoro, —$CF_3$, —$CHF_2$, —$CH_2F$, —CN, $C_{1-4}$-alkyl-, $C_{3-6}$-cycloalkyl-, $C_{1-6}$-alkyl-O— and $C_{3-6}$-cycloalkyl-O—;

$R^4$ is hydrogen;

or $R^3$ and $R^4$ together with the ring atoms of the phenyl group to which they are bound may form a 4, 5 or 6 membered, monocyclic, partially saturated heterocycloalkyl or a heteroaryl each of which having 1, 2 or 3 heteroatoms independently selected from the group consisting of O, N and $S(O)_s$ with s=0, 1 or 2, wherein there must be 1 ring oxygen atom that is directly attached to the ring carbon atom of said phenyl group to which $R^3$ is attached to in general formula (I);

wherein said heterocycloalkyl group may be optionally substituted with 1, 2, 3 or more substituents independently selected from the group consisting of fluoro, —$CF_3$, —$CHF_2$, —$CH_2F$, —CN, $C_{1-4}$-alkyl-, $C_{3-6}$-cycloalkyl-, $C_{1-6}$-alkyl-O—, $C_{3-6}$-cycloalkyl-O—, oxetanyl-O—, tetrahydrofuranyl-O— and tetrahydropyranyl-O—;

$R^5$ is hydrogen;

$R^6$ is selected from the group consisting of hydrogen, $C_{1-4}$-alkyl-$SO_2$—, $C_{3-6}$-cycloalkyl-$SO_2$ and —CN;

$R^7$ is hydrogen;

or one of the pairs a) $R^6$ and $R^7$ or b) $R^6$ and $R^5$ form together with the ring atoms of the phenyl group to which they are bound, a 5 or 6 membered, partially saturated monocyclic heterocycloalkyl group having 1, 2 or 3 heteroatoms independently selected from the group consisting of O, N and $S(O)_u$ with u=0, 1 or 2, wherein there must be 1 —$SO_2$— member that is directly attached to the ring carbon atom of said phenyl group to which $R^6$ is attached to in general formula (I), wherein said heterocycloalkyl group may be optionally substituted with 1, 2, 3 or more substituents independently selected from the group consisting of fluoro, —$CF_3$, —$CHF_2$, —$CH_2F$, —CN, $C_{1-4}$-alkyl-, $C_{1-6}$-alkyl-O— and $C_{3-6}$-cycloalkyl-O— or a pharmaceutically acceptable salt thereof, or a prodrug of the compound or its pharmaceutically acceptable salt.

In certain embodiments, the compound of formula X is a compound selected from any of the following, a stereoisomer or stereoisomeric mixture thereof, or a pharmaceutically acceptable salt thereof:

-continued
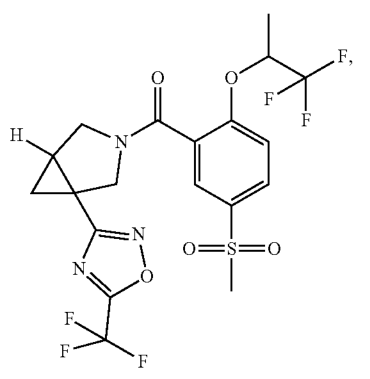
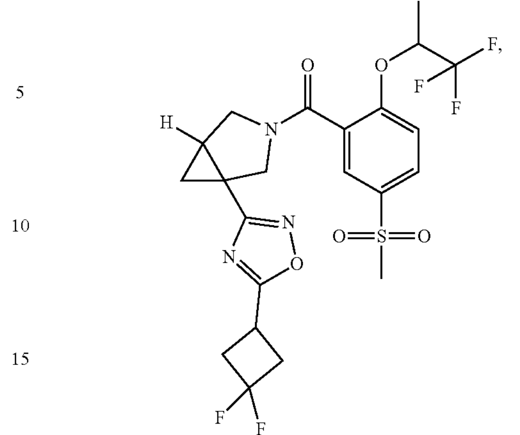
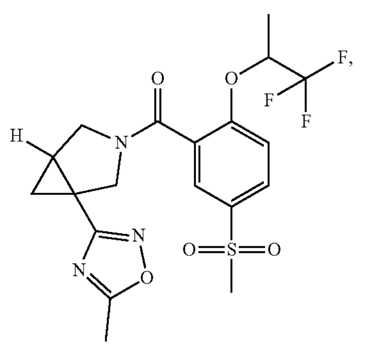
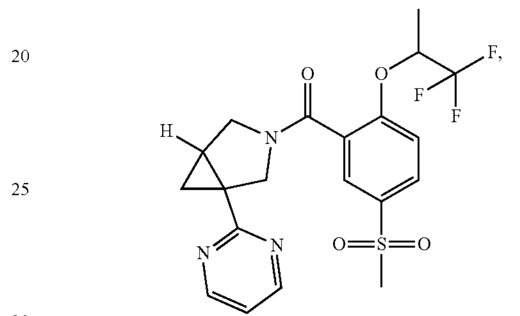
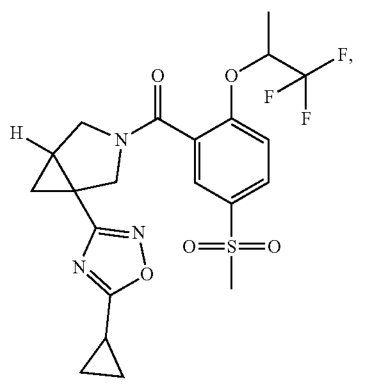
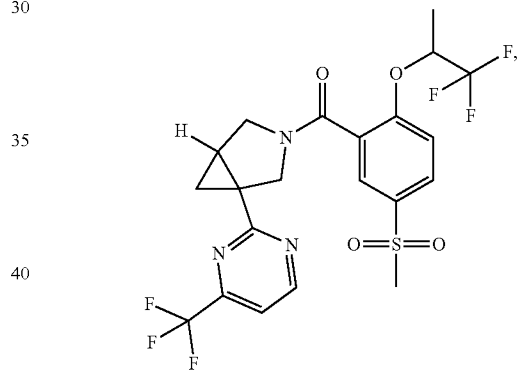
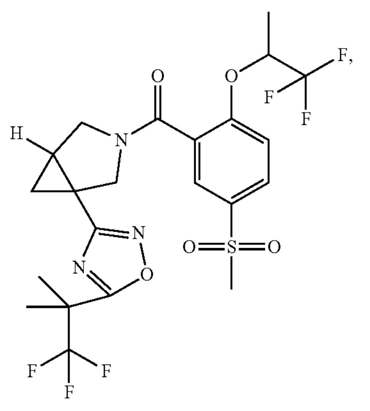
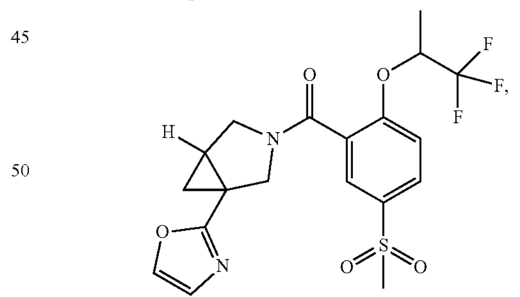
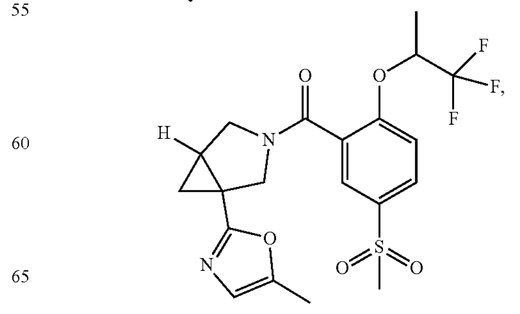

-continued
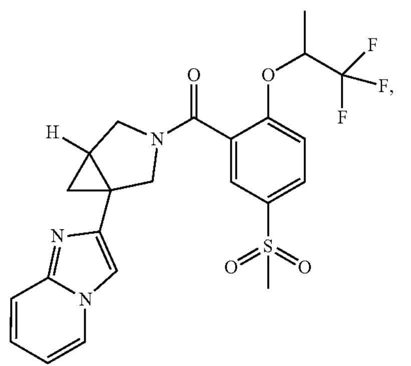
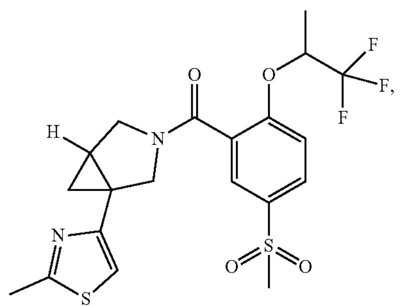
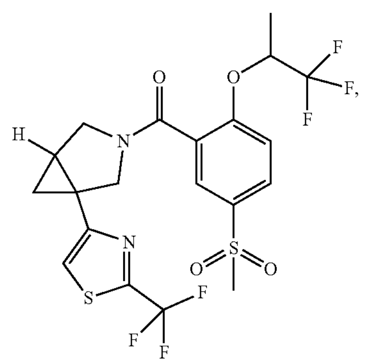
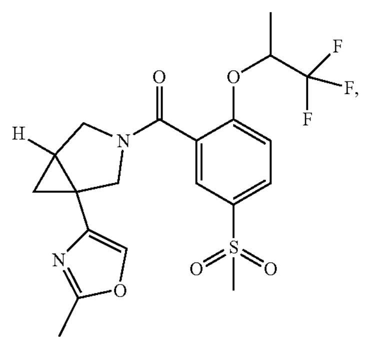
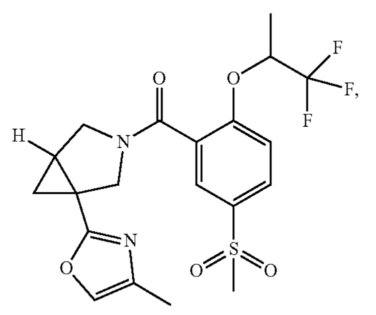
-continued
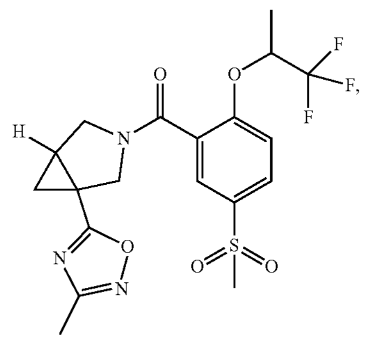
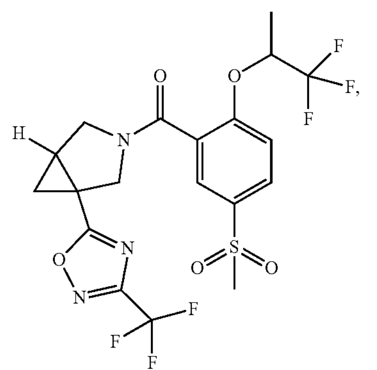
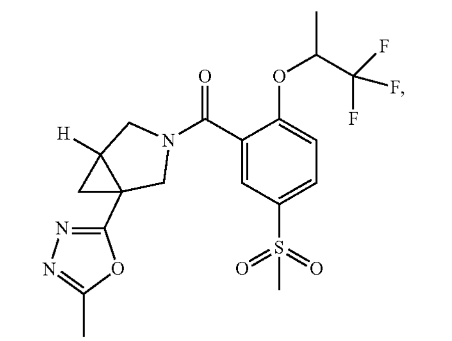
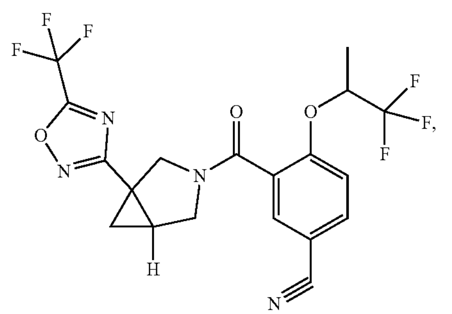
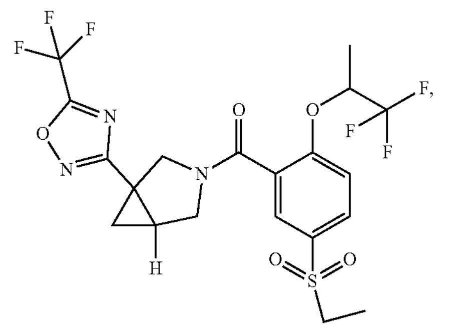

-continued
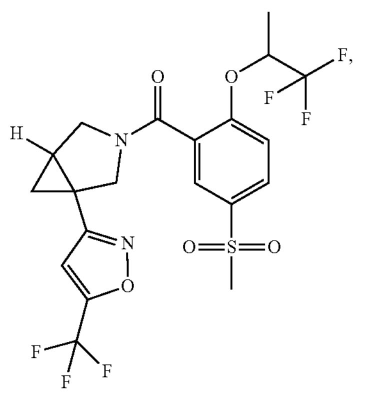
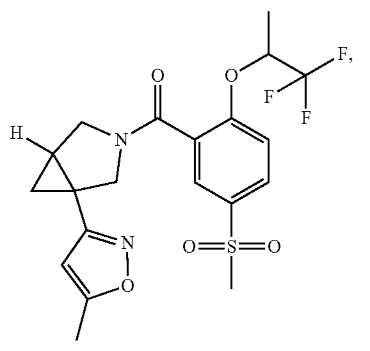
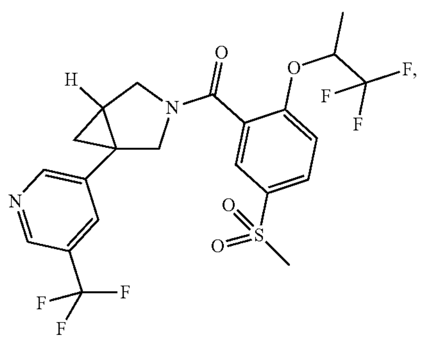
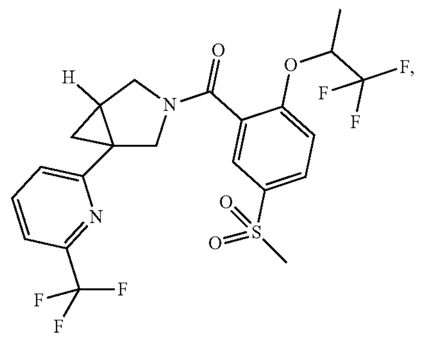
-continued
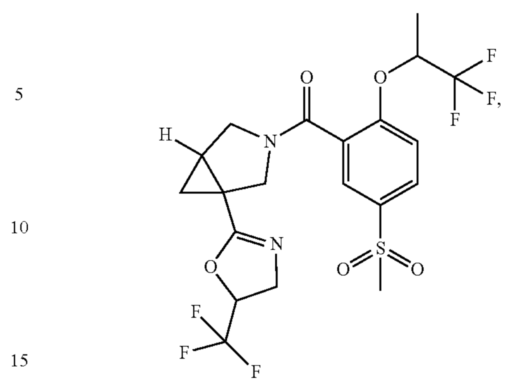
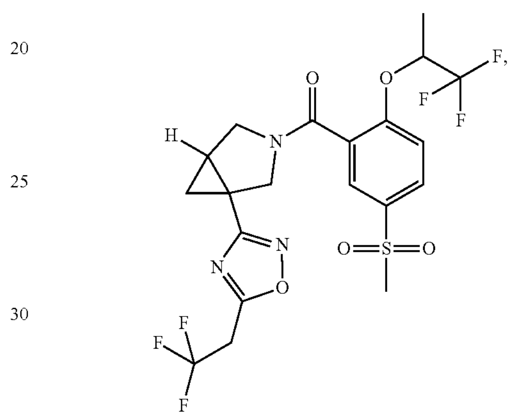
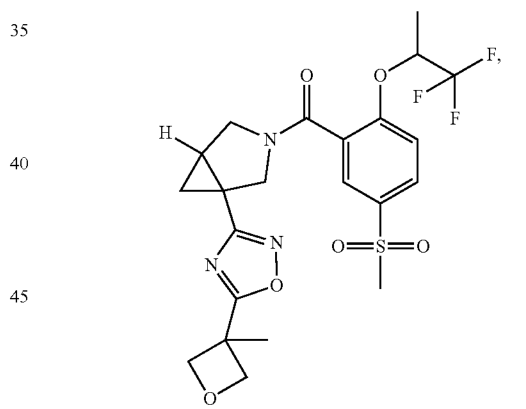
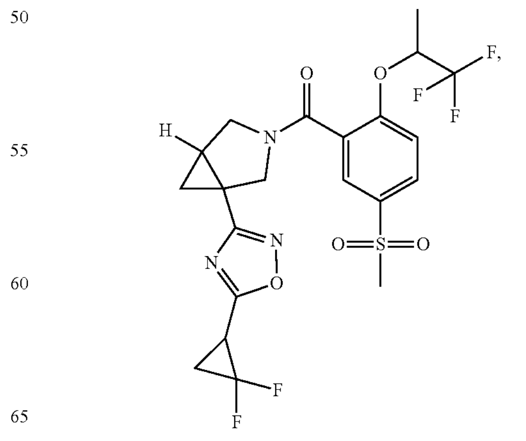

-continued
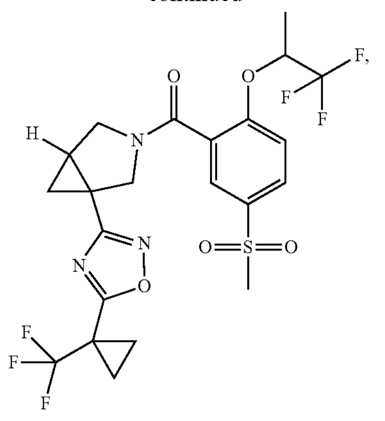
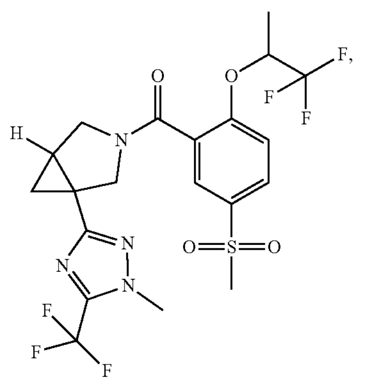
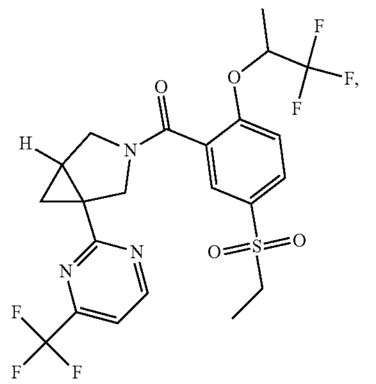
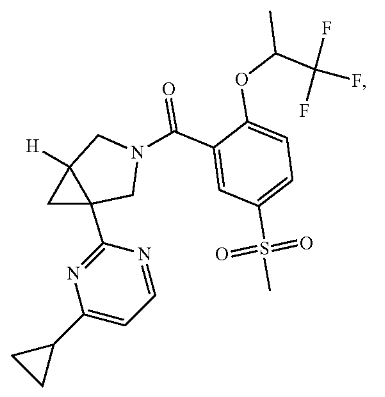
-continued
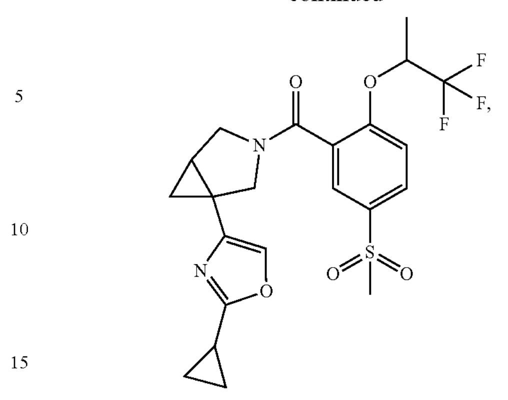
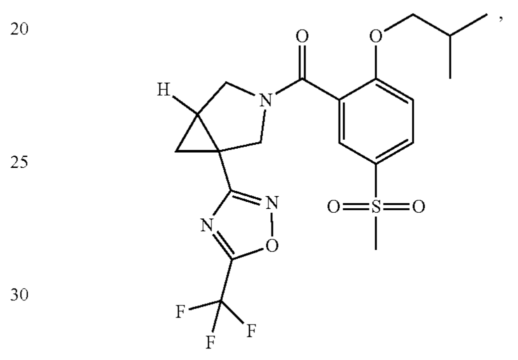
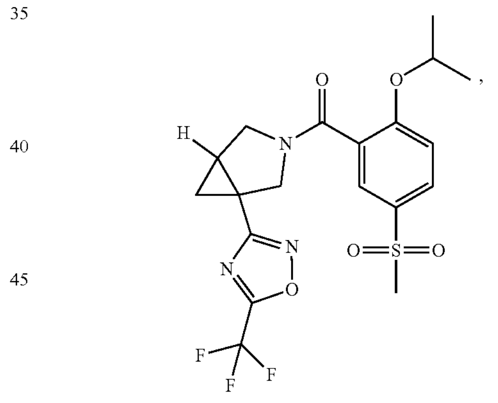
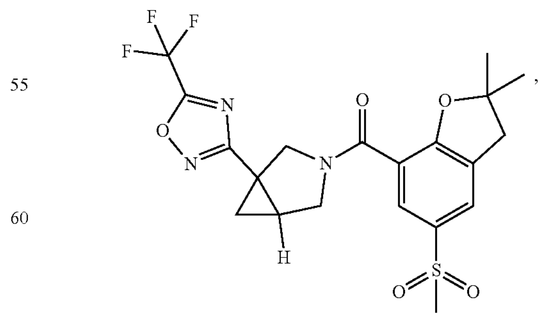

-continued
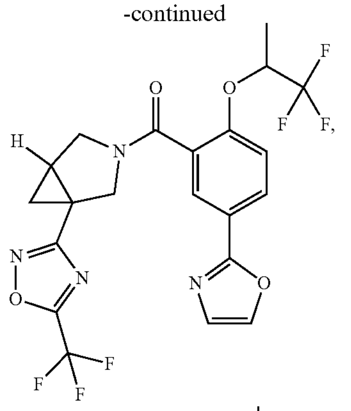
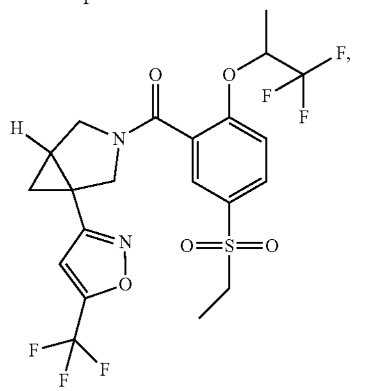
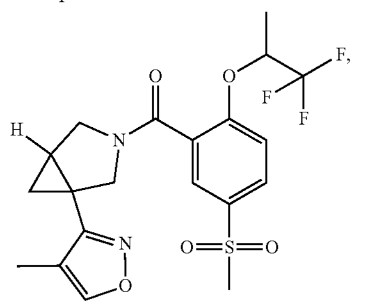
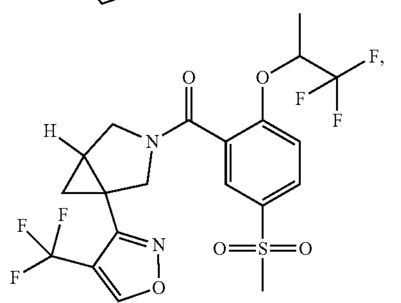
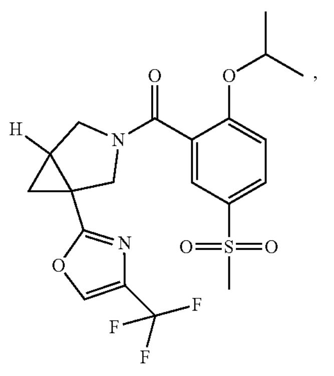
-continued
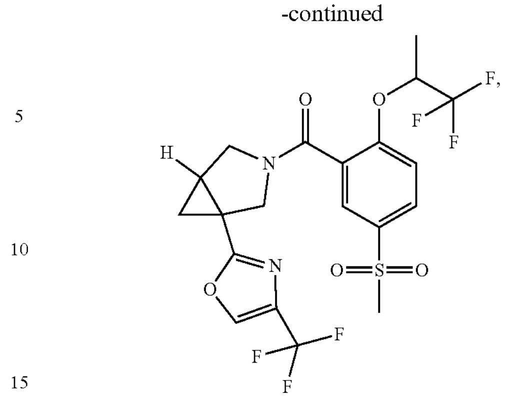
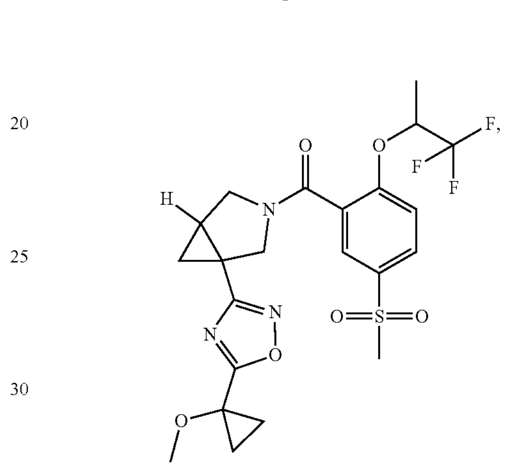
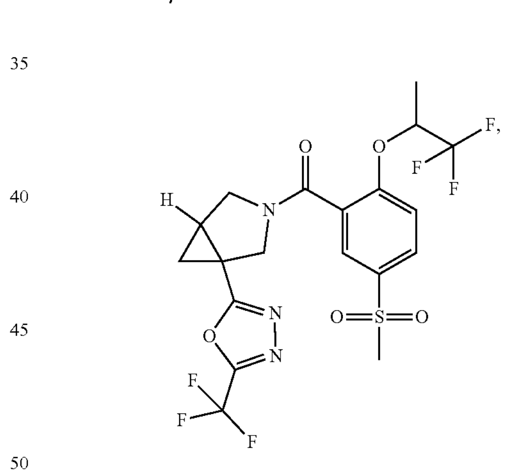
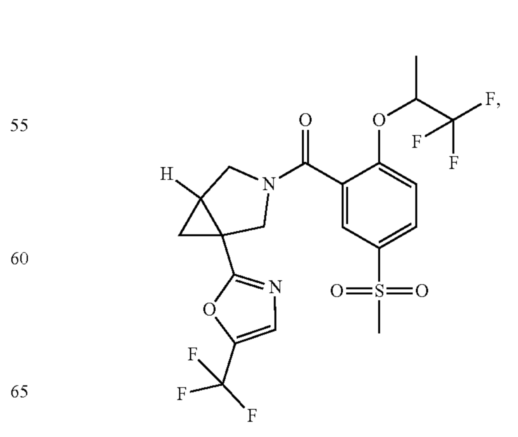

-continued
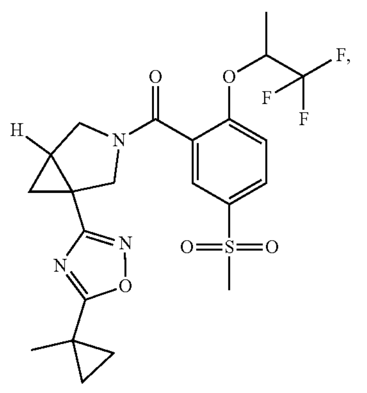
,
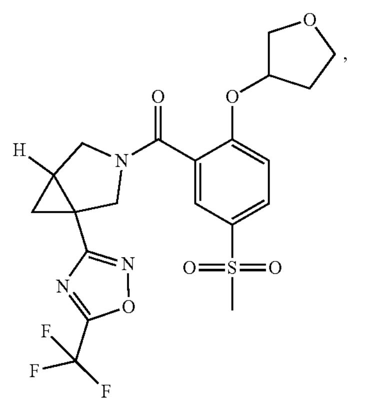
,
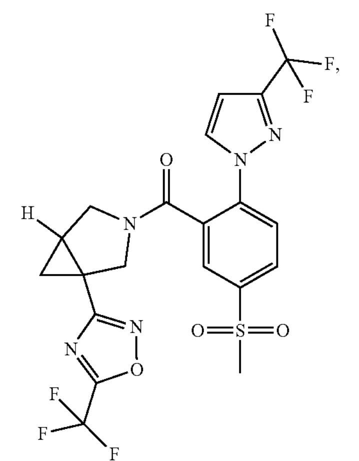
,
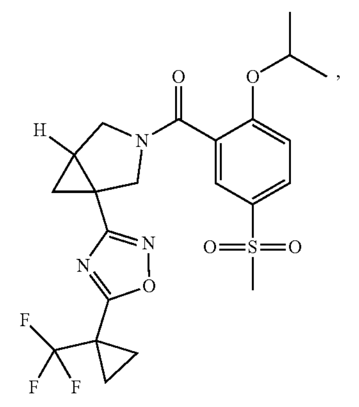
,
-continued
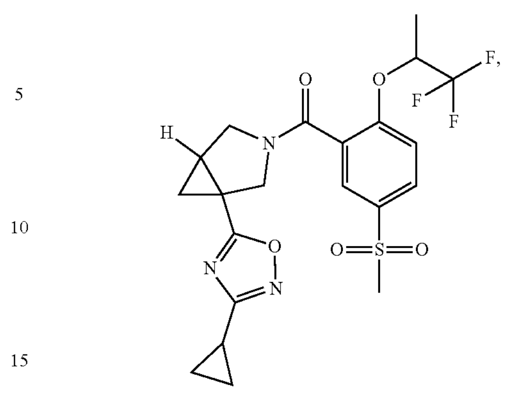
,
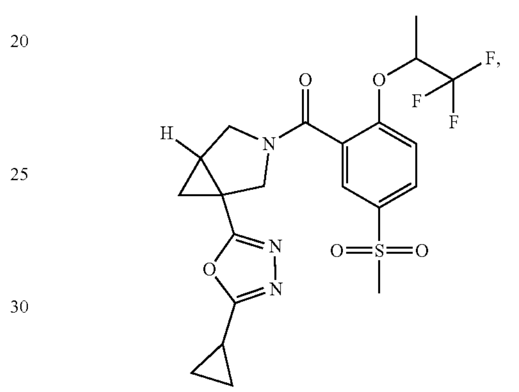
,
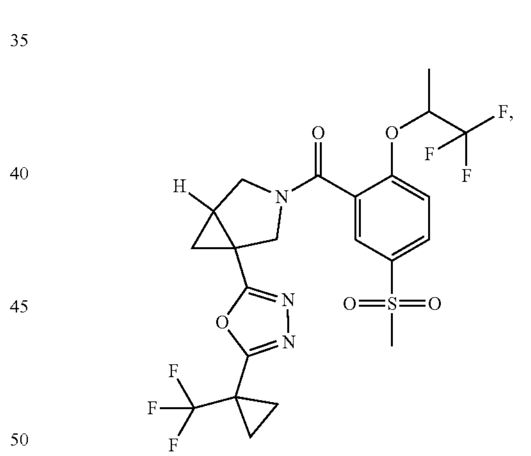
,
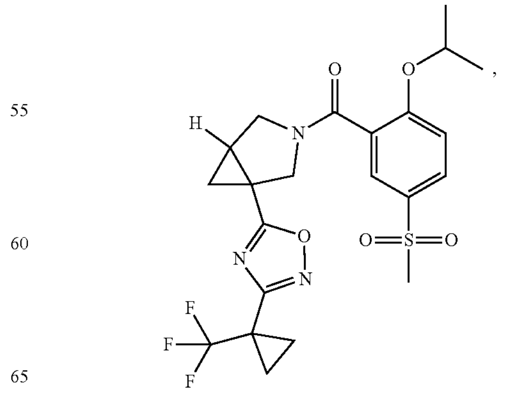
, -continued
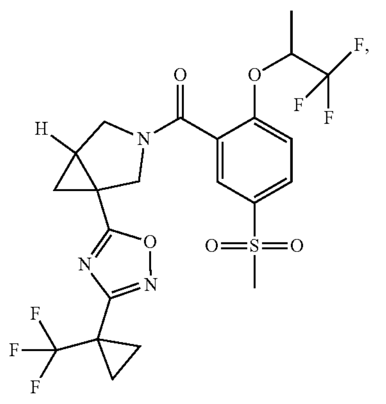
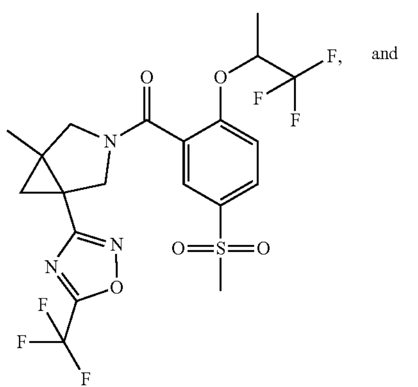
and
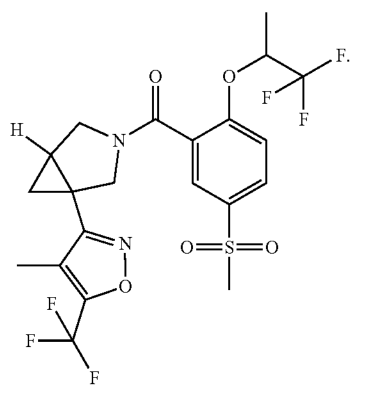
For example, the compound of Formula X could be a diastereomeric mixture or single diasteromer of any of the following, or a pharmaceutically acceptable salt thereof:
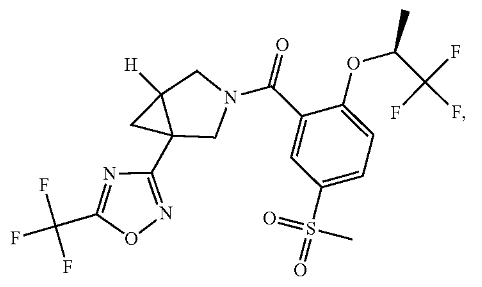
-continued
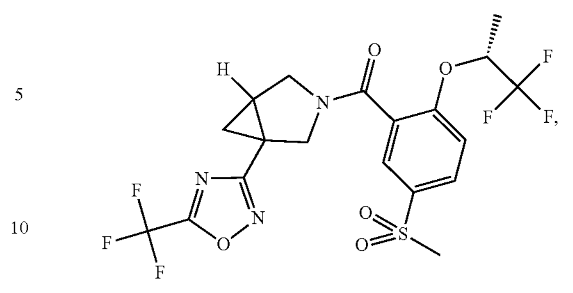
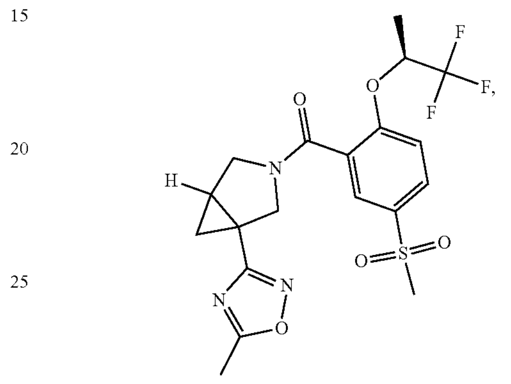
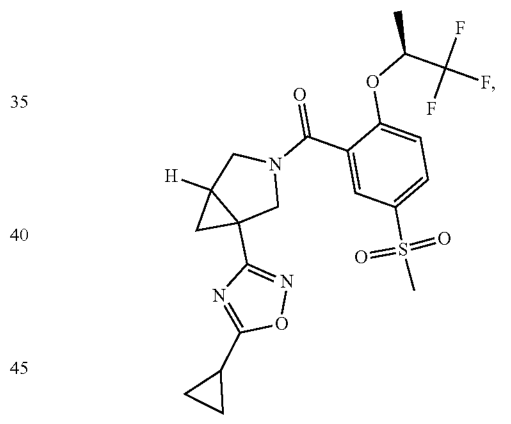
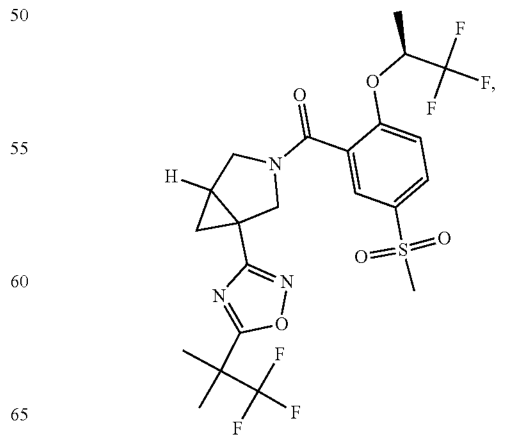

-continued
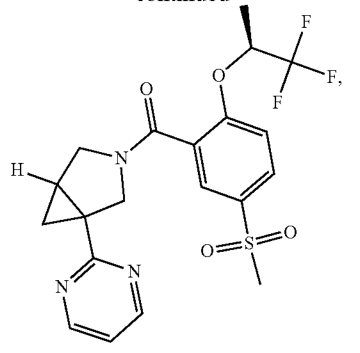
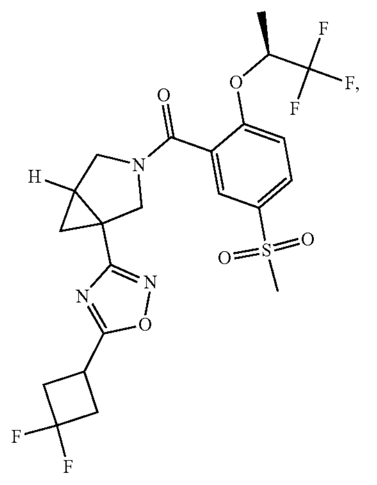
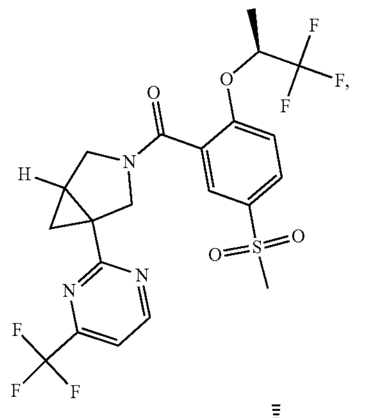
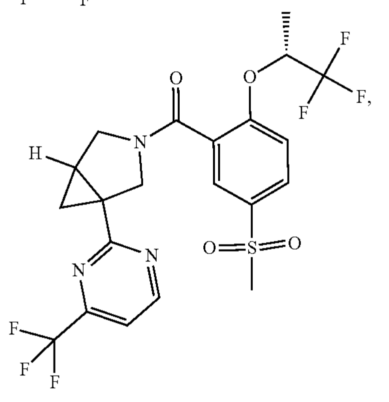
-continued
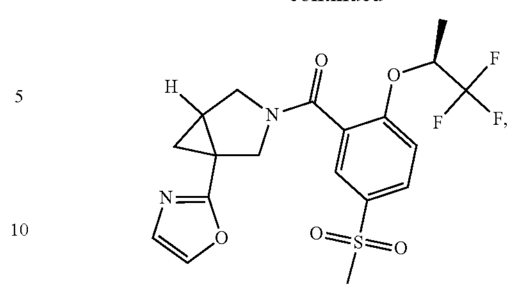
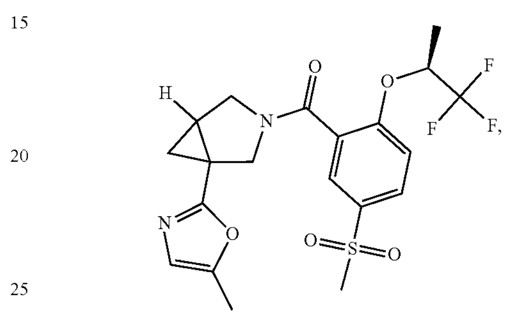
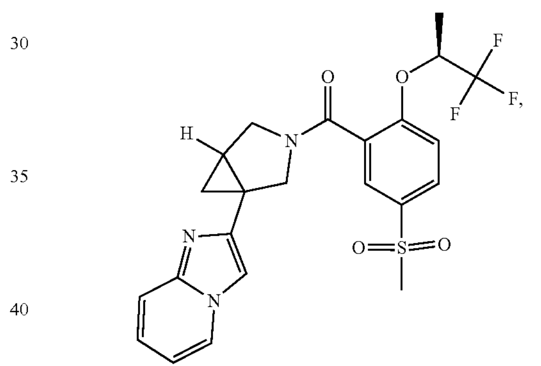
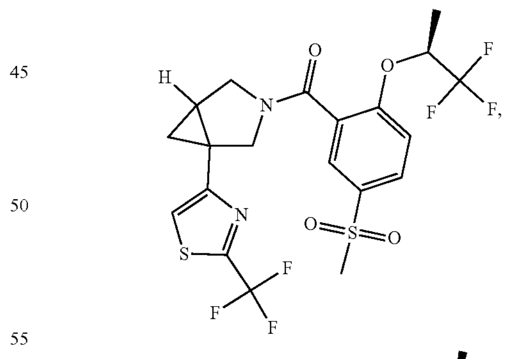
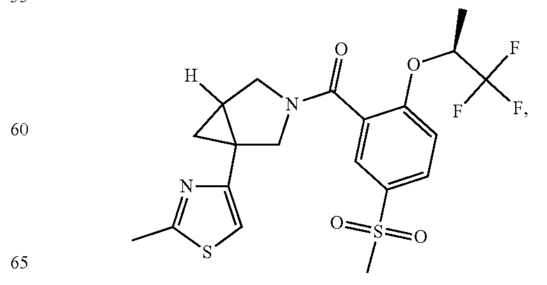

-continued
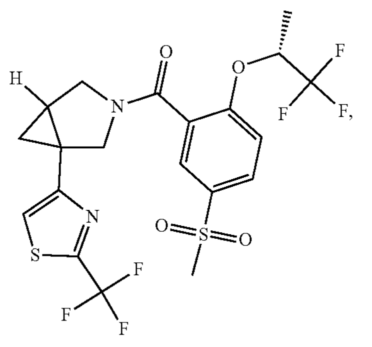
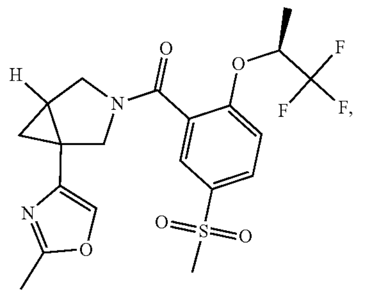
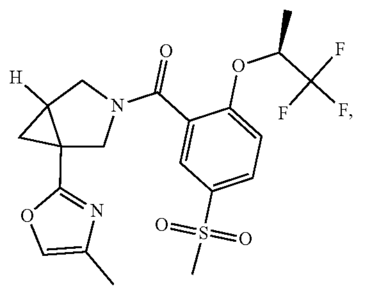
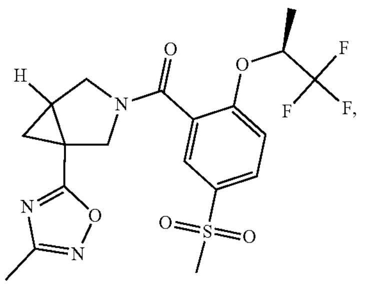
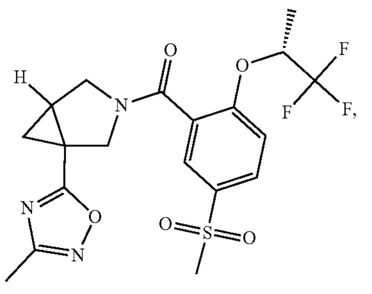
-continued
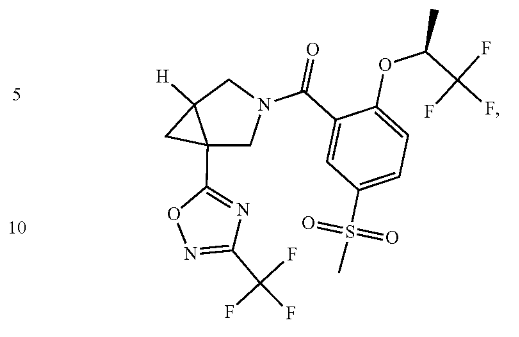
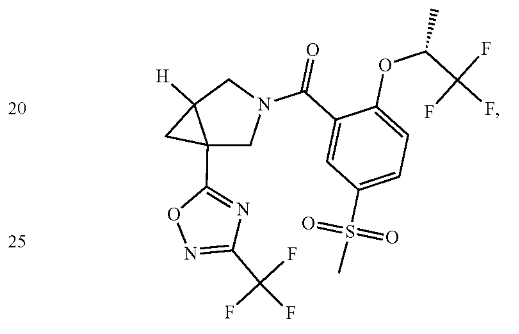
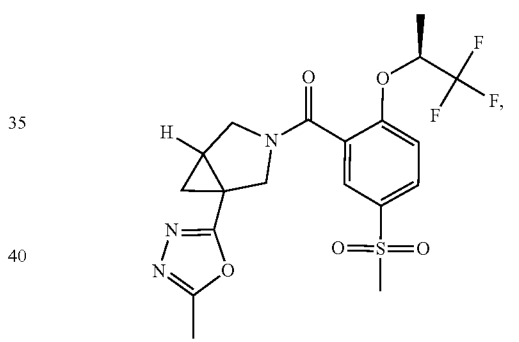
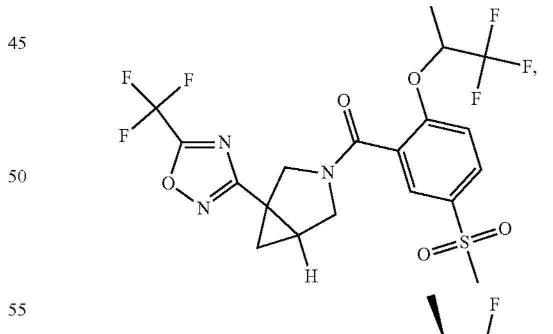
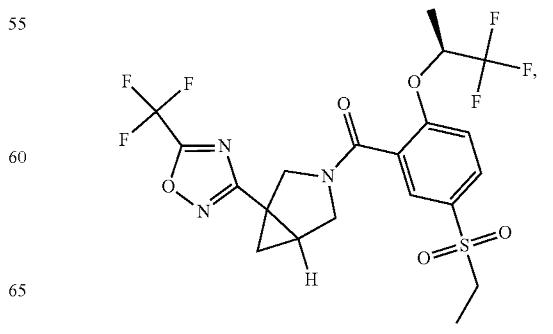

-continued
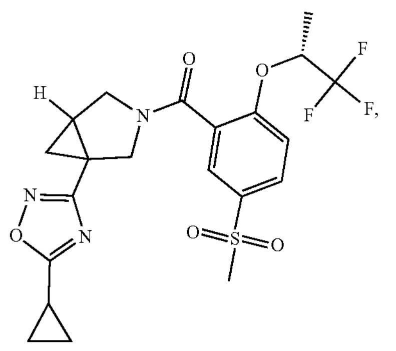
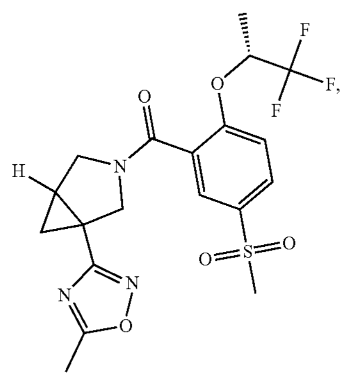
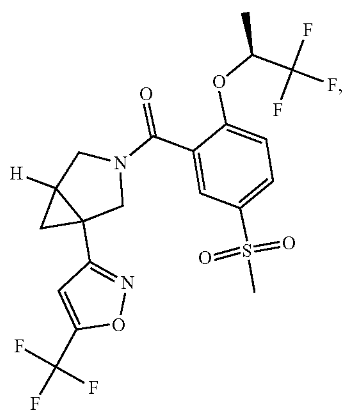
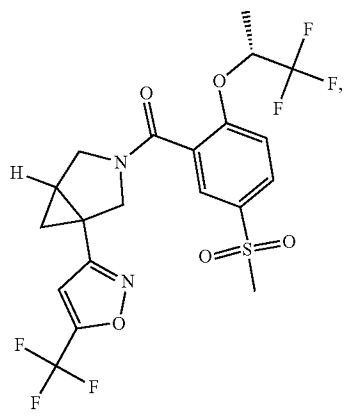
-continued
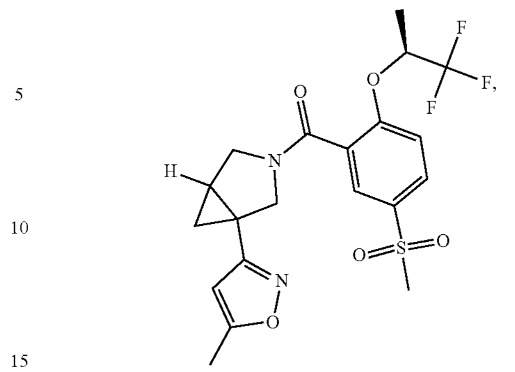
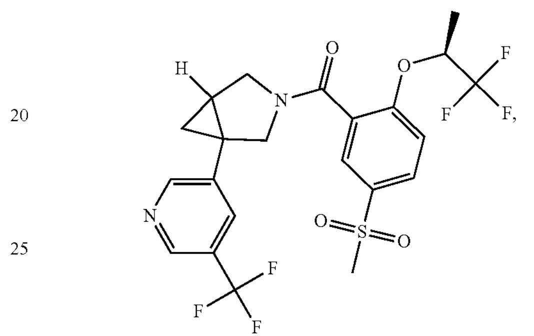
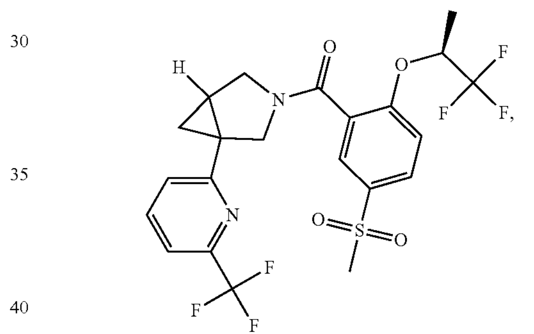
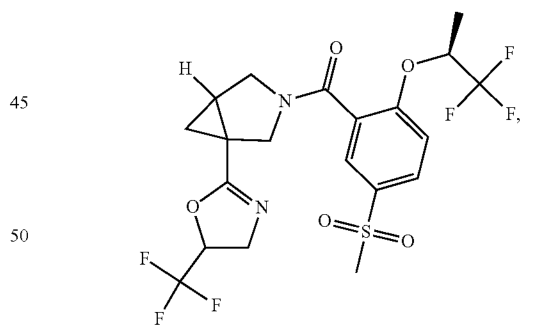
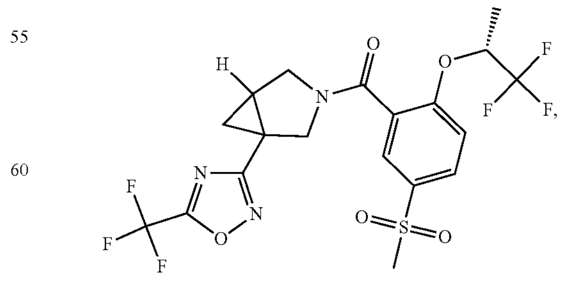

-continued
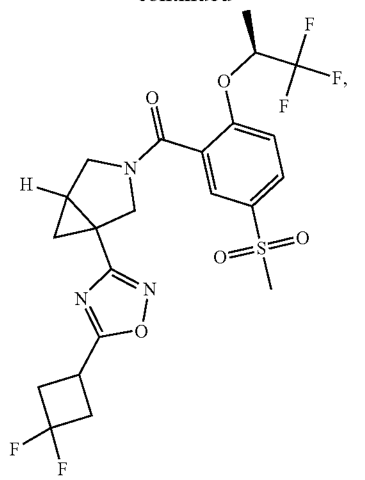
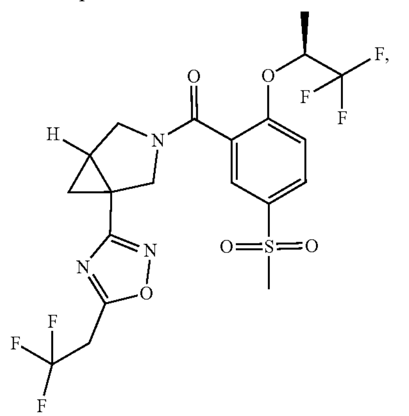
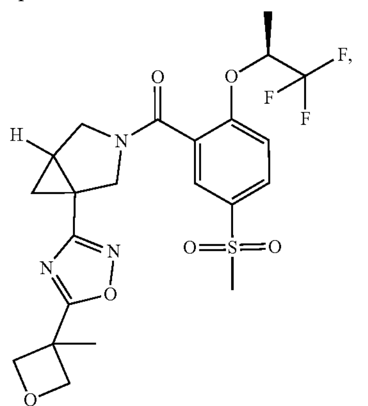
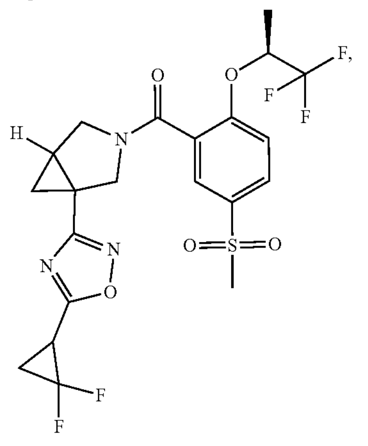
-continued
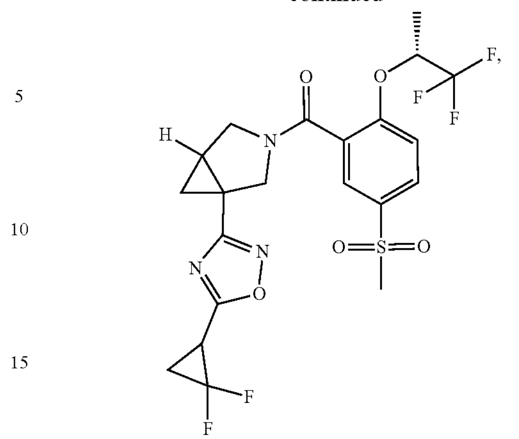
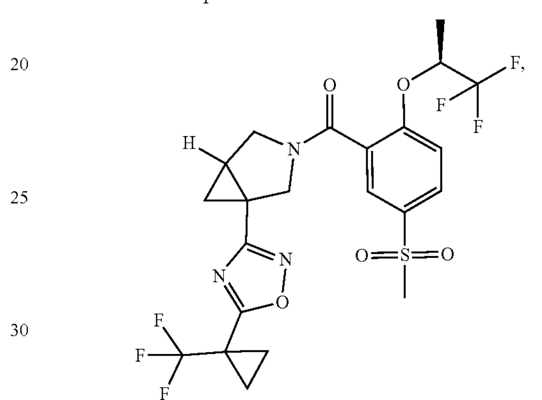
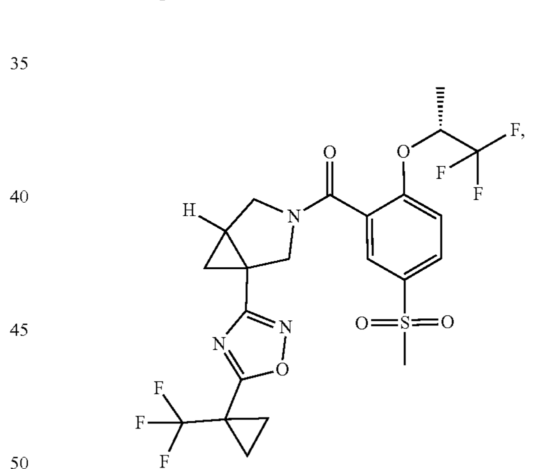
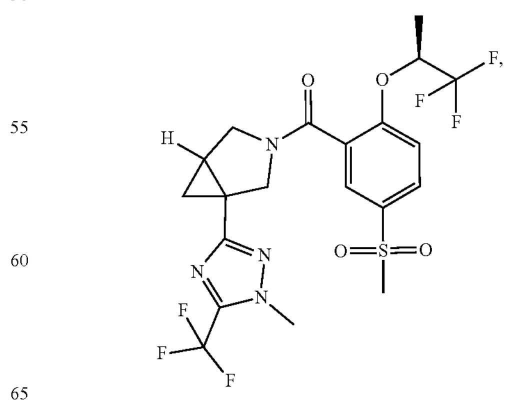

-continued
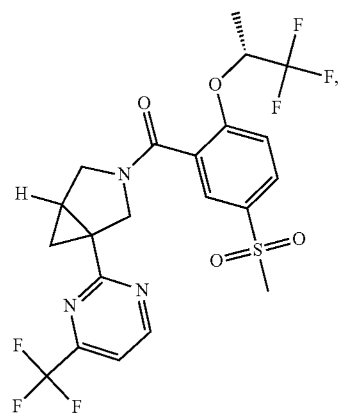
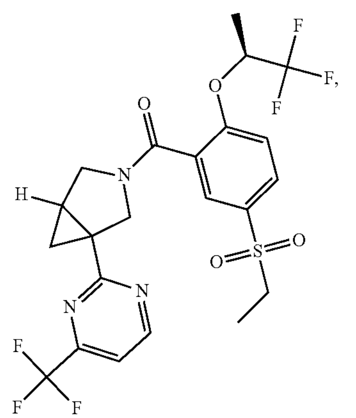
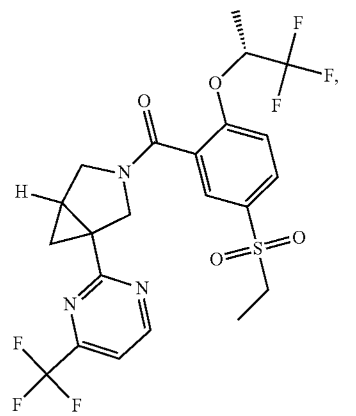
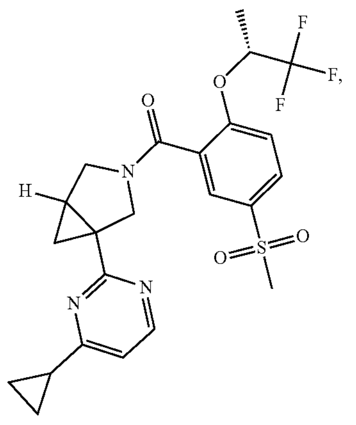
-continued
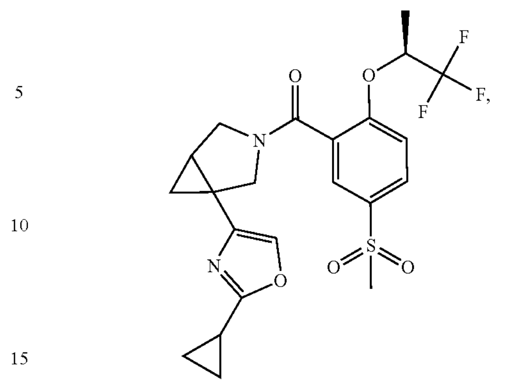
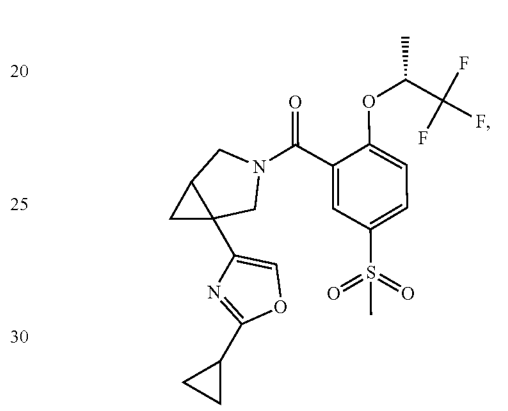
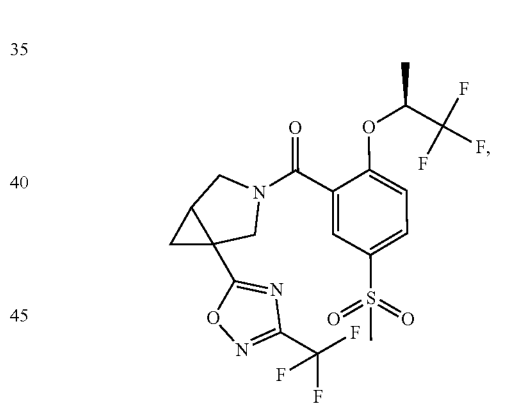
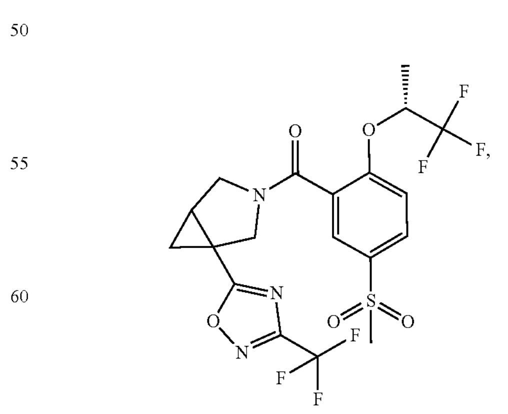

-continued
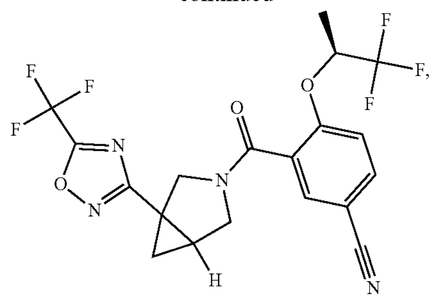
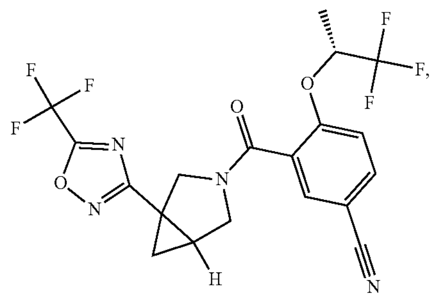
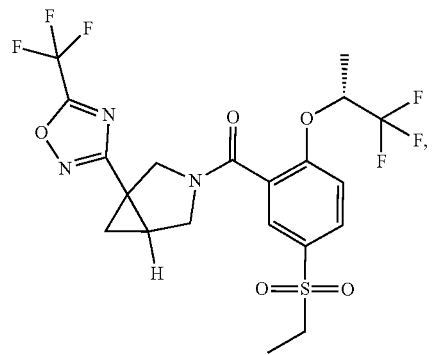
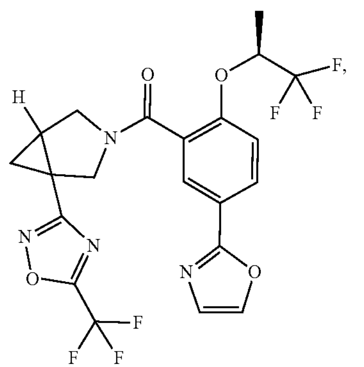
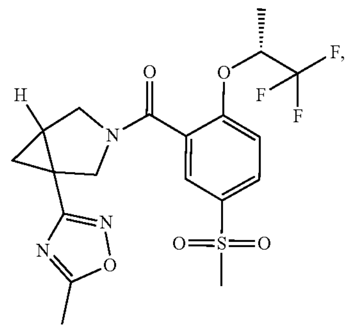
-continued
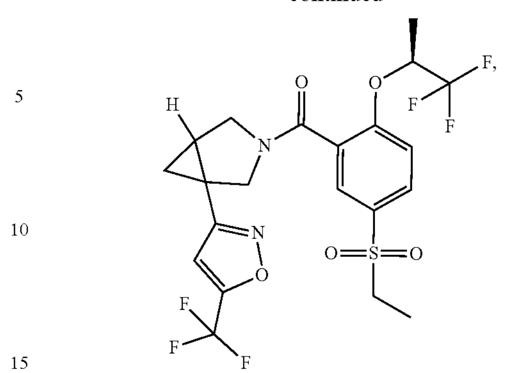
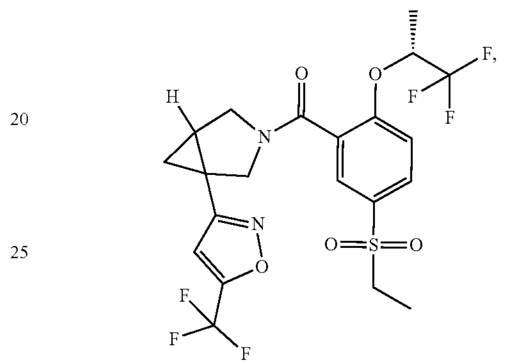
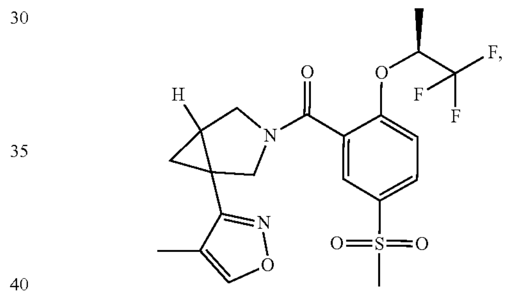
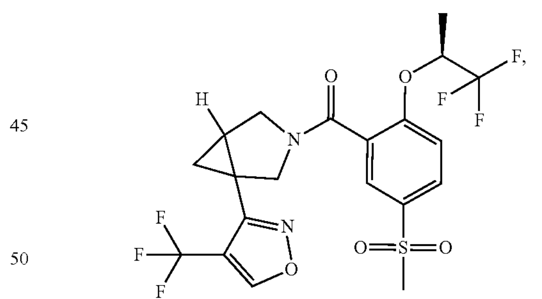
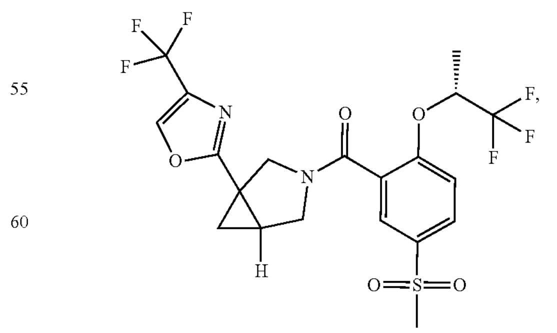

-continued
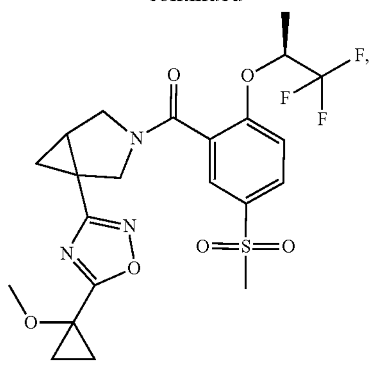
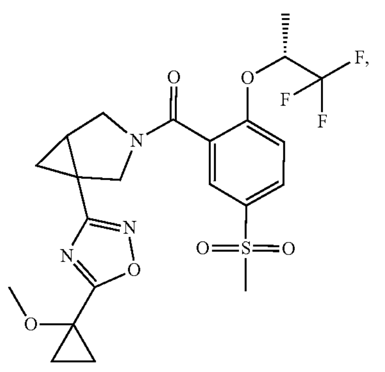
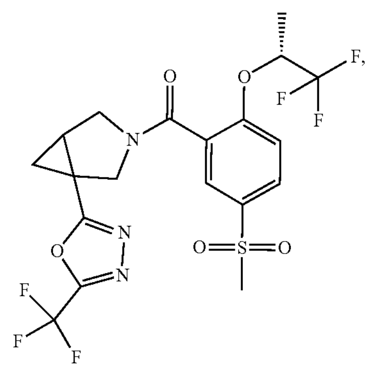
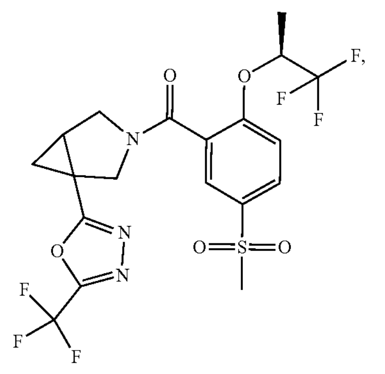
-continued
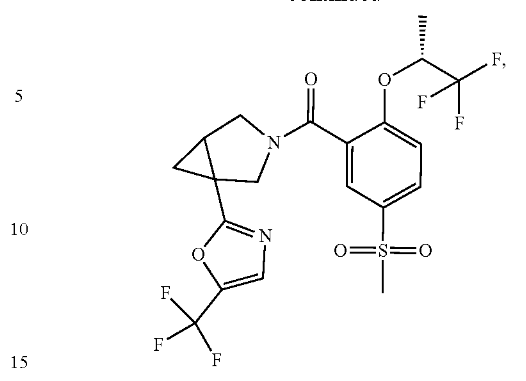
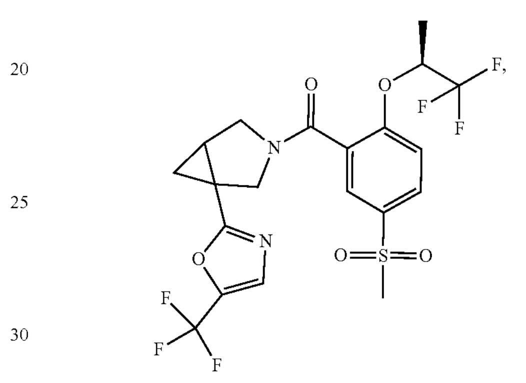
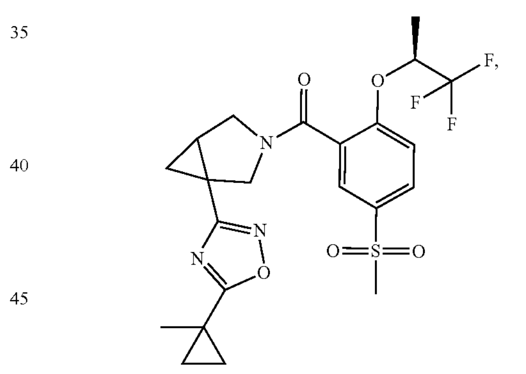
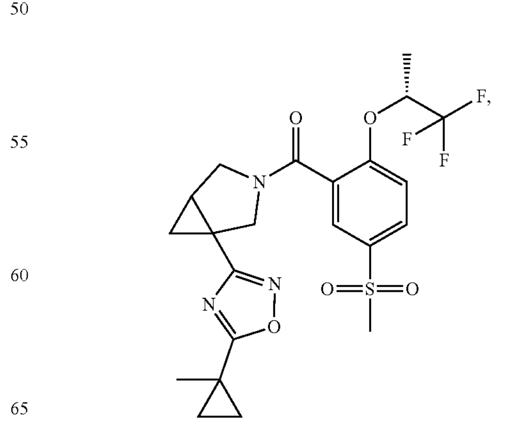

-continued
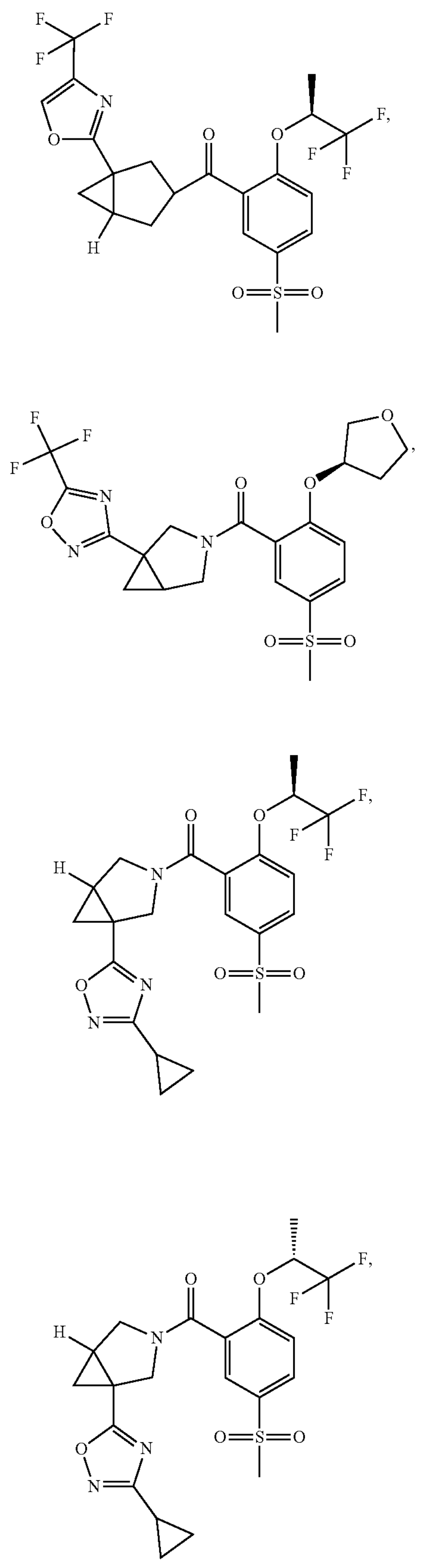
-continued
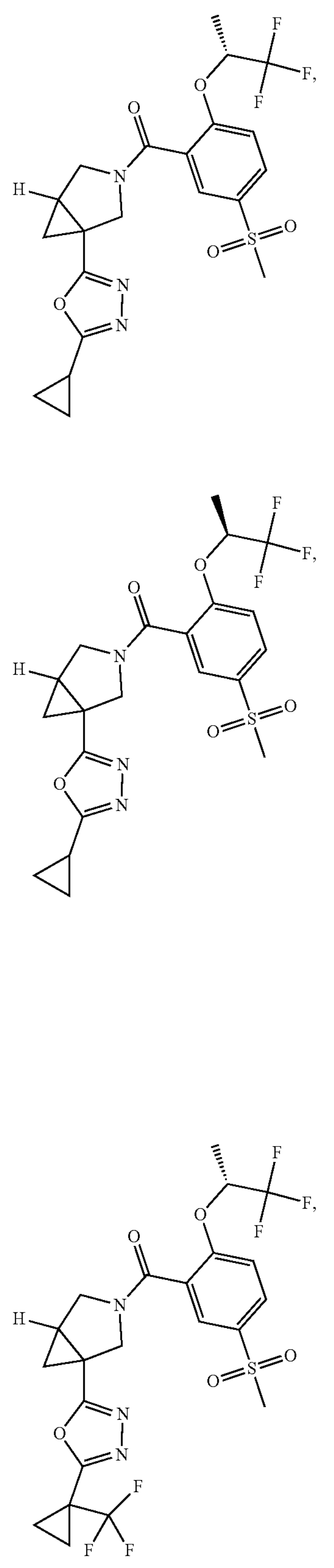

-continued

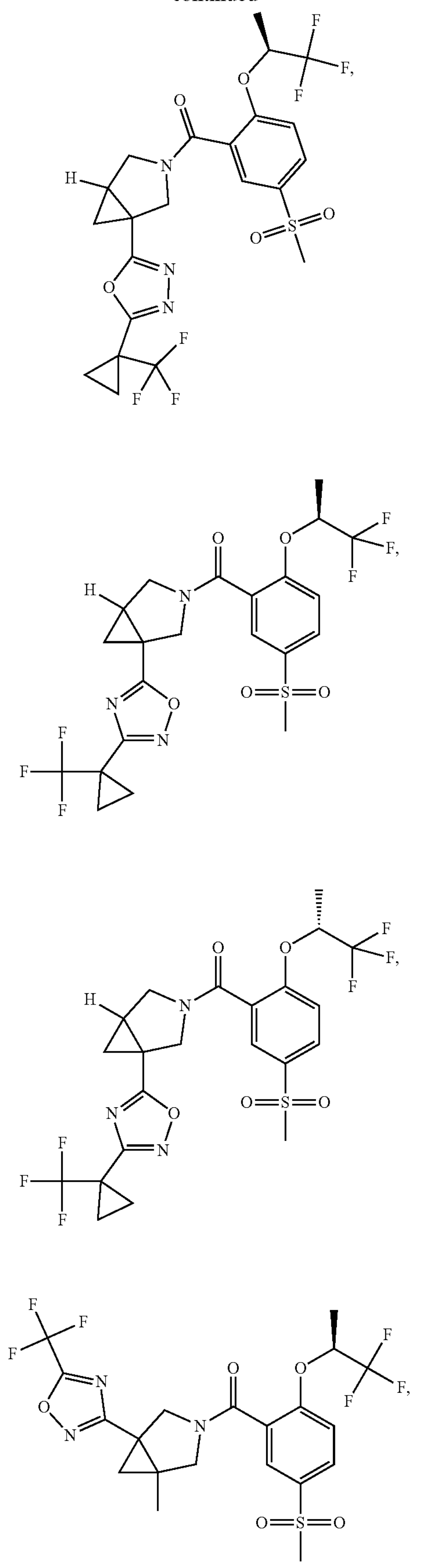

-continued

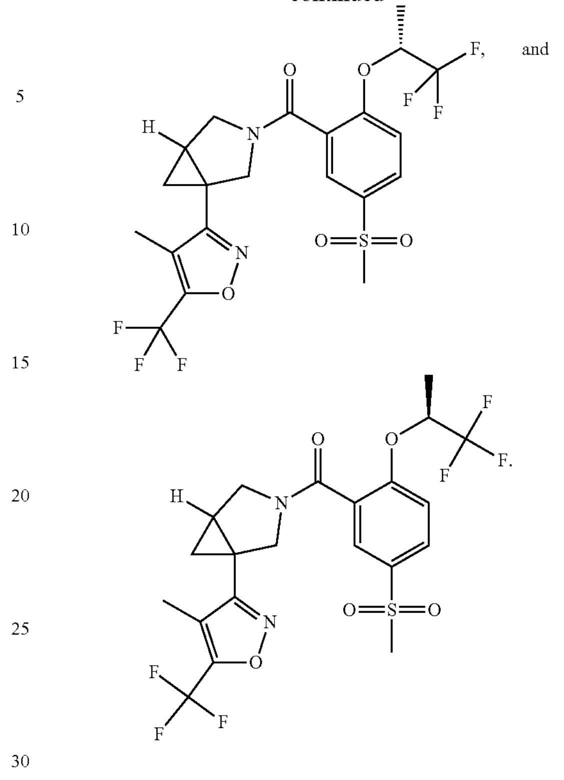

and

In certain of the methods and uses disclosed herein, the subject is a subject in need thereof.

In some embodiments of the uses and methods as disclosed herein, the glycine transporter inhibitor, such as a GlyT1 inhibitor (e.g., a GlyT1 inhibitor as disclosed herein), or a pharmaceutically acceptable salt thereof, or a prodrug of the glycine transporter inhibitor, such as a GlyT1 inhibitor (e.g., a GlyT1 inhibitor as disclosed herein), or its pharmaceutically acceptable salt is administered in a therapeutically effective amount.

In some embodiments, a compound, or a pharmaceutically acceptable salt, solvate or prodrug thereof, is chosen from a compound of as described herein. Any of the compounds provided for herein can be prepared as pharmaceutically acceptable salts, solvates or prodrugs and/or as part of a pharmaceutical composition as descripted in the cited patents or patent application publications herein.

Although the compounds described herein may be shown with specific stereochemistries around certain atoms, such as cis or trans, the compounds can also be made in the opposite orientation or in a racemic mixture. Such isomers or racemic mixtures are encompassed by the present disclosure. Additionally, although the compounds are shown collectively in a table, any compounds, or a pharmaceutically acceptable salt, solvate or prodrug thereof, can be chosen from the table and used in the embodiments provided for herein.

The compounds described herein can be made according to the methods described in the cited patents or patent application publications herein.

The compounds can be used to inhibit the GlyT1 transporter. Thus, in some embodiments, the compounds can be referred to as GlyT1 transporter inhibiting compounds or GlyT1 inhibitors.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginal, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt, solvate or prodrug thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as silastic membranes, or fibers.

The compounds described herein can be administered either alone or in combination (concurrently or serially) with other pharmaceuticals. For example, the compounds can be administered in combination with other drugs for the treatment of EPP, XLPP, or CEP and the like. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. In some embodiments, the compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts, solvates or prodrugs thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl) amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I-VIII is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of compounds include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof, phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts, solvates or prodrugs can be included in the compositions in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, such as, but not limited to, nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

In some embodiments, pharmaceutical packs or kits comprising one or more containers filled with one or more compounds described herein are provided. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

In some embodiments, the methods comprise administering to the subject one or more compounds described herein or a pharmaceutically acceptable salt, solvate or prodrug thereof, or a pharmaceutical composition of the same. In some embodiments, the subject is a subject in need of such treatment. As described herein, in some embodiments, the subject is a mammal, such as, but not limited to, a human.

In some embodiments, also provided are one or more compounds described above, or a pharmaceutically acceptable salt, solvate or prodrug thereof, or a pharmaceutical composition comprising one or more compounds described above, for use in the manufacture of a medicament for the treatment of methods of treating and/or preventing EPP, XLPP, or CEP, or related syndrome thereof, including, but not limited to the conditions described herein, in a subject, such as those described herein. In some embodiments, the subject is a subject in need thereof.

The present embodiments also provides the use of one or more compounds described above, or a pharmaceutically acceptable salt, solvate or prodrug thereof, or a pharmaceutical composition comprising one or more compounds described above, in the inhibition of a GlyT1 transporter, such as the presence on the surface of the cell. In some embodiments, the compounds, pharmaceutically acceptable salt thereof, or a pharmaceutical composition of the same inhibit the internalization, trafficking, and/or degradation of the GlyT1 transporter.

As used herein, "inhibition" can refer to either inhibition of a specific activity. The activity of a GlyT1 transporter can be measured by any method known in the art including but not limited to the methods described herein.

The compounds described herein are inhibitors of the GlyT1 transporter. The ability of the compounds to inhibit GlyT1 transporter activity may be measured using any assay known in the art.

Generally, assays for testing compounds that inhibit GlyT1 transporter activity include the determination of any parameter that is indirectly or directly under the influence of a GlyT1 transporter, e.g., a functional, physical, or chemical effect.

Samples or assays comprising GlyT1 transporters that are treated with a potential inhibitor, are compared to control samples without the inhibitor to examine the extent of inhibition. Control samples (untreated with inhibitors) are assigned a relative GlyT1 transporter activity value of 100%. Inhibition of a GlyT1 transporter is achieved when the GlyT1 transporter activity value relative to the control is about 80%, 50%, or 25%.

Ligand binding to a GlyT1 transporter can be tested in a number of formats. Binding can be performed in solution, in a bilayer membrane, attached to a solid phase, in a lipid monolayer, or in vesicles. For example, in an assay, the binding of the natural ligand to its transporter is measured in the presence of a candidate modulator, such as the compound described herein. Alternatively, the binding of the candidate modulator may be measured in the presence of the natural ligand. Often, competitive assays that measure the ability of a compound to compete with binding of the natural ligand to the transporter are used. Binding can be tested by measuring, e.g., changes in spectroscopic characteristics (e.g., fluorescence, absorbance, refractive index), hydrodynamic (e.g., shape) changes, or changes in chromatographic or solubility properties.

After the transporter is expressed in cells, the cells can be grown in appropriate media in the appropriate cell plate. The cells can be plated, for example at 5000-10000 cells per well in a 384 well plate. In some embodiments, the cells are plated at about 1000, 2000, 3000, 4000, 5000, 6000, 7000, 8000, 9000, or 10000 cells/per well. The plates can have any number of wells and the number of cells can be modified accordingly.

Any medicament having utility in an application described herein can be used in co-therapy, co-administration or co-formulation with a composition as described above. Therefore, the compounds described herein can be administered either before, concurrently with, or after such therapeutics are administered to a subject.

The additional medicament can be administered in co-therapy (including co-formulation) with the one or more of the compounds described herein.

In some embodiments, the response of the disease or disorder to the treatment is monitored and the treatment regimen is adjusted if necessary in light of such monitoring.

Frequency of administration is typically such that the dosing interval, for example, the period of time between one dose and the next, during waking hours is from about 1 to about 24, about 2 to about 12 hours, from about 3 to about 8 hours, or from about 4 to about 6 hours. In some embodiments, the dose is administered 1, 2, 3, or 4 times a day. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which inhibits the transporter's activity by 90%). Ideally the concentration remains above the $EC_{50}$ for at least 100% of the dosing interval. Where this is not achievable it is desired that the concentration should remain above the $EC_{50}$ for at least about 60% of the dosing interval or should remain above the $EC_{50}$ for at least about 40% of the dosing interval.

Methods of Use

The present application provides methods of preventing or treating disorders associated with accumulation of PPIX in a subject, the method comprising administering to the subject one or more glycine transporter inhibitor or a pharmaceutically acceptable salt thereof, or a prodrug of the one or more glycine transporter inhibitor or its pharmaceutically acceptable salt. In certain embodiments, the glycine transporter inhibitor is a GlyT1 inhibitor, such as a GlyT1 inhibitor as disclosed herein. For example, the present application provides a method of preventing or treating disorders associated with accumulation of PPIX in a subject, comprising administering to the subject bitopertin

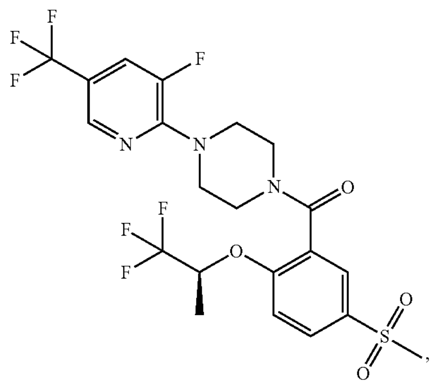 [SMILES: C[C@H](Oc1ccc(S(C)(=O)=O)cc1C(=O)N1CCN(c2ncc(C(F)(F)F)cc2F)CC1)C(F)(F)F]

or a pharmaceutically acceptable salt thereof, or a prodrug of bitopertin or its pharmaceutically acceptable salt.

In part, the present disclosure relates to methods of treating erythropoietic protoporphyria (EPP), X-linked protoporphyria (XLPP), or congenital erythropoietic porphyria (CEP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In certain embodiments, the present disclosure provides methods of preventing, treating, or reducing the progression rate and/or severity of one or more complications of EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its pharmaceutically acceptable salt. These methods are particularly aimed at therapeutic and prophylactic treatments of animals, and more particularly, humans. The terms "subject," an "individual," or a "patient" are interchangeable throughout the specification and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In particular embodiments, the patient, subject or individual is a human.

The present application provides methods of preventing or treating erythropoietic protoporphyria (EPP), X-linked protoporphyria (XLPP), or congenital erythropoietic porphyria (CEP), or related syndrome (e.g., EPP-related syndrome, XLPP-related syndrome, or CEP-related syndrome) thereof in a subject, the method comprising administering to the subject one or more glycine transporter inhibitor, or a pharmaceutically acceptable salt thereof, or a prodrug of the one or more glycine transporter inhibitor or its pharmaceutically acceptable salt. The present application further provides methods of preventing or treating EPP, XLPP, or CEP in a subject, the method comprising administering to the subject one or more glycine transporter inhibitor, or a pharmaceutically acceptable salt thereof, or a prodrug of the one or more glycine transporter inhibitor or its pharmaceutically acceptable salt. For example, the present application provides methods of treating EPP, XLPP, or CEP in a subject, the method comprising administering to the subject one or more glycine transporter inhibitor, or a pharmaceutically acceptable salt thereof, or a prodrug of the one or more glycine transporter inhibitor or its pharmaceutically acceptable salt. In some embodiments, the one or more glycine transporter inhibitor is one or more GlyT1 and/or GlyT2 inhibitors. In some embodiments, the one or more glycine transporter inhibitor is one or more GlyT1 inhibitor, such as one or more GlyT1 inhibitor as disclosed herein. For example, the present application provides a method of preventing or treating EPP, XLPP, or CEP in a subject, comprising administering to the subject bitopertin, or a pharmaceutically acceptable salt thereof, or a prodrug of bitopertin or its pharmaceutically acceptable salt.

The present application further provides methods of preventing or treating EPP, XLPP, or CEP, or related syndrome thereof (e.g., EPP-related syndrome, XLPP-related syndrome, or CEP-related syndrome) in a subject, the method comprising administering to the subject a pharmaceutical composition comprising one or more glycine transporter inhibitor, or a pharmaceutically acceptable salt thereof, or a prodrug of the one or more glycine transporter inhibitor or its pharmaceutically acceptable salt. The present application further provides methods of preventing or treating EPP, XLPP, or CEP in a subject, the method comprising administering to the subject a pharmaceutical composition comprising one or more glycine transporter inhibitor, or a pharmaceutically acceptable salt thereof, or a prodrug of the one or more glycine transporter inhibitor or its pharmaceutically acceptable salt. For example, the present application provides methods of treating EPP, XLPP, or CEP in a subject, the method comprising administering to the subject a pharmaceutical composition comprising one or more glycine transporter inhibitor, or a pharmaceutically acceptable salt thereof, or a prodrug of the one or more glycine transporter inhibitor or its pharmaceutically acceptable salt. In some embodiments, the one or more glycine transporter inhibitor is one or more GlyT1 and/or GlyT2 inhibitors. In some embodiments, the one or more glycine transporter inhibitor is one or more GlyT1 inhibitor, such as one or more GlyT1 inhibitor as disclosed herein. In certain embodiments of the foregoing, the pharmaceutical composition further comprises a pharmaceutically acceptable carrier. For example, the present application provides methods of preventing or treating EPP, XLPP, or CEP in a subject, the method comprising administering to the subject a pharmaceutical composition comprising bitopertin, or a pharmaceutically acceptable salt thereof, or a prodrug of bitopertin or its pharmaceutically acceptable salt, wherein the pharmaceutical composition further comprises a pharmaceutically acceptable carrier.

Erythropoietic protoporphyria (EPP) and X-linked protoporphyria (XLPP) are erythropoietic cutaneous porphyrias characterized by acute non-blistering photosensitivity, intolerance to sunlight, and significantly reduced quality of life. EPP is caused by a partial deficiency in ferrochelatase (FECH), which catalyzes the final step in the heme biosynthesis pathway. FECH deficiency increases levels of metal-free erythrocyte PPIX (also referred to herein as "free-protoporphyrin IX" and "PPIX"). XLPP is typically caused by C-terminal deletions in the ALAS2 gene which result in a gain-of-function mutation. These gain-of-function mutations increase the enzymatic activity of ALAS2 and cause an accumulation of both metal-free and zinc-bound PPIX. Both EPP and XLPP result in an accumulation of PPIX in erythrocytes and other tissues or biological fluids (e.g., skin, liver, bile, or stool). PPIX, which is lipophilic and eliminated via bile, is hepatotoxic at high concentrations.

Patients with EPP or XLPP usually develop photosensitivity during early childhood. Patients frequently present with symptoms of burning, itching, pain erythema, and edema on sun-exposed areas. Cutaneous symptoms are sometimes associated with abnormal liver enzyme activities, hepatobiliary injury, such as jaundice and liver cirrhosis, iron deficiency, and corresponding microcytic anemia.

The diagnosis of EPP and XLPP can be determined by measuring the levels of total erythrocyte, free-protoporphyrin IX, and zinc-protoporphyrin IX in hemolyzed anticoagulated whole blood. A diagnosis of EPP and/or XLPP can be made based on increased levels of free-protoporphyrin IX in blood. Patients with XLPP have a significantly higher proportion of zinc-protoporphyrin IX to free-protoporphyrin IX (e.g., >25%) as compared to those with EPP (e.g., ≤15%).

The diagnosis of EPP can also be determined by measuring the level of ferrocheletase activity in a subject. Ferrocheletase is a mitochondrial enzyme that catalyzes the insertion of ferrous iron into PPIX to form heme. Ferrocheletase also catalyzes the insertion of zinc, to form zinc protoporphyrin IX (ZPPIX) from any PPIX that remains after completion of heme synthesis. In EPP, free PPIX accumulates in bone marrow reticulocytes, since formation of both heme and ZPPIX is impaired. In some embodiments, the disclosure relates to methods of a treating a subject whose ferrochelatase activity level is reduced to between 10 to 35% of the ferrocheletase activity level observed in normal subjects. In some embodiments, the disclosure relates to methods of a treating a subject whose ferrochelatase activity level is reduced to less than 50% of the ferrocheletase activity level observed in normal subjects.

XLPP has a similar phenotype to EPP, and can be differentiated based on genetic analysis of ALAS2 or by determining the enzymatic activity level of ALAS2. In some embodiments, the disclosure relates to methods of a treating a subject having a gain-of-function mutation in ALAS2. In some embodiments, the subject's ALAS2 enzyme activity is increased. Since ferrocheletase is not deficient in XLPP, some of the excess PPIX measured in erythrocytes is ZPPIX and a lower percentage (e.g., 50-85%) is metal-free. In some embodiments, the subject has increased zinc-protoporphyrin IX levels in erythrocytes. In some embodiments, the method decreases zinc-protoporphyrin IX levels in the subject's erythrocytes. In some embodiments, method decreases zinc-protoporphyrin IX levels in the subject's erythrocytes by at least 10% (e.g., 10%, 15%, 20%, 25%, 30%, 35%, 40%, 45%, 50%, 55%, 60%, 65%, 70%, 75%, 80%, 85%, 90%, 95%, or at least 100%).

In certain aspects, the disclosure relates to methods of treating erythropoietic protoporphyria (EPP) and/or X-linked protoporphyria (XLPP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject has increased PPIX levels. In some embodiments, the method relates to subjects having PPIX levels that are at least 10%, 20%, 30%, 40%, or 50% more than PPIX levels in a healthy subject prior to administration of the glycine transporter inhibitor (e.g., a GlyT1 inhibitor). In some embodiments, the method relates to subjects having PPIX levels that are at least 10% more than PPIX levels in a healthy subject prior to administration of the glycine transporter inhibitor (e.g., a GlyT1 inhibitor). In some embodiments, the method relates to subjects having PPIX levels that are at least 20% more than PPIX levels in a healthy subject prior to administration of the glycine transporter inhibitor (e.g., a GlyT1 inhibitor). In some embodiments, the method relates to subjects having PPIX levels that are at least 30% more than PPIX levels in a healthy subject prior to administration of the glycine transporter inhibitor (e.g., a GlyT1 inhibitor). In some embodiments, the method relates to subjects having PPIX levels that are at least 40% more than PPIX levels in a healthy subject prior to administration of the glycine transporter inhibitor (e.g., a GlyT1 inhibitor). In some embodiments, the method relates to subjects having PPIX levels that are at least 50% more than PPIX levels in a healthy subject prior to administration of the glycine transporter inhibitor (e.g., a GlyT1 inhibitor). In some embodiments, the subject has increased protoporphyrin IX levels in the stool. In some embodiments, the subject has increased protoporphyrin IX levels in the skin. In some embodiments, the subject has increased free-protoporphyrin IX levels in erythrocytes. In some embodiments, the subject has greater than 31 μmol L-1 protoporphyrin IX levels in the erythrocytes. In some embodiments, the subject has between 31 μmol L-1 and 53 μmol L-1 protoporphyrin IX levels in the erythrocytes. In some embodiments, the subject has greater than 53 μmol L-1 protoporphyrin IX levels in the erythrocytes.

The present application further provides methods of inhibiting PPIX synthesis in vivo, comprising administering to a subject a glycine transporter inhibitor, or a pharmaceutically acceptable salt thereof, or a prodrug of the one or more glycine transporter inhibitor or its pharmaceutically acceptable salt. In certain aspects, the disclosure relates to methods of inhibiting PPIX synthesis in vivo, comprising administering to a subject a glycine transporter inhibitor (e.g., a GlyT1 inhibitor), or a pharmaceutically acceptable salt thereof, or a prodrug of the glycine transporter inhibitor (e.g., a GlyT1 inhibitor) or its pharmaceutically acceptable salt. In some embodiments, the disclosure relates to methods of inhibiting PPIX synthesis in vivo by at least 10% (e.g., 10%, 20%, 30%, 40%, 50%, 60%, 70%, 80%, 90%, or at least 100%). In some embodiments, the disclosure relates to methods of inhibiting PPIX synthesis in vivo by at least 20%. In some embodiments, the disclosure relates to methods of inhibiting PPIX synthesis in vivo by at least 30%. In some embodiments, the disclosure relates to methods of inhibiting PPIX synthesis in vivo by at least 40%. In some embodiments, the disclosure relates to methods of inhibiting PPIX synthesis in vivo by at least 50%. In some embodiments, the disclosure relates to methods of inhibiting PPIX synthesis in vivo by at least 60%. In some embodiments, the disclosure relates to methods of inhibiting PPIX synthesis in vivo by at least 70%. In some embodiments, the disclosure relates to methods of inhibiting PPIX synthesis in vivo by at least 80%. In some embodiments, the disclosure relates to methods of inhibiting PPIX synthesis in vivo by at least 90%. In some embodiments, the disclosure relates to methods of inhibiting PPIX synthesis in vivo by at least 100%. The present application further provides methods of decreasing the rate of PPIX synthesis in vivo, comprising administering to a subject a glycine transporter inhibitor, or a pharmaceutically acceptable salt thereof, or a prodrug of the one or more glycine transporter inhibitor or its pharmaceutically acceptable salt. In certain embodiments of the methods and uses as disclosed herein inhibit PPIX accumulation directly or indirectly. In certain such embodiments, PPIX accumulation is inhibited in a dose dependent manner. In certain embodiments of the foregoing methods, the glycine transporter inhibitor is a GlyT1inhibitor, such as a GlyT1 inhibitor as disclosed herein. For example, the present application provides a method of inhibiting PPIX synthesis in vivo, decreasing the rate of PPIX synthesis in vitro, and/or inhibiting PPIX accumulation in vivo, comprising administering to a subject bitopertin, or a pharmaceutically acceptable salt thereof, or a prodrug of bitopertin or its pharmaceutically acceptable salt.

In some embodiments, the method relates to methods of decreasing free-protoporphyrin IX levels in the subject. In some embodiments, the method relates to methods of decreasing free-protoporphyrin IX levels in the subject's erythrocytes. In some embodiments, the method decreases protoporphyrin IX levels in the erythrocytes of the subject to levels less than 53 μmol L-1. In some embodiments, the method decreases protoporphyrin IX levels in the erythrocytes of the subject to levels less than 31 μmol L-1. In some embodiments, the method decreases protoporphyrin IX levels in the erythrocytes of the subject to levels less than 15 μmol L-1. In some embodiments, the method relates to decreasing protoporphyrin IX levels in the stool of the subject. In some embodiments, the method decreases protoporphyrin IX levels in the skin of the subject. In some embodiments, the method relates to methods of decreasing free-protoporphyrin IX levels in the subject by at least 10% (e.g., 10%, 15%, 20%, 25%, 30%, 35%, 40%, 45%, 50%, 55%, 60%, 65%, 70%, 75%, 80%, 85%, 90%, 95%, or at least 100%). In some embodiments, the method relates to methods of decreasing free-protoporphyrin IX levels in the subject by at least 15%. In some embodiments, the method relates to methods of decreasing free-protoporphyrin IX levels in the subject by at least 20%. In some embodiments, the method relates to methods of decreasing free-protoporphyrin IX levels in the subject by at least 25%. In some embodiments, the method relates to methods of decreasing free-protoporphyrin IX levels in the subject by at least 30%. In some embodiments, the method relates to methods of decreasing free-protoporphyrin IX levels in the subject by at least 35%. In some embodiments, the method relates to methods of decreasing free-protoporphyrin IX levels in the subject by at least 40%. In some embodiments, the method relates to methods of decreasing free-protoporphyrin IX levels in the subject by at least 45%. In some embodiments, the method relates to methods of decreasing free-protoporphyrin IX levels in the subject by at least 50%. In some embodiments, the method relates to methods of decreasing free-protoporphyrin IX levels in the subject by at least 55%. In some embodiments, the method relates to methods of decreasing free-protoporphyrin IX levels in the subject by at least 60%. In some embodiments, the method relates to methods of decreasing free-protoporphyrin IX levels in the subject by at least 65%. In some embodiments, the method relates to methods of decreasing free-protoporphyrin IX levels in the subject by at least 70%. In some embodiments, the method relates to methods of decreasing free-protoporphyrin IX levels in the subject by at least 75%. In some embodiments, the method relates to methods of decreasing free-protoporphyrin IX levels in the subject by at least 80%. In some embodiments, the method relates to methods of decreasing free-protoporphyrin IX levels in the subject by at least 85%. In some embodiments, the method relates to methods of decreasing free-protoporphyrin IX levels in the subject by at least 90%. In some embodiments, the method relates to methods of decreasing free-protoporphyrin IX levels in the subject by at least 95%. In some embodiments, the method relates to methods of decreasing free-protoporphyrin IX levels in the subject by at least 100%.

In certain aspects, the disclosure relates to methods of treating X-linked protoporphyria (XLPP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject has increased zinc-protoporphyrin IX (ZPPIX) levels. In some embodiments, the method relates to subjects having ZPPIX levels that are at least 10%, 20%, 30%, 40%, or 50% more than ZPPIX levels in a healthy subject prior to administration of the glycine transporter inhibitor (e.g., a GlyT1 inhibitor). In some embodiments, the method relates to subjects having ZPPIX levels that are at least 10% more than ZPPIX levels in a healthy subject prior to administration of the glycine transporter inhibitor (e.g., a GlyT1 inhibitor). In some embodiments, the method relates to subjects having ZPPIX levels that are at least 20% more than ZPPIX levels in a healthy subject prior to administration of the glycine transporter inhibitor (e.g., a GlyT1 inhibitor). In some embodiments, the method relates to subjects having ZPPIX levels that are at least 30% more than ZPPIX levels in a healthy subject prior to administration of the glycine transporter inhibitor (e.g., a GlyT1 inhibitor). In some embodiments, the method relates to subjects having ZPPIX levels that are at least 40% more than ZPPIX levels in a healthy subject prior to administration of the glycine transporter inhibitor (e.g., a GlyT1 inhibitor). In some embodiments, the method relates to subjects having ZPPIX levels that are at least 50% more than ZPPIX levels in a healthy subject prior to administration of the glycine transporter inhibitor (e.g., a GlyT1 inhibitor). In some embodiments, the subject has increased ZPPIX levels in erythrocytes.

In certain aspects, the disclosure relates to methods of treating X-linked protoporphyria (XLPP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject has increased proportion of zinc-protoporphyrin IX (ZPPIX) to free-protoporphyrin IX (ZPPIX/PPIX ratio) as compared to those with EPP. In some embodiments, the method relates to subjects having a ZPPIX/PPIX ratio that is at least 15% (e.g., 15%, 20%, 25%, 30%, 35%, 40%, or 45%). In some embodiments, the method relates to subjects having a ZPPIX/PPIX ratio that is at least 20%. In some embodiments, the method relates to subjects having a ZPPIX/PPIX ratio that is at least 25%. In some embodiments, the method relates to subjects having a ZPPIX/PPIX ratio that is at least 30%. In some embodiments, the method relates to subjects having a ZPPIX/PPIX ratio that is at least 35%. In some embodiments, the method relates to subjects having a ZPPIX/PPIX ratio that is at least 40%. In some embodiments, the method relates to subjects having a ZPPIX/PPIX ratio that is at least 45%.

In certain aspects, the disclosure relates to methods of inhibiting zinc protoporphyrin IX (ZPPIX) synthesis in vivo, comprising administering to a subject a GlyT1 inhibitor, or a pharmaceutically acceptable salt thereof, or a prodrug of the GlyT1 inhibitor or its pharmaceutically acceptable salt. In some embodiments, the disclosure relates to methods of inhibiting ZPPIX synthesis in vivo by at least 10% (e.g., 10%, 20%, 30%, 40%, 50%, 60%, 70%, 80%, 90%, or at least 100%). In some embodiments, the disclosure relates to methods of inhibiting ZPPIX synthesis in vivo by at least 20%. In some embodiments, the disclosure relates to methods of inhibiting ZPPIX synthesis in vivo by at least 30%. In some embodiments, the disclosure relates to methods of inhibiting ZPPIX synthesis in vivo by at least 40%. In some embodiments, the disclosure relates to methods of inhibiting ZPPIX synthesis in vivo by at least 50%. In some embodiments, the disclosure relates to methods of inhibiting ZPPIX synthesis in vivo by at least 60%. In some embodiments, the disclosure relates to methods of inhibiting ZPPIX synthesis in vivo by at least 70%. In some embodiments, the disclosure relates to methods of inhibiting ZPPIX synthesis in vivo by at least 80%. In some embodiments, the disclosure relates to methods of inhibiting ZPPIX synthesis in vivo by at least 90%. In some embodiments, the disclosure relates to methods of inhibiting ZPPIX synthesis in vivo by at least 100%.

In certain aspects, the disclosure relates to methods of treating erythropoietic protoporphyria (EPP), X-linked protoporphyria (XLPP), or congenital erythropoietic porphyria (CEP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject has increased 5-aminolevulinic acid (5-ALA) levels. In some embodiments, the method relates to subjects having 5-ALA levels that are at least 10%, 20%, 30%, 40%, or 50% more than 5-ALA levels in a healthy subject prior to administration of the glycine transporter inhibitor (e.g., a GlyT1 inhibitor). In some embodiments, the method relates to subjects having 5-ALA levels that are at least 10% more than 5-ALA levels in a healthy subject prior to administration of the glycine transporter inhibitor (e.g., a GlyT1 inhibitor). In some embodiments, the method relates to subjects having 5-ALA levels that are at least 20% more than 5-ALA levels in a healthy subject prior to administration of the glycine transporter inhibitor (e.g., a GlyT1 inhibitor). In some embodiments, the method relates to subjects having 5-ALA levels that are at least 30% more than 5-ALA levels in a healthy subject prior to administration of the glycine transporter inhibitor (e.g., a GlyT1 inhibitor). In some embodiments, the method relates to subjects having 5-ALA levels that are at least 40% more than 5-ALA levels in a healthy subject prior to administration of the glycine transporter inhibitor (e.g., a GlyT1 inhibitor). In some embodiments, the method relates to subjects having 5-ALA levels that are at least 50% more than 5-ALA levels in a healthy subject prior to administration of the glycine transporter inhibitor (e.g., a GlyT1 inhibitor).

In certain aspects, the disclosure relates to methods of inhibiting 5-aminolevulinic acid (5-ALA) synthesis in vivo, comprising administering to a subject a GlyT1 inhibitor, or a pharmaceutically acceptable salt thereof, or a prodrug of the GlyT1 inhibitor or its pharmaceutically acceptable salt. In some embodiments, the disclosure relates to methods of inhibiting 5-ALA synthesis in vivo by at least 10% (e.g., 10%, 20%, 30%, 40%, 50%, 60%, 70%, 80%, 90%, or at least 100%). In some embodiments, the disclosure relates to methods of inhibiting 5-ALA synthesis in vivo by at least 20%. In some embodiments, the disclosure relates to methods of inhibiting 5-ALA synthesis in vivo by at least 30%. In some embodiments, the disclosure relates to methods of inhibiting 5-ALA synthesis in vivo by at least 40%. In some embodiments, the disclosure relates to methods of inhibiting 5-ALA synthesis in vivo by at least 50%. In some embodiments, the disclosure relates to methods of inhibiting 5-ALA synthesis in vivo by at least 60%. In some embodiments, the disclosure relates to methods of inhibiting 5-ALA synthesis in vivo by at least 70%. In some embodiments, the disclosure relates to methods of inhibiting 5-ALA synthesis in vivo by at least 80%. In some embodiments, the disclosure relates to methods of inhibiting 5-ALA synthesis in vivo by at least 90%. In some embodiments, the disclosure relates to methods of inhibiting 5-ALA synthesis in vivo by at least 100%.

The present application further provides use of one or more glycine transporter inhibitor, or a pharmaceutically acceptable salt thereof, or a prodrug of the one or more glycine transporter inhibitor or its pharmaceutically acceptable salt, in the manufacture of a formulation for the treatment of EPP, XLPP, CEP or related syndrome thereof (e.g., EPP-related syndrome, XLPP-related syndrome, or CEP-related syndrome) in a subject. In some embodiments, the present application provides use of one or more glycine transporter inhibitor, or a pharmaceutically acceptable salt thereof, or a prodrug of the one or more glycine transporter inhibitor or its pharmaceutically acceptable salt, in the manufacture of a formulation for the treatment of EPP, XLPP, or CEP in a subject. In some embodiments, the one or more glycine transporter inhibitor is one or more GlyT1 and/or GlyT2 inhibitors. In some embodiments, the one or more glycine transporter inhibitor is one or more GlyT1 inhibitor, such as one or more GlyT1 inhibitor as disclosed herein. In certain such embodiments, the GlyT1 inhibitor is bitopertin, or a pharmaceutically acceptable salt thereof, or a prodrug of bitopertin or its pharmaceutically acceptable salt. In certain embodiments of the foregoing, the formulation is administered in a therapeutically effective amount.

The present application provides the use of one or more glycine transporter inhibitor, or a pharmaceutically acceptable salt thereof, or a prodrug of the one or more glycine transporter inhibitor or its pharmaceutically acceptable salt, in the manufacture of a pharmaceutical composition for the treatment of EPP, XLPP, or CEP, or related syndrome thereof (e.g., EPP-related syndrome, XLPP-related syndrome, or CEP-related syndrome) in a subject. In some embodiments, the present application provides the use of one or more glycine transporter inhibitor, or a pharmaceutically acceptable salt thereof, or a prodrug of the one or more glycine transporter inhibitor or its pharmaceutically acceptable salt, in the manufacture of a pharmaceutical composition for the treatment of EPP, XLPP, or CEP, in a subject. In some embodiments, the one or more glycine transporter inhibitor is one or more GlyT1 and/or GlyT2 inhibitors. In some embodiments, the one or more glycine transporter inhibitor is one or more GlyT1 inhibitor, such as one or more GlyT1 inhibitor as disclosed herein. In certain such embodiments, the GlyT1 inhibitor is bitopertin, or a pharmaceutically acceptable salt thereof, or a prodrug of bitopertin or its pharmaceutically acceptable salt. In certain embodiments of the foregoing, the pharmaceutical composition further comprises a pharmaceutically acceptable carrier.

Congenital erythropoietic porphyria (CEP) is an erythropoietic cutaneous porphyria characterized by blistering cutaneous photosensitivity. Severe cases of CEP can present in utero with hydrops fetalis, or shortly after birth with severe blistering photosensitivity, red urine, splenomegaly, hemolysis, and transfusion dependence. Milder cases and later onset forms typically present with red urine, severe blistering, and hemolytic anemia.

CEP individuals are often homozygous or compound heterozygous for UROS mutations. Some cases of CEP are due to mutations in the gene encoding the transcriptional regulator GATA1. These mutations result in reduced enzyme activity of uroporphyrinogen III synthase (UROIII-S), the fourth enzyme in the heme biosynthetic pathway. The decreased activity of UROIII-S leads to an accumulation of hydroxymethylbilane which spontaneously forms uroporphyrinogen I, which is further metabolized to coproporphyrinogen I. Uroporphyrinogen I and coproporphyrinogen I accumulate in the tissues.

The diagnosis of CEP can be determined by analyzing the enzyme activity of uroporphyrinogen III synthase (UROIII-S), by evaluating mutations in the UROS gene, by evaluating the function of GATA-1 erythroid-specific transcription factor, by evaluating mutations in GATA1, and by determining the levels of uroporphyrin I and coproporphyrin I in the subject. In some embodiments, the subject has a mutation in UROS. In some embodiments, the subject has a gene defect in GATA-1 erythroid-specific transcription factor. In some embodiments, the method relates to methods of treating a subject, wherein the subject has decreased activity of uroporphyrinogen III synthase. In some embodiments, the increased levels of uroporphyrin I and/or coproporphyrin I are measured in the subject's urine or red blood cells. In some embodiments, the increased levels of coproporphyrin I are measured in the subject's stool.

In certain aspects, the disclosure relates to methods of treating congenital erythropoietic porphyria (CEP) in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject has increased uroporphyrin I and/or coproporphyrin I levels. In some embodiments, the subject has increased levels of uroporphyrin I and/or coproporphyrin I. In some embodiments, the method relates to subjects having uroporphyrin I levels that are at least 10%, 20%, 30%, 40%, or 50% more than uroporphyrin I levels in a healthy subject prior to administration of the glycine transporter inhibitor (e.g., a GlyT1 inhibitor). In some embodiments, the method relates to subjects having uroporphyrin I levels that are at least 10% more than uroporphyrin I levels in a healthy subject prior to administration of the glycine transporter inhibitor (e.g., a GlyT1 inhibitor). In some embodiments, the method relates to subjects having uroporphyrin I levels that are at least 20% more than uroporphyrin I levels in a healthy subject prior to administration of the glycine transporter inhibitor (e.g., a GlyT1 inhibitor). In some embodiments, the method relates to subjects having uroporphyrin I levels that are at least 30% more than uroporphyrin I levels in a healthy subject prior to administration of the glycine transporter inhibitor (e.g., a GlyT1 inhibitor). In some embodiments, the method relates to subjects having uroporphyrin I levels that are at least 40% more than uroporphyrin I levels in a healthy subject prior to administration of the glycine transporter inhibitor (e.g., a GlyT1 inhibitor). In some embodiments, the method relates to subjects having uroporphyrin I levels that are at least 50% more than uroporphyrin I levels in a healthy subject prior to administration of the glycine transporter inhibitor (e.g., a GlyT1 inhibitor).

In some embodiments, the disclosure relates to methods of treating subjects having coproporphyrin I levels that are at least 10%, 20%, 30%, 40%, or 50% more than coproporphyrin I levels in a healthy subject prior to administration of the glycine transporter inhibitor (e.g., a GlyT1 inhibitor). In some embodiments, the method relates to subjects having coproporphyrin I levels that are at least 10% more than coproporphyrin I levels in a healthy subject prior to administration of the glycine transporter inhibitor (e.g., a GlyT1 inhibitor). In some embodiments, the method relates to subjects having coproporphyrin I levels that are at least 20% more than coproporphyrin I levels in a healthy subject prior to administration of the glycine transporter inhibitor (e.g., a GlyT1 inhibitor). In some embodiments, the method relates to subjects having coproporphyrin I levels that are at least 30% more than coproporphyrin I levels in a healthy subject prior to administration of the glycine transporter inhibitor (e.g., a GlyT1 inhibitor). In some embodiments, the method relates to subjects having coproporphyrin I levels that are at least 40% more than coproporphyrin I levels in a healthy subject prior to administration of the glycine transporter inhibitor (e.g., a GlyT1 inhibitor). In some embodiments, the method relates to subjects having coproporphyrin I levels that are at least 50% more than coproporphyrin I levels in a healthy subject prior to administration of the glycine transporter inhibitor (e.g., a GlyT1 inhibitor).

In certain aspects, the disclosure relates to methods of inhibiting uroporphyrin I and/or coproporphyrin I synthesis in vivo, comprising administering to a subject a glycine transporter inhibitor (e.g., a GlyT1 inhibitor), or a pharmaceutically acceptable salt thereof, or a prodrug of the glycine transporter inhibitor (e.g., a GlyT1 inhibitor) or its pharmaceutically acceptable salt. In some embodiments, the disclosure relates to methods of inhibiting uroporphyrin I synthesis in vivo by at least 10% (e.g., 10%, 20%, 30%, 40%, 50%, 60%, 70%, 80%, 90%, or at least 100%). In some embodiments, the disclosure relates to methods of inhibiting uroporphyrin I synthesis in vivo by at least 20%. In some embodiments, the disclosure relates to methods of inhibiting uroporphyrin I synthesis in vivo by at least 30%. In some embodiments, the disclosure relates to methods of inhibiting uroporphyrin I synthesis in vivo by at least 40%. In some embodiments, the disclosure relates to methods of inhibiting uroporphyrin I synthesis in vivo by at least 50%. In some embodiments, the disclosure relates to methods of inhibiting uroporphyrin I synthesis in vivo by at least 60%. In some embodiments, the disclosure relates to methods of inhibiting uroporphyrin I synthesis in vivo by at least 70%. In some embodiments, the disclosure relates to methods of inhibiting uroporphyrin I synthesis in vivo by at least 80%. In some embodiments, the disclosure relates to methods of inhibiting uroporphyrin I synthesis in vivo by at least 90%. In some embodiments, the disclosure relates to methods of inhibiting uroporphyrin I synthesis in vivo by at least 100%.

In some embodiments, the disclosure relates to methods of inhibiting coproporphyrin I synthesis in vivo by at least 10% (e.g., 10%, 20%, 30%, 40%, 50%, 60%, 70%, 80%, 90%, or at least 100%). In some embodiments, the disclosure relates to methods of inhibiting coproporphyrin I synthesis in vivo by at least 20%. In some embodiments, the disclosure relates to methods of inhibiting coproporphyrin I synthesis in vivo by at least 30%. In some embodiments, the disclosure relates to methods of inhibiting coproporphyrin I synthesis in vivo by at least 40%. In some embodiments, the disclosure relates to methods of inhibiting coproporphyrin I synthesis in vivo by at least 50%. In some embodiments, the disclosure relates to methods of inhibiting coproporphyrin I synthesis in vivo by at least 60%. In some embodiments, the disclosure relates to methods of inhibiting coproporphyrin I synthesis in vivo by at least 70%. In some embodiments, the disclosure relates to methods of inhibiting coproporphyrin I synthesis in vivo by at least 80%. In some embodiments, the disclosure relates to methods of inhibiting coproporphyrin I synthesis in vivo by at least 90%. In some embodiments, the disclosure relates to methods of inhibiting coproporphyrin I synthesis in vivo by at least 100%.

Porphyrins (e.g., PPIX, ZPPIX, uroporphyrin I, and coproporphyrin I) can be found in various biological samples including the skin, urine, stool, plasma, and erythrocytes. In some embodiments, the porphyrins may be extracted from the biological sample into a solution for fluorescence analysis. Porphyrins can be detected in these biological samples by direct inspection using long wavelength ultraviolet light (e.g., 400-420 nm light). Porphyrins have the greatest absorption wavelengths near 400-420 nm, with their highest absorption peak occurring at 415 nm. The emission maxima of porphyrins is typically around 600 nm and varies slightly based on the type of porphyrins and the solvent used for analysis. In some embodiments, diagnosis of EPP, XLPP, and CEP may be made using fluorescence analysis. In some embodiments, skin porphyrin levels (e.g., PPIX levels) can be measured by calculating the difference before and after complete photobleaching of PPIX using controlled illumination. See, e.g., Heerfordt IM. Br J Dermatol. 2016; 175(6):1284-1289.

In some embodiments, the subject's plasma porphyrin fluoresces at a peak of 634 nm when illuminated with blue light (e.g., 400-420 nm light). In some embodiments, the subject's plasma porphyrin fluoresces at a peak between 626 nm and 634 nm when illuminated with blue light (e.g., 400-420 nm light). In some embodiments, the subject's skin porphyrin fluoresces at a peak of 632 nm when illuminated with blue light (e.g., 400-420 nm light). In some embodiments, the subject's skin porphyrin fluoresces at a peak between 626 nm and 634 nm when illuminated with blue light (e.g., 400-420 nm light). In some embodiments, the subject has greater than 0.2 FluoDerm Units (FDU) of protoporphyrin IX levels in the skin. In some embodiments, the subject has greater than 1.0 FDU of protoporphyrin IX levels in the skin. In some embodiments, the subject has between 1.0 FDU and 2.5 FDU of protoporphyrin IX levels in the skin. In some embodiments, the subject has greater than 2.5 FDU of protoporphyrin IX levels in the skin. In some embodiments, the method decreases protoporphyrin IX levels in the skin of the subject to less than 0.5 FDU. In some embodiments, the method decreases protoporphyrin IX levels in the skin of the subject to less than 1.0 FDU. In some embodiments, the method decreases protoporphyrin IX levels in the skin of the subject to less than 1.5 FDU. In some embodiments, the method decreases protoporphyrin IX levels in the skin of the subject to less than 2.0 FDU. In some embodiments, the method decreases protoporphyrin IX levels in the skin of the subject to less than 2.5 FDU. In some embodiments, the subject has red fluorescent urine. In some embodiments, the subject has a peak between 615 nm and 620 nm using plasma porphyrin fluorescence analysis.

In certain aspects, the disclosure relates to methods of preventing, treating, or reducing the progression rate and/or severity of one or more complications of EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the one or more complications of EPP, XLPP, or CEP is selected from the group consisting of: acute photosensitivity, cutaneous photosensitivity, edema, erythema, anemia, hypochromic anemia, hemolytic anemia, hemolysis, mild hemolysis, severe hemolysis, chronic hemolysis, hypersplenism, palmar keratoderma, bullae, lesions, scarring, deformities, loss of fingernails, loss of digits, cholelithiasis, cholestasis, cytolysis, gallstones, cholestatic liver failure, erythrodontia, hypercellular bone marrow, myelodysplasia, thrombocytopenia, hydrops fetalis and/or death in utero. In some embodiments, the disclosure contemplates methods of treating one or more complications of EPP, XLPP, or CEP (e.g., acute photosensitivity, cutaneous photosensitivity, edema, erythema, anemia, hypochromic anemia, hemolytic anemia, hemolysis, mild hemolysis, severe hemolysis, chronic hemolysis, hypersplenism, palmar keratoderma, bullae, lesions, scarring, deformities, loss of fingernails, loss of digits, cholelithiasis, cholestasis, cytolysis, gallstones, cholestatic liver failure, erythrodontia, hypercellular bone marrow, myelodysplasia, thrombocytopenia, hydrops fetalis and/or death in utero) comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the one or more complications are improved indirectly. In some embodiments, the disclosure contemplates methods of preventing one or more complications of EPP, XLPP, or CEP comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure contemplates methods of reducing the progression rate of one or more complications of EPP, XLPP, or CEP comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure contemplates methods of reducing the severity of one or more complications of EPP, XLPP, or CEP comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt.

Optionally, methods disclosed herein for preventing, treating, or reducing the progression rate and/or severity of one or more complications of EPP, XLPP, or CEP in a subject, may further comprise administering to the patient one or more supportive therapies or additional active agents for treating EPP, XLPP, or CEP. For example, the patient also may be administered one or more supportive therapies or active agents selected from the group consisting of: avoiding sunlight, topical sunscreens, skin protection, UVB phototherapy, Afamelanotide (Scenesse®), bortezomib, proteasome inhibitors, chemical chaperones, cholestyramine, activated charcoal, iron supplementation, liver transplantation, bone marrow transplantation, splenectomy, and blood transfusion. In some embodiments, the methods described herein may further comprise administering to the patient Afamelanotide (Scenesse®).

Porphyrin photosensitization in EPP, XLPP, and CEP produces two distinct clinical syndromes: (1) acute photosensitivity on exposure to sunlight with erythema and edema and (2) a syndrome wherein subepidermal bullae occur in sun-exposed areas of the skin. In certain aspects, the disclosure relates to methods of preventing, treating, or reducing the progression rate and/or severity of EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the method increases pain free light exposure in the subject. In some embodiments, the method increases pain free light exposure in the subject by at least 10%, 20%, 30%, 40%, or 50% more as compared to pain free light exposure prior to administration of the GlyT1 inhibitor. In some embodiments, the method decreases light sensitivity in the subject. In some embodiments, the method decreases light sensitivity in the subject by at least 10%, 20%, 30%, 40%, or 50% more as compared to light sensitivity prior to administration of the GlyT1 inhibitor. In some embodiments, the subject has a history of phototoxic reactions from EPP. In some embodiments, the subject is an adult, child, infant, or pregnant woman.

Glycine is one of the key initial substrates for heme and globin synthesis. As such, decreased levels of glycine due to GlyT1 inhibition could lead to a decrease in heme synthesis. In certain aspects, the disclosure relates to methods of treating EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject's heme levels decrease no more than 10% (e.g., 10%, 15%, 20%, 25%, and 30%). In some embodiments, the disclosure relates to methods of treating EPP, XLPP, or CEP in a subject, wherein the subject's heme levels decrease no more than 15%. In some embodiments, the disclosure relates to methods of treating EPP, XLPP, or CEP in a subject, wherein the subject's heme levels decrease no more than 20%. In some embodiments, the disclosure relates to methods of treating EPP, XLPP, or CEP in a subject, wherein the subject's heme levels decrease no more than 25%. In some embodiments, the disclosure relates to methods of treating EPP, XLPP, or CEP in a subject, wherein the subject's heme levels decrease no more than 30%.

In certain aspects, the disclosure relates to methods of treating EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the subject's PPIX levels decrease while the patient's heme levels are substantially maintained. In some embodiments, the patients PPIX levels decrease by at least 50% (e.g., 50%, 55%, 60%, 65%, 70%, 75%, 80%, 85%, 90%, 95%, or at least 100%) and the patient's heme levels decrease no more than 10% (e.g., 10%, 15%, 20%, 25%, and 30%). In some embodiments, the patient's PPIX levels decrease by at least 85% and the patient's heme levels decrease no more than 15%. In some embodiments, the patients PPIX levels decrease by at least 80% and the patient's heme levels decrease no more than 15%. In some embodiments, the patients PPIX levels decrease by at least 75% and the patient's heme levels decrease no more than 15%. In some embodiments, the patients PPIX levels decrease by at least 70% and the patient's heme levels decrease no more than 15%. In some embodiments, the patients PPIX levels decrease by at least 65% and the patient's heme levels decrease no more than 15%. In some embodiments, the patients PPIX levels decrease by at least 60% and the patient's heme levels decrease no more than 15%. In some embodiments, the patients PPIX levels decrease by at least 55% and the patient's heme levels decrease no more than 15%. In some embodiments, the patients PPIX levels decrease by at least 50% and the patient's heme levels decrease no more than 15%.

In certain aspects, the disclosure relates to methods of treating EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt, wherein the dosage of the pharmaceutical composition does not cause a substantial reduction in heme levels. In some embodiments, the patient's PPIX levels decrease by at least 50% (e.g., 50%, 55%, 60%, 65%, 70%, 75%, 80%, 85%, 90%, 95%, or at least 100%). In some embodiments, the patient's PPIX levels decrease by at least 55%. In some embodiments, the patient's PPIX levels decrease by at least 60%. In some embodiments, the patient's PPIX levels decrease by at least 65%. In some embodiments, the patient's PPIX levels decrease by at least 70%. In some embodiments, the patient's PPIX levels decrease by at least 75%. In some embodiments, the patient's PPIX levels decrease by at least 80%. In some embodiments, the patient's PPIX levels decrease by at least 85%. In some embodiments, the patient's PPIX levels decrease by at least 90%. In some embodiments, the patient's PPIX levels decrease by at least 95%. In some embodiments, the patient's PPIX levels decrease by at least 100%. In some embodiments, the patient's heme levels decrease no more than 10% (e.g., 10%, 15%, 20%, 25%, and 30%). In some embodiments, the patient's heme levels decrease no more than 15%. In some embodiments, the patient's heme levels decrease no more than 20%. In some embodiments, the patient's heme levels decrease no more than 25%. In some embodiments, the patient's heme levels decrease no more than 30%.

In some embodiments, the accumulation of one or more of the following heme intermediates is inhibited, wherein the one or more heme intermediates is selected from the group consisting of PPIX, ZPPIX, uroporphyrin I, coproporphyrin I, and/or 5-ALA. In some embodiments, the disclosure relates to methods of inhibiting the accumulation of PPIX, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure relates to methods of inhibiting the accumulation of ZPPIX, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure relates to methods of inhibiting the accumulation of uroporphyrin I, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure relates to methods of inhibiting the accumulation of coproporphyrin I, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the disclosure relates to methods of inhibiting the accumulation of 5-ALA, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the accumulation of the one or more heme intermediates (e.g., PPIX, ZPPIX, uroporphyrin I, coproporphyrin I, and/or 5-ALA) is inhibited in a dose dependent manner. See, e.g., FIG. 7.

Protoporphyrin accumulation in EPP, XLPP, and CEP can cause liver damage when the hepatic load exceeds the canalicular excretion capacity. The accumulation of PPIX in hepatocytes and bile canaliculi may result in cell damage, cholestasis, cytolysis and further retention of protoporphyrin. Excess protoporphyrin can exert cholestatic effects leading to changes in the hepatobiliary system which can range from mild inflammation to fibrosis and cirrhosis (e.g., cholelithiasis, mild liver disease, deteriorating liver disease, and terminal phase liver disease). Between 3-5% of patients with EPP or XLPP develop protoporphyric hepatopathy, a severe liver disease that can progress rapidly and require liver transplantation. Approximately 2% of patients will develop severe liver disease.

In certain aspects, the disclosure relates to methods of preventing, treating, or reducing the progression rate and/or severity of liver disease associated with EPP, XLPP, or CEP in a subject, the method comprising administering to the subject a pharmaceutical composition comprising one or more glycine transporter inhibitor (e.g., a GlyT1 inhibitor), or a pharmaceutically acceptable salt thereof, or a prodrug of the one or more glycine transporter inhibitor (e.g., a GlyT1 inhibitor) or its salt. In some embodiments, the liver disease associated with EPP, XLPP, or CEP is cholelithiasis. In some embodiments, the liver disease associated with EPP, XLPP, or CEP is mild liver disease. In some embodiments, the liver disease associated with EPP, XLPP, or CEP is deteriorating liver disease. In some embodiments, the liver disease associated with EPP, XLPP, or CEP is terminal phase liver disease.

Liver function in patients with EPP, XLPP, and CEP can be assessed using various known clinical assays. In some embodiments, liver function tests can be used to determine the level of various biochemical parameters (e.g., raised aspartate transaminase levels, alkaline phosphatase, or γ-glutamyl transferase levels). In some embodiments, histopathology of liver biopsies may be used to assess one or more parameters (e.g., protoporphyrin deposition, fibrosis, infiltrates, portal fibrosis, and periportal fibrosis) in the subject. In some embodiments, ultrastructural studies of biopsy specimen can be used to determine if crystal containing vacuoles are present in the subject. With deterioration of liver function, urinary coproporphyrin excretion increases. In some embodiments, coproporphyrin excretion in the urine may be analyzed to assess liver function in the subject. In some embodiments, ultrasound or magnetic resonance elastography may be used to measure liver stiffness in the subject.

In certain embodiments of the methods and uses as disclosed herein, the glycine transporter inhibitor, such as a GlyT1 inhibitor (e.g., a GlyT1 inhibitor as disclosed herein), or a pharmaceutically acceptable salt thereof, or a prodrug of the glycine transporter inhibitor, such as a GlyT1 inhibitor (e.g., a GlyT1 inhibitor as disclosed herein), or its pharmaceutically acceptable salt, demonstrates PPIX inhibition with an EC50 of less than 500 nM, less than 400 nM, less than 300 nM, less than 200 nM, or less than 100 nM. In certain embodiments of the present application, the glycine transporter inhibitor, such as a GlyT1 inhibitor (e.g., a GlyT1 inhibitor as disclosed herein), or a pharmaceutically acceptable salt thereof, or a prodrug of the glycine transporter inhibitor, such as a GlyT1 inhibitor (e.g., a GlyT1 inhibitor as disclosed herein), or its pharmaceutically acceptable salt, demonstrates PPIX inhibition with an EC50 of less than 100 nM. In certain embodiments of the present application, the glycine transporter inhibitor, such as a GlyT1 inhibitor (e.g., a GlyT1 inhibitor as disclosed herein), or a pharmaceutically acceptable salt thereof, or a prodrug of the glycine transporter inhibitor, such as a GlyT1 inhibitor (e.g., a GlyT1 inhibitor as disclosed herein), or its pharmaceutically acceptable salt, demonstrates PPIX inhibition with an EC50 of less than 50 nM. In certain such embodiments, the EC50 is measured in a flow cytometry assay. In certain embodiments of the foregoing, the GlyT1 inhibitor is bitopertin, or a pharmaceutically acceptable salt thereof, or a prodrug of bitopertin or its pharmaceutically acceptable salt.

In certain embodiments of the methods and uses as disclosed herein, at least 50%, at least 60%, at least 70%, at least 80%, at least 85%, at least 90%, or at least 95% cell viability is maintained. In certain such embodiments, at least 90% cell viability is maintained.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner. Throughout these examples, there may be molecular cloning reactions, and other standard recombinant DNA techniques described and these were carried out according to methods described in Maniatis et al., Molecular Cloning—A Laboratory Manual, 2nd ed., Cold Spring Harbor Press (1989), using commercially available reagents, except where otherwise noted.

The following examples are illustrative, but not limiting, of the methods and compositions described herein. Other suitable modifications and adaptations of the variety of conditions and parameters normally encountered in therapy, synthesis, and other embodiments disclosed herein are within the spirit and scope of the embodiments.

EXAMPLES

Example 1: Synthesis of Compounds

The compounds disclosed herein can be made in accordance with well known procedures and by processes known and disclosed in the art. For example, compounds of Formula I, such as bitopertin, can be prepared in accordance with the synthetic protocols provided in U.S. Pat. Nos. 7,319,099, 9,877,963, and 7,812,161, the contents of which are hereby incorporated by reference in their entirety. In addition, compounds of Formula II, such as PF-3463275, can be prepared in accordance with the synthetic protocols provided in U.S. Pat. No. 8,124,639, the contents of which are hereby incorporated by reference in its entirety.

Example 2: GlyT1 Inhibitors to Treat Subjects with Erythropoietic Protoporphyrias (EPP), X-Linked Protoporphyria (XLPP), and Congenital Erythropoietic Porphyria (CEP). (Prophetic Example)

The synthesis of large amounts of heme is a fundamental requirement in the developing erythroid cell in order to support the production of large amounts of hemoglobin. In this cell lineage, the amount of heme needed to meet this demand is greatly in excess of any other cell type. Heme synthesis is initiated with the condensation of glycine with succinyl CoA by the enzyme ALAS. This is the rate-limiting step in heme biosynthesis to ensure that heme intermediates do not accumulate and cause toxicity. Erythroid cells have acquired an erythroid specific form of ALAS (ALAS2) and the glycine transporter GlyT1 to increase glycine availability in order to meet this high demand for heme.

Animal and human studies in which the activity of GlyT1 is eliminated by gene deletion (Garcia-Santos et al, 2017) or decreased by administration of a specific GlyT1 inhibitor (Pinard et al, 2018) have been shown to reduce heme synthesis in erythroid cells, leading to moderate microcytic hypochromic anemia as a consequence of impaired hemoglobin production. These findings indicate that modulation of glycine uptake in red cells is able to regulate the heme biosynthetic pathway.

In patients with either the erythropoietic protoporphyrias or congenital erythropoietic porphyria specific mutations in individual genes encoding enzymes of the heme biosynthetic pathway lead to altered enzyme activity and the accumulations of heme intermediates upstream of the affected enzyme. Accumulation of these metabolites occurs because the mutated enzyme becomes the rate-limiting step in the pathway with activity that is insufficient to fully convert the upstream metabolite to the next step in the pathway. Three diseases are of specific interest:

1. EPP caused by mutations in the ferrochetalase gene that leads to reduced activity of this enzyme and accumulation of the upstream metabolite protoporphyrin IX (PPIX). Rarely EPP may be observed in an acquired form in older humans who have developed a novel clone containing a ferrochetalase mutation as a feature of myelodysplasia
2. XLPP caused by activating mutations in the ALAS2 gene, leading to high levels of PPIX. In this case, the accumulating metabolite is downstream of the affected enzyme because of overproduction that cannot be fully converted to heme even by normal levels of ferrochetalase.
3. CEP caused by mutations in the gene for uroporphyrinogen synthase resulting in reduced activity of this enzyme and accumulation of the upstream metabolite coproporphyrin I.

These heme intermediates may escape the red cell either by hemolysis of the cell (in CEP) or by active transport out of the cell (in EPP and XLPP) and cause toxicity. A consistent feature of all three diseases is a severe, painful, blistering skin reactions following exposure to sunlight that causes permanent scarring and deformity. This is caused by the local production of reactive intermediates by the action of sunlight on PPIX or coproporphyrin I that provokes a severe inflammatory reaction. PPIX is hydrophobic and therefore excreted through the biliary tract. High biliary concentrations may lead to cholelithiasis, cholestasis, and hepatic damage which can be severe, leading to hepatic failure. In the case of CEP, accumulation of coproporphyrin within the mature red cell may lead to severe hemolytic anemia.

These disease manifestations of EPP, XLPP and CEP are caused by overproduction of intermediate heme metabolites due to genetic abnormalities in the heme biosynthetic pathway. The accumulated metabolites are either toxic to the red cell, following accumulation in the skin and exposure to sunlight, or because of biliary excretion by the liver. GlyT1 controls the availability of one of the initial substrates in the heme biosynthetic pathway and has been shown to down-regulate heme production in humans or animals with a normal heme pathway as described above. Without being bound to any particular theory, GlyT1 is able to reduce the production of intermediate metabolites of heme in the same way, particularly when those intermediate products accumulate as a result of abnormal enzyme activity. Therefore, a subject with EPP, XLPP or CEP is treated with a GlyT1, which will reduce of the production of toxic metabolites in erythroid cells in such subjects and leads to a reduction in skin accumulation of these metabolites, reduced hepatobiliary excretion, or in the case of CEP a reduction in hemolysis, in all cases a reduction in disease severity. Thus, the disease is treated.

Example 3: Met GlyT1 Inhibitors are Effective to Reduce the Level of Heme Metabolites in Erythroleukemia Cell Lines Containing Disease-Causing Mutations for EPP, XLPP or CEP Erythroleukemia cells are genetically modified to obtain cell lines containing disease-causing mutations for EPP, XLPP or CEP. These genetically modified cell lines are treated with GlyT1 inhibitors and the production of heme metabolites is evaluated photometrically, biochemically or in radiolabel studies. The level of photohemolysis caused by PPIX is assessed in these cell lines and is found to be reduced in the presence of GlyT1 inhibitors.

Example 4: GlyT1 Inhibitors are Effective to Reduce the Level of Heme Metabolites in Erythroid Cells Containing Disease-Causing Mutations for EPP, XLPP or CEP. (Prophetic Example)

Erythroid cells are taken from bone marrow or peripheral blood of animals with disease causing mutations in the specific genes responsible for EPP, XLPP or CEP. These cell lines are treated with GlyT1 inhibitors and the production of heme metabolites is evaluated photometrically, biochemically or in radiolabel studies. The level of photohemolysis caused by PPIX is assessed in these cell lines and is found to be reduced in the presence of GlyT1 inhibitors.

Example 5: GlyT1 Inhibitors are Effective to Reduce the Level of Heme Metabolites in Patients' Erythroid Cells Containing Disease-Causing Mutations for EPP, XLPP or CEP. (Prophetic Example)

Erythroid cells (reticulocytes and erythrocytes) are obtained from patients with EPP, XLPP and CEP (as available). These cells from patients are treated with GlyT1 inhibitors and the production of heme metabolites is evaluated photometrically, biochemically or in radiolabel studies. The level of photohemolysis caused by PPIX is assessed in these cell lines and is found to be reduced in the presence of GlyT1 inhibitors.

Example 6: GlyT1 Inhibitors are Effective to Reduce the Severity of EPP or XLPP in Animals. (Prophetic Example)

Animals with EPP and XLPP are treated over a period with one or more GlyT1 inhibitors at various doses. The level of toxic heme intermediates in such animals is found to be reduced and the symptoms of such diseases, such as the severity of cutaneous reactions, hepatobiliary disease and/or hemolysis are found to be ameliorated.

The embodiments and examples provided herein demonstrate that the GlyT1 inhibitors can be used to treat EPP, XLPP, or CEP. This is a surprising and unexpected result.

Example 7: EPP Cellular Model

Knockout guide sequences were designed to target Exon3 of the Ferrochelatase gene. Guide sequences tested are shown in Table 1.

TABLE 1

| Guide sequences tested | | | |
|---|---|---|---|
| FECH_gRNA_3_KO | ATGGGAGGCCCTGAAACTCT (SEQ ID NO: 1) | gRNA | Exon3 |
| FECH_gRNA_4_KO | TGAAACTCTTGGAGATGTTC (SEQ ID NO: 2) | gRNA | Exon3 |
| FECH_gRNA_5_KO | TCTGAGACTCTTCTTGGACC (SEQ ID NO: 3) | gRNA | Exon3 |

Figure 2:
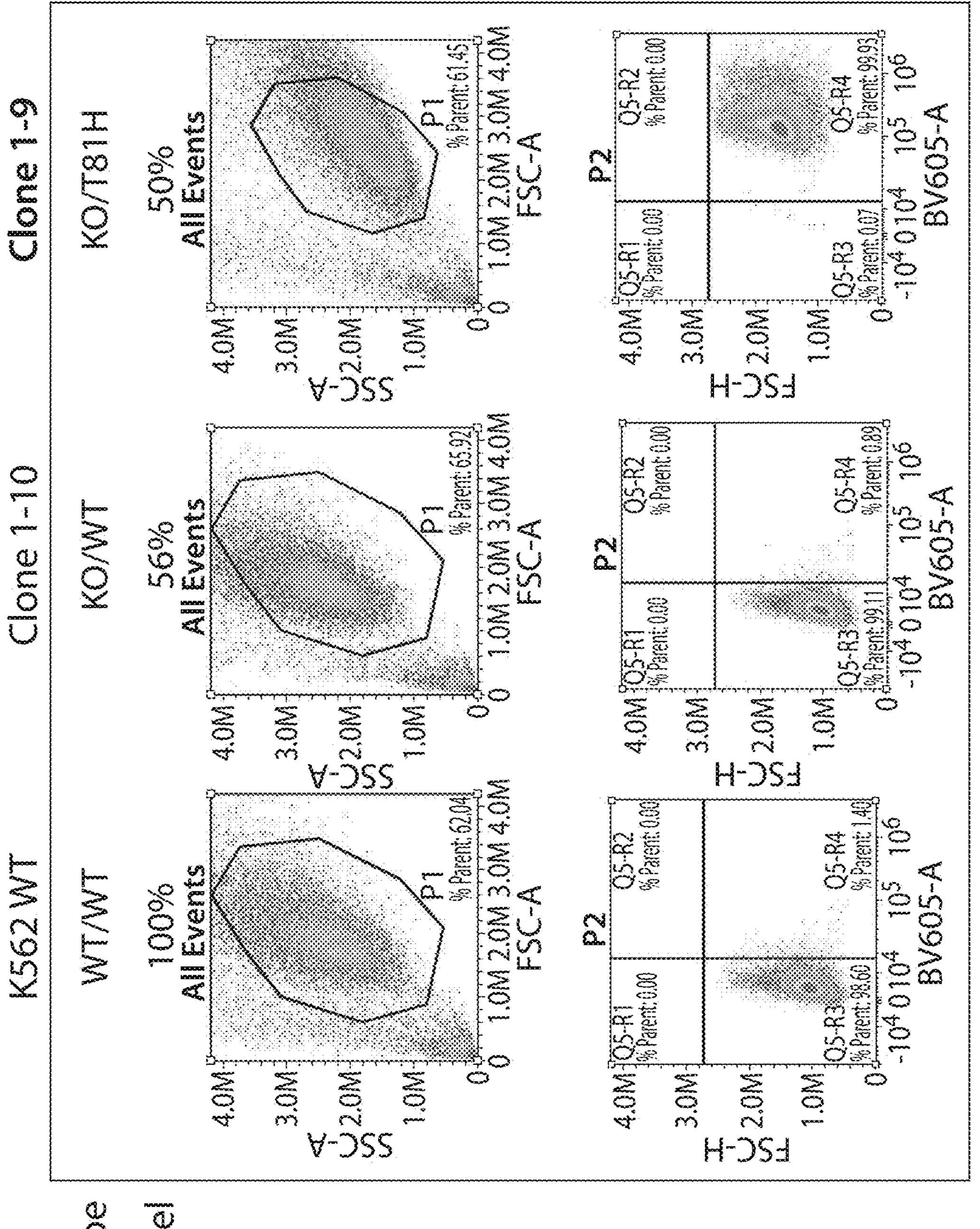
FIG. 2 shows flow cytometry determination of protoporphyrin IX (PPIX) levels for K562 clones.
Figure 3:
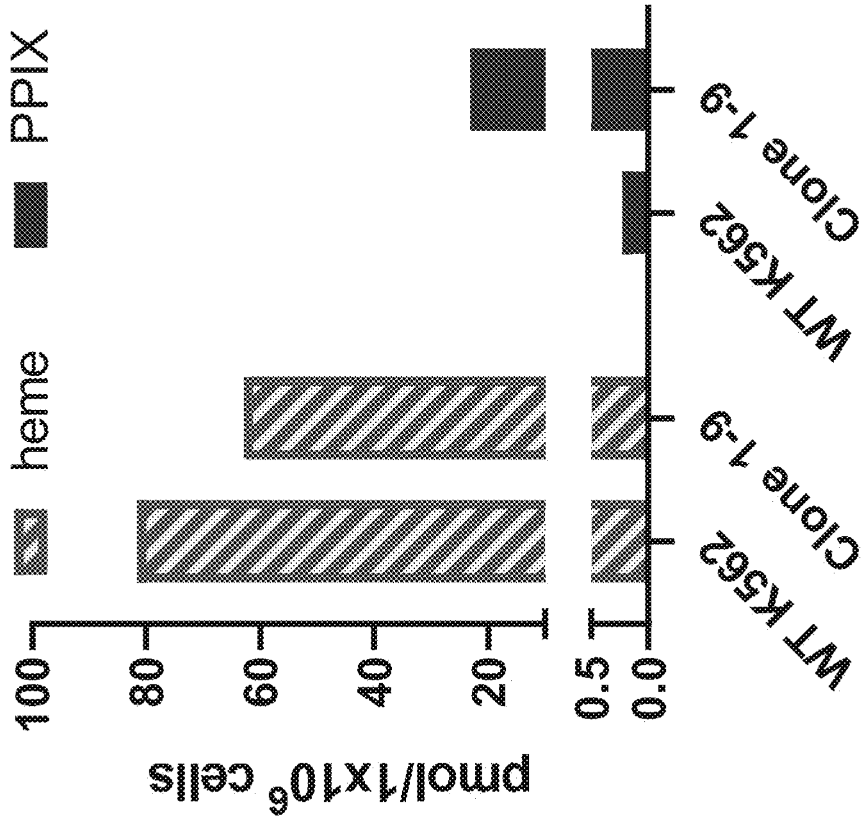
FIG. 3 shows heme and PPIX levels of WT K562 and clone 1-9 cells as determined by LC/MS/MS.

K562 cells were cultured in Iscove's Modified Dulbecco's Medium (IMDM) supplemented with 10% fetal bovine serum (FBS), 1% penicillin/streptomycin (PS). CRISPR Cas9 RNP complex with guide RNA was electroporated in K562 cells. Genomic DNA from the pooled cells was isolated, amplified by PCR and sequenced by Sanger sequencing to determine knockout efficiency. Single-cell clones were isolated by fluorescent-assisted cell sorting (FACS). TA cloning and Sanger sequencing were used to confirm single-cell clones and genotypes. Five clones were selected (Clone IDs are: Clone 1-7; Clone 1-9; Clone 1-10, Clone 1-32; Clone 1-51; and K562 WT) for further characterization by western blot (FIG. 1) to determine FECH protein expression levels (Antibody: FECH Antibody Rabbit Polyclonal, Proteintech, 14466-1-AP) and flow cytometry to determine the PPIX levels (FIG. 2). LC/MS/MS confirmed the accumulation of PPIX in clone 1-9 compared to WT K562 cells (FIG. 3). The genotypic characteristics of the five clones is as provided in Table 2.

TABLE 2

Genotypic Characteristics of Clones

| Clone ID | Genotype |
|---|---|
| K562 WT | WT/WT |
| 1-7 | KO/KO |
| 1-9 | KO/Missense T81H |
| 1-10 | KO/WT |
| 1-32 | KO/WT |
| 1-51 | KO/WT |

Figure 4:
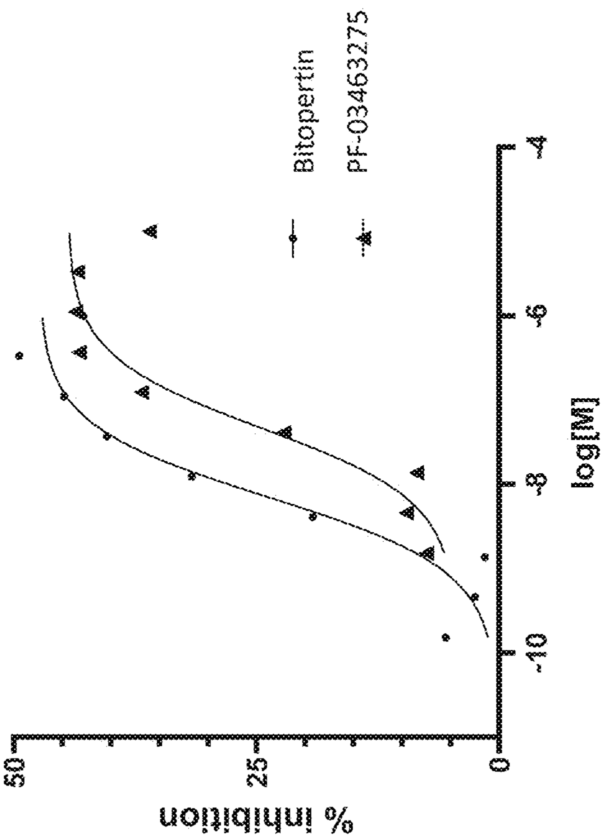
FIG. 4 shows the effects of Bitopertin and PF-03463275 on PPIX levels as determined by flow cytometry.
Figure 5:
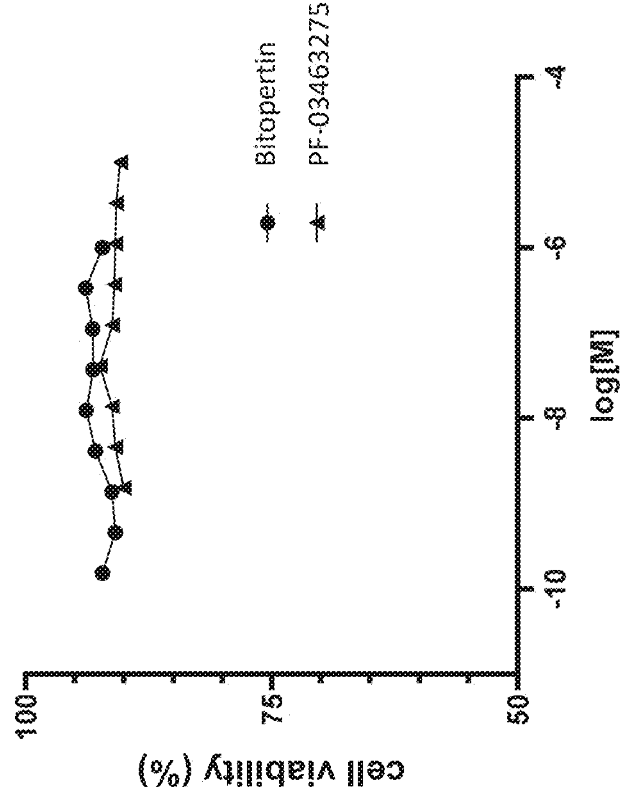
FIG. 5 shows the effects of Bitopertin and PF-03463275 on cell viability as measured by Vi-CELL XR Complete System.
Figure 6:
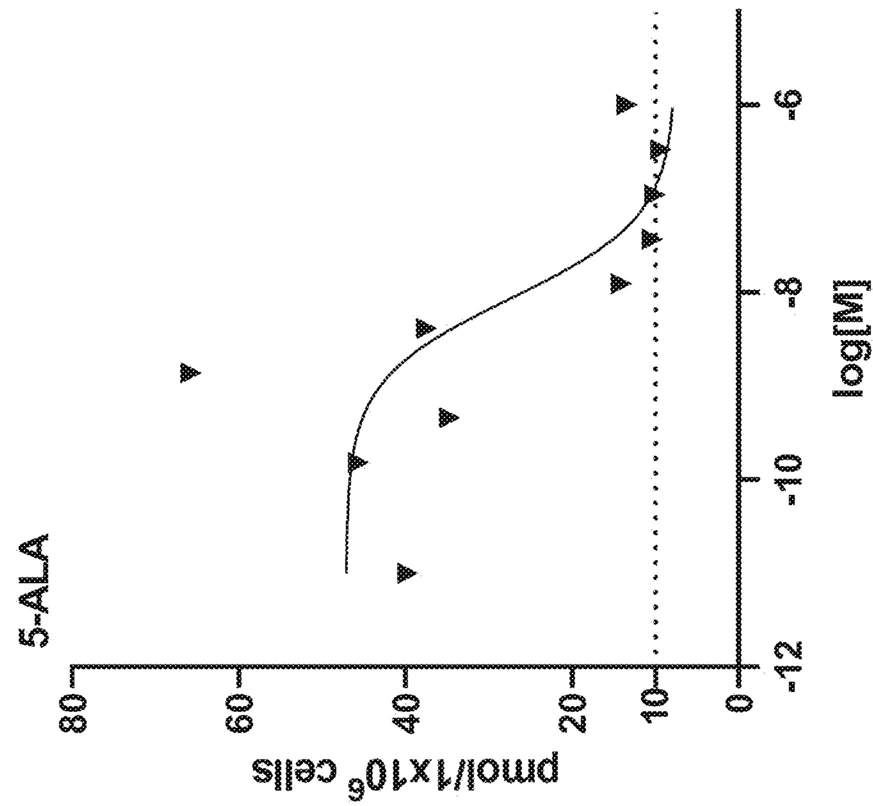
FIG. 6 shows the effect of Bitopertin treatment on 5-Aminelevulinic acid (5-ALA) level of clone 1-9 cells.
Figure 7:
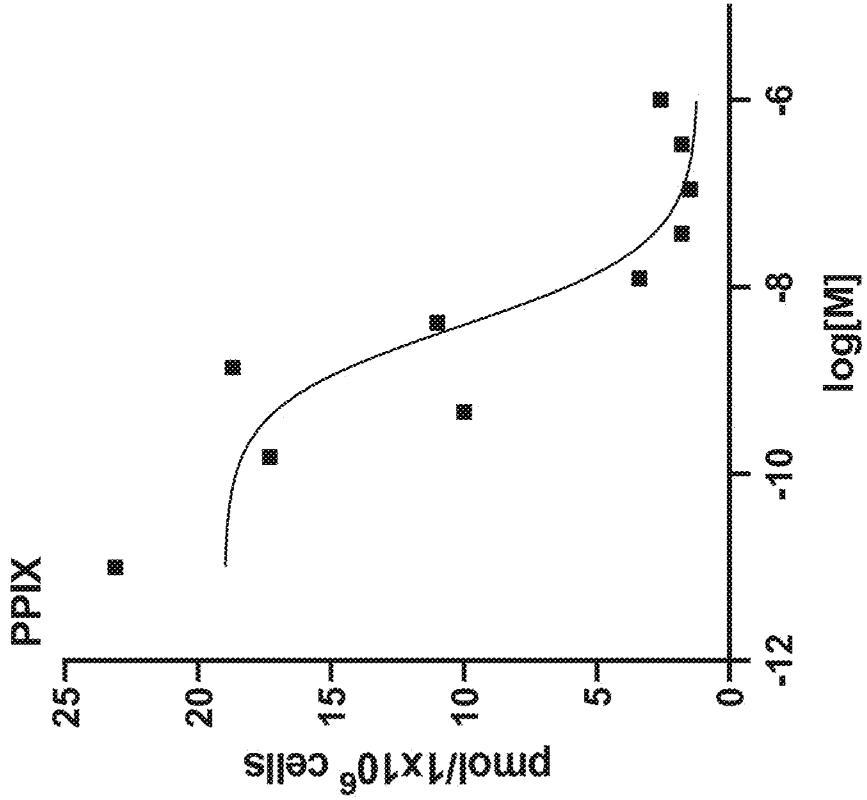
FIG. 7 shows the effect of Bitopertin treatment on PPIX level of clone 1-9 cells.
Figure 8:
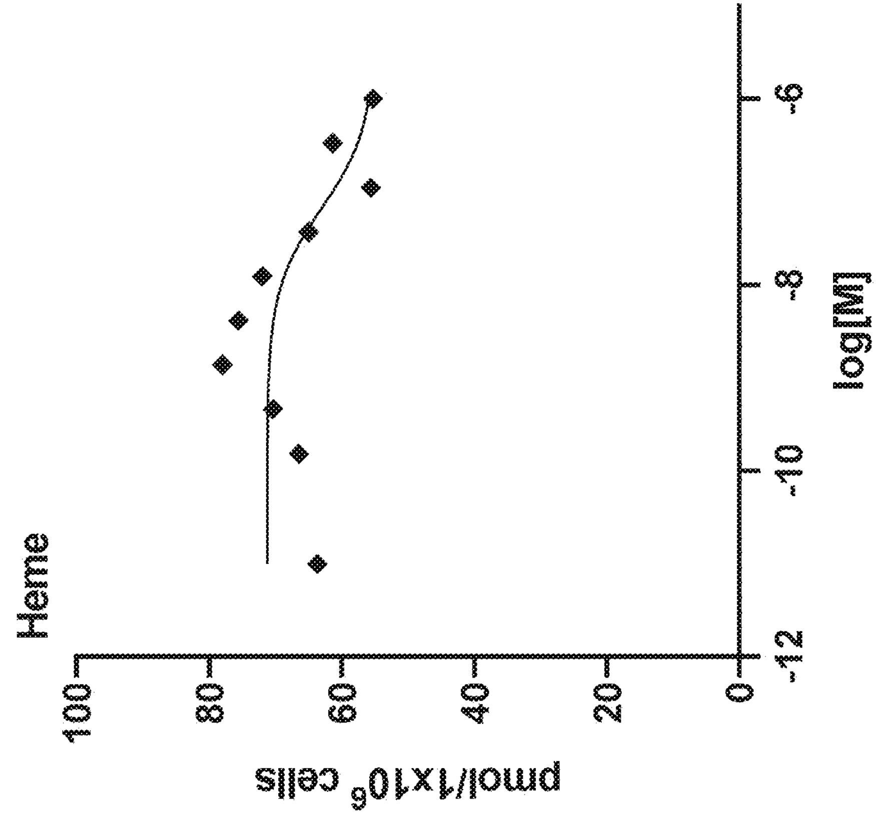
FIG. 8 shows the effect of Bitopertin treatment on Heme level of clone 1-9 cells.

900 μL of K562 clone-9 cells at $2\times10^5$ cells/mL in IMDM media with 10% FBS and 1% PS were plated into a 24-well plate. After 24-hour incubation, 100 μL of compound in DMSO/media was added in different concentration. The final concentration of DMSO was 0.1%. The compound was incubated for 96 hours at 37° C. Cell viability and cell count were measured by Vi-CELL XR Complete System. Finally, the effect of the compound on PPIX level was determined by flow cytometry. FIG. 4 shows that both Bitopertin and PF-03463275 demonstrated a dose-dependent inhibition of PPIX accumulation by flow cytometry, up to 50%. Bitopertin exhibited an EC50 of 7 nM and PF-03463275 exhibited an EC50 of 46 nM FIG. 5 shows that both Bitopertin and PF-03463275 had no negative effects on cell viability. Importantly, LC/MS/MS method demonstrated that Bitopertin decreased 5-aminolevulinic acid (5-ALA) and PPIX levels in the EPP K562 cellular model with minimal effect on Heme formation (FIGS. 6, 7, and 8).

Additional GlyT1 inhibitors also showed a dose-dependent inhibition of PPIX accumulation, while ORG-25543,

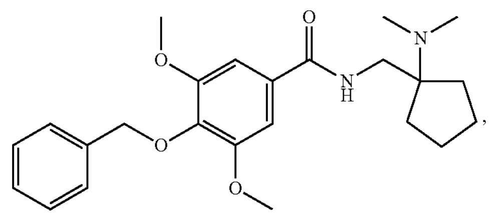 [SMILES: COc1cc(C(=O)NCC2(N(C)C)CCCC2)cc(OC)c1OCc1ccccc1], a GlyT2 inhibitor, did not show any inhibition up to the highest tested concentration of 10 μM (Table 3).

TABLE 3

| EC$_{50}$ of tested compounds in the EPP cellular model | |
|---|---|
| Compound name | EPP cellular model (EC$_{50}$ nM) |
| Bitopertin | 7.0 |
| PF-03463275 | 46 |
| SSR-504734 | 306 |
| ALX-5407 | 0.34 |
| ORG-25935 | 14 |
| ORG-24598 | 5.6 |
| LY-2365109 | 4.1 |
| ORG-25543 | >10,000 |

Example 8: GlyT1 Inhibitors are Effective to Reduce PPIX Level in Human Hematopoietic Stem Cells Transduced with Lentiviruses Expressing Small Interference RNA (shRNA) of FECH To investigate the effects of GlyT1 inhibitors in human hematopoietic stem cells with an EPP phenotype, lentiviral vectors expressing shRNA of FECH were constructed (Table 4) and transduced at 25 MOI into human cord blood-CD34+ cells purchased from Stemexpress.

TABLE 4

| used to construct lentiviral vectors with shRNA sequences of FECH | |
|---|---|
| FECH-shRNA 1-F | CCGGG*CTTTGCAGATCATATTCTAA*CTCGAG*TTAGAATATGATCTGCAAAGC*TTTTTG (SEQ ID NO: 4) |
| FECH-shRNA 1-R | AATTCAAAAA*GCTTTGCAGATCATATTCTAA*CTCGAG*TTAGAATATGATCTGCAAAGC* (SEQ ID NO: 5) |
| Plasmid | pLKO.1 TRC cloning vector |

Figure 9:
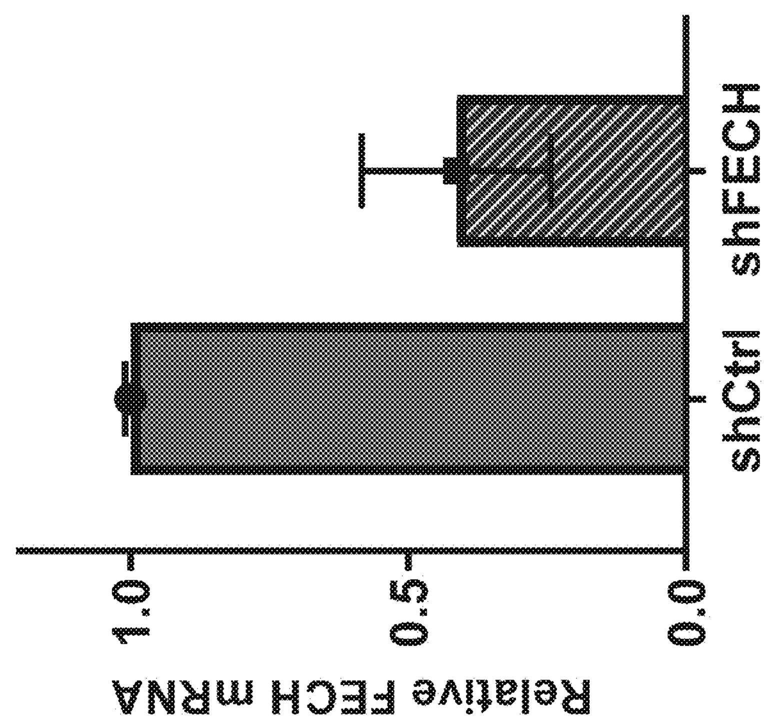
FIG. 9 shows the relative FECH mRNA levels in human hematopoietic stem cells after transduction with lentiviral vectors expressing shRNA of FECH.
Figure 10:
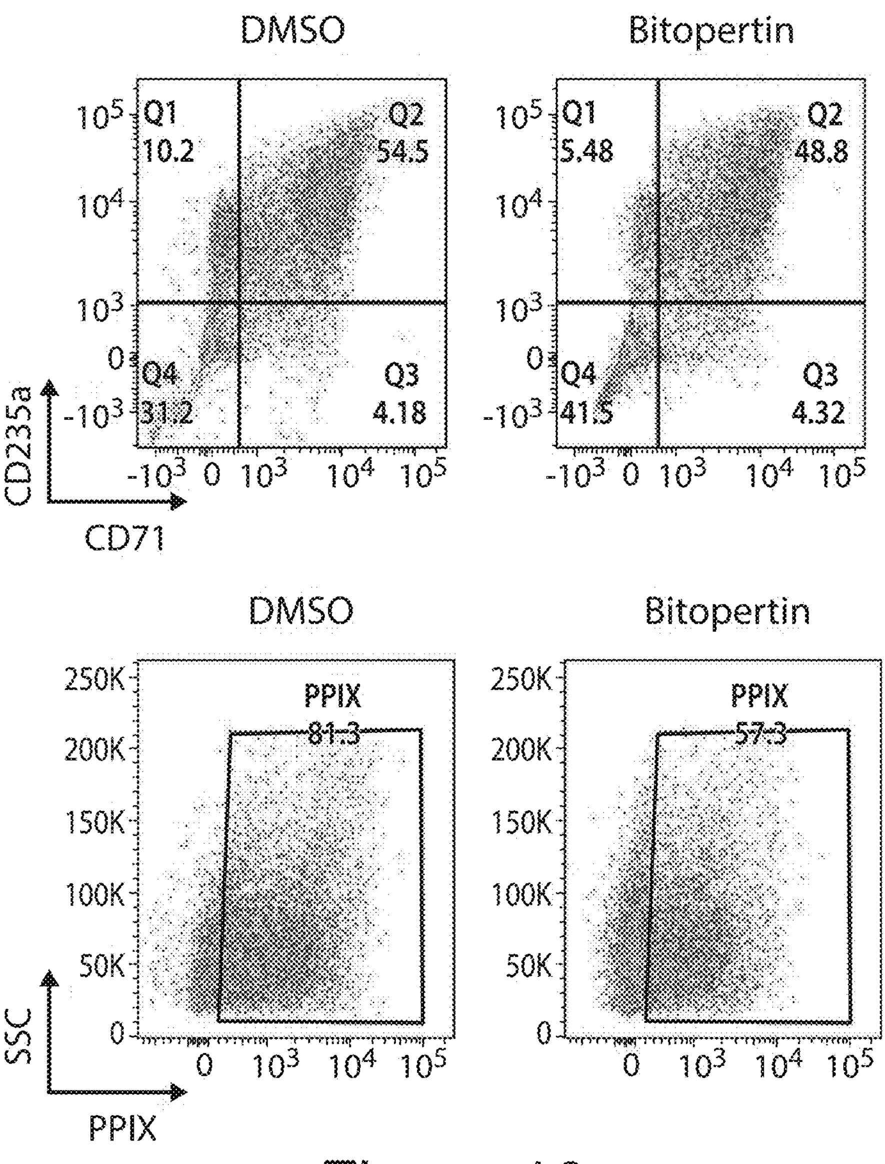
FIG. 10 shows flow cytometry determination of the effects of Bitopertin treatment on the erythroid cell antigen profile and the protoporphyrin IX (PPIX) levels in the human hematopoietic stem cells.
Figure 11:
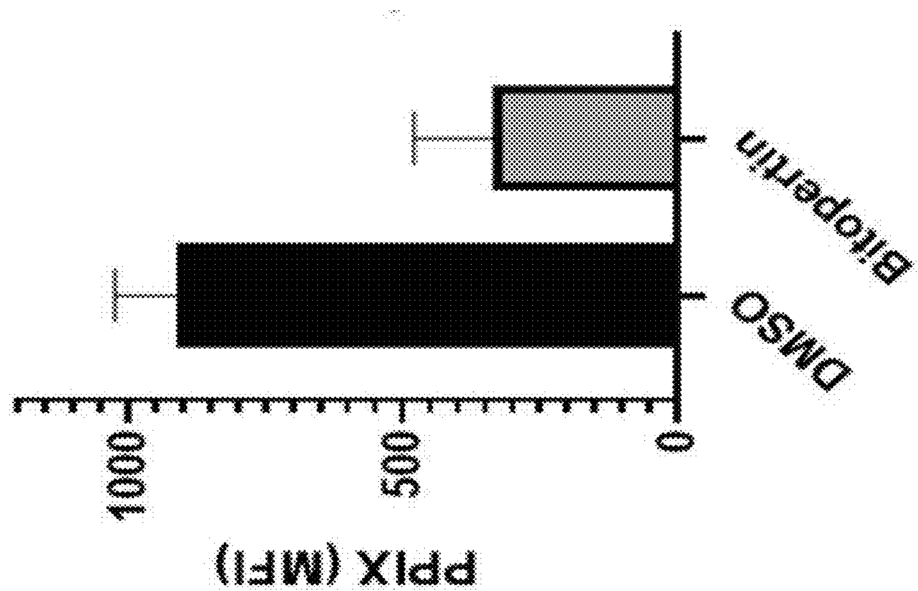
FIG. 11 shows that Biotopertin (100 nM) treatment reduced PPIX accumulation by 60%.

RT-qPCR of the resulted CD34+ cells shows 60% reduction in FECH mRNA level relative to that of cells treated with control lentiviral vectors (FIG. 9). Transduced CD34+ cells were differentiated in the presence of Bitopertin (100 nM) or DMSO control into erythroid cells for 9 days in StemSpan SFEM II media supplemented with StemSpan Erythroid Expansion Supplement. The erythroid cell antigen profile was analyzed using cytofluorimetric strategy with the following surface markers: CD71 (PE Mouse Anti-Human CD71, BD Biosciences), glycophoryin A (APC Mouse Anti-Human CD235a, BD Biosciences). After 9 days in differentiation culture, cell viability was greater than 60% in all samples and more than 80% of cells transduced with lentivirus expressing shRNA of FECH showed an increase in PPIX, determined by flow cytometry (FIG. 10). Treatment of Biotopertin (100 nM) had no negative effects on erythroid cell surface markers and reduced PPIX accumulation by 60% (FIG. 11).

While preferred embodiments of the present application have been shown and described herein, it will be obvious to those skilled in the art that such embodiments are provided by way of example only. Numerous variations, changes, and substitutions will now occur to those skilled in the art without departing from the application. It should be understood that various alternatives to the embodiments of the application described herein may be employed in practicing the application. It is intended that the following claims define the scope of the application and that methods and structures within the scope of these claims and their equivalents be covered thereby.

INCORPORATION BY REFERENCE

All references cited in this application, and their references, are incorporated by reference herein in their entirety where appropriate for teachings of additional or alternative details, features, and/or technical background.

The invention claimed is:

1. A method of treating erythropoietic protoporphyria (EPP), X-linked protoporphyria (XLPP), or congenital erythropoietic porphyria (CEP) in a subject, the method comprising administering to the subject a pharmaceutical composition comprising one or more glycine transporter 1 (GlyT1) inhibitor, or a pharmaceutically acceptable salt thereof, or a prodrug of the one or more GlyT1 inhibitor or its salt.

2. The method of claim 1, comprising further administering to the subject an additional active agent and/or supportive therapy.

3. The method of claim 2, wherein the additional active agent and/or supportive therapy is selected from the group consisting of: avoiding sunlight, topical sunscreens, skin protection, UVB phototherapy, Afamelanotide, bortezomib, proteasome inhibitors, chemical chaperones, cholestyramine, activated charcoal, iron supplementation, liver transplantation, bone marrow transplantation, splenectomy, and blood transfusion.

* * * * *